(12) United States Patent
Tanaka et al.

(10) Patent No.: US 7,968,156 B2
(45) Date of Patent: *Jun. 28, 2011

(54) COMPOUND, COMPOSITION, RETARDATION PLATE, ELLIPTICALLY-POLARIZING PLATE AND LIQUID-CRYSTAL DISPLAY DEVICE

(75) Inventors: Satoshi Tanaka, Minami-ashigara (JP); Makoto Takahashi, Minami-ashigara (JP); Hideyuki Nishikawa, Minami-ashigara (JP); Ichiro Nagata, Minami-ashigara (JP)

(73) Assignee: Fujifilm Corporation, Minato-Ku, Tokyo (JP)

( * ) Notice: Subject to any disclaimer, the term of this patent is extended or adjusted under 35 U.S.C. 154(b) by 625 days.

This patent is subject to a terminal disclaimer.

(21) Appl. No.: 11/908,717

(22) PCT Filed: Mar. 15, 2006

(86) PCT No.: PCT/JP2006/305635
§ 371 (c)(1),
(2), (4) Date: Oct. 23, 2007

(87) PCT Pub. No.: WO2006/098489
PCT Pub. Date: Sep. 21, 2006

(65) Prior Publication Data
US 2009/0233009 A1  Sep. 17, 2009

(30) Foreign Application Priority Data

Mar. 15, 2005  (JP) ................................. 2005-073565
May 23, 2005  (JP) ................................. 2005-149533

(51) Int. Cl.
*G02B 5/30* (2006.01)
*C07D 271/06* (2006.01)
*C07D 413/14* (2006.01)
*C07D 251/14* (2006.01)

(52) U.S. Cl. .......... 428/1.1; 428/1.3; 544/216; 544/221; 546/269.4; 548/131

(58) Field of Classification Search ............... 428/1.1, 428/1.31; 252/299.61, 299.63, 299.67; 548/131; 544/216, 221; 546/269.4
See application file for complete search history.

(56) References Cited

U.S. PATENT DOCUMENTS

| | | | |
|---|---|---|---|
| 5,736,067 A | 4/1998 | Kawata et al. | |
| 6,451,457 B1 | 9/2002 | Taguchi | |
| 7,364,670 B2* | 4/2008 | Nishikawa et al. | 252/299.01 |
| 7,534,371 B2* | 5/2009 | Nishikawa et al. | 252/299.67 |
| 7,696,353 B2 | 4/2010 | Takahashi et al. | |
| 7,763,181 B2* | 7/2010 | Ikeda et al. | 252/299.01 |
| 2002/0039627 A1 | 4/2002 | Ichihashi et al. | |
| 2005/0056811 A1 | 3/2005 | Nishikawa et al. | |
| 2008/0064879 A1* | 3/2008 | Takahashi et al. | 548/131 |
| 2008/0090027 A1* | 4/2008 | Li et al. | 428/1.31 |
| 2008/0113112 A1* | 5/2008 | Ikeda et al. | 428/1.1 |
| 2008/0169448 A1 | 7/2008 | Nishikawa et al. | |
| 2008/0193679 A1* | 8/2008 | Nishikawa et al. | 428/1.1 |
| 2010/0222594 A1 | 9/2010 | Takahashi et al. | |

FOREIGN PATENT DOCUMENTS

| | | |
|---|---|---|
| EP | 1506991 A2 | 2/2005 |
| JP | 7-258170 A | 10/1995 |
| JP | 7-306317 A | 11/1995 |
| JP | 8-048976 A | 2/1996 |
| JP | 2000-096043 A | 4/2000 |
| JP | 2002-129162 A | 5/2002 |
| JP | 2005-122155 A | 5/2005 |
| JP | 2005-122156 A | 5/2005 |
| JP | 2005-338744 A | 12/2005 |
| JP | 2006-076992 A | 3/2006 |
| JP | 2006-091746 A | 4/2006 |
| JP | 2006-119632 A | 5/2006 |
| JP | 2006-248966 A | 9/2006 |
| JP | 2008-514981 A | 5/2008 |
| WO | WO 2006/016724 A2 | 2/2006 |
| WO | WO 2006/035964 A1 | 4/2006 |

OTHER PUBLICATIONS

International Search Report for PCT/JP2006/305635, dated Jun. 6, 2006.
International Preliminary Report of Patentability for PCT/JP2006/305632 dated Sep. 18, 2007.
Office Action from Japanese Patent Office issued in corresponding Japanese Patent Application No. 2006-068609 dated Feb. 22, 2011, with an English translation thereof.

* cited by examiner

*Primary Examiner* — Shean C Wu
(74) *Attorney, Agent, or Firm* — Buchanan Ingersoll & Rooney PC

(57) ABSTRACT

A compound useful for fabrication of retardation plates, which is represented by the formula (DI):

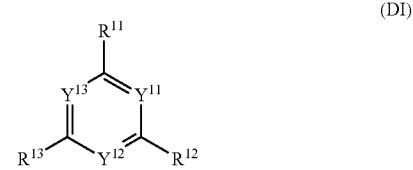

wherein $Y^{11}$ to $Y^{13}$ represent methine or nitrogen; $R^{11}$ to $R^{13}$ represent a group of the formula (DI-A) below or others:

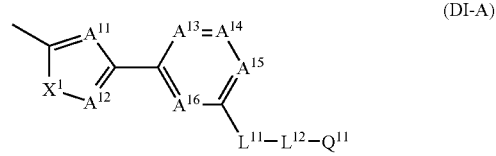

wherein $A^{11}$ to $A^{16}$ represent methine or nitrogen; $X^1$ represents oxygen, sulfur, methylene or imino; $L^{11}$ represents —O—, —C(=O)—, —O—CO—, —CO—O—, —O—CO—O—, —S—, —NH—, —SO$_2$—, —CH$_2$—, —CH=CH—, or —C≡C—; $L^{12}$ represents a divalent linking group; $Q^{11}$ represents polymerizable group or hydrogen.

11 Claims, No Drawings

COMPOUND, COMPOSITION, RETARDATION PLATE, ELLIPTICALLY-POLARIZING PLATE AND LIQUID-CRYSTAL DISPLAY DEVICE

TECHNICAL FIELD

The present invention relates to a compound useful for fabrication of retardation plates and others, and to a composition containing the compound. The invention also relates to a retardation plate having an optically-anisotropic layer formed of the composition, and to an elliptically-polarizing plate comprising the retardation plate.

BACKGROUND ART

It is known that discotic liquid-crystalline compounds are extremely important compounds as a material for optically-compensatory sheets. As a liquid-crystalline compound that expresses discotic liquid-crystallinity, disclosed is 2,3,6,7,10,11-hexa{4-(4-acryloyloxyhexyloxy) benzoyloxy}triphenylene (JP-A 7-306317).

The retardation (Δnd) of an optically-compensatory sheet is determined depending on the optical properties of the liquid-crystal cell to be compensated with the sheet. Retardation (Δnd) is a product of the refractivity anisotropy (Δn) of an optically-anisotropic layer and the thickness (d) of the optically-anisotropic layer. When the refractivity anisotropy (Δn) of an optically-anisotropic layer is large, then the layer may be effective for compensating a liquid-crystal cell even though the thickness (d) of the layer is thin. On the contrary, when the refractivity anisotropy (Δn) thereof is small, then the thickness (d) of the layer must be large, and, as a result, it may be problematic in that there may readily occur defects in the alignment of liquid-crystalline compounds. Compounds having a high Δn are desired.

A compound having a molecular structure similar to that of the liquid-crystalline compound of the invention is reported in Molecular Crystals and Liquid Crystals, 2001, Vol. 370, p. 391 (JD-2; see Comparative Example 2). However, it has been found that the skeleton could not readily attain a lower wavelength dispersibility than 2,3,6,7,10,11-hexa{4-(alkyloxybenzoyloxy}triphenylene, as described in Examples given hereinunder.

DISCLOSURE OF THE INVENTION

Given the situation as above, an object of the invention is to provide a compound capable of satisfying both high Δn and low wavelength dispersibility which conventional discotic liquid-crystalline compounds could not realize. Other objects of the invention are to provide a liquid-crystalline composition containing the compound, to provide a thin film comprising the compound, and to provide a retardation plate and an elliptically-polarizing plate.

The above-mentioned objects can be attained by the following means:

(1) A compound represented by the following formula (DI):

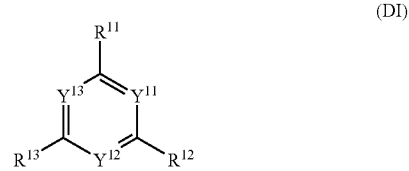

wherein, in formula (DI), $Y^{11}$, $Y^{12}$ and $Y^{13}$ each independently represent a methine group or a nitrogen atom; $R^{11}$, $R^{12}$ and $R^{13}$ each independently represent a group of the following formula (DI-A), (DI-B) or (DI-C):

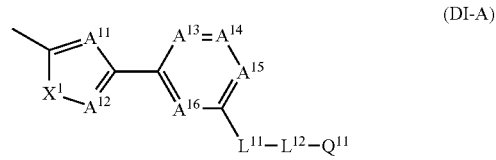

wherein, in formula (DI-A), $A^{11}$, $A^{12}$, $A^{13}$, $A^{14}$, $A^{15}$ and $A^{16}$ each independently represent a methine group or a nitrogen atom; $X^1$ represents an oxygen atom, a sulfur atom, a methylene group or an imino group; $L^{11}$ represents —O—, —C(=O)—, —O—CO—, —CO—O—, —O—CO—O—, —S—, —NH—, —SO$_2$—, —CH$_2$—, —CH=CH—, or —C≡C—; $L^{12}$ represents a divalent linking group selected from the group consisting of —O—, —S—, —C(=O)—, —SO$_2$—, —NH—, —CH$_2$—, —CH=CH— and —C≡C—, and their combinations; when the above-mentioned groups contain a hydrogen atom, then the hydrogen atom may be substituted with a substituent; $Q^{11}$ each independently represents a polymerizable group or a hydrogen atom,

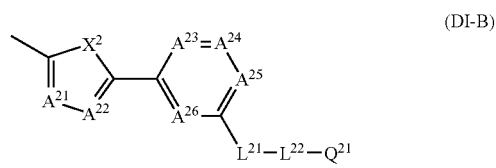

wherein, in formula (DI-B), $A^{21}$, $A^{22}$, $A^{23}$, $A^{24}$, $A^{25}$ and $A^{26}$ each independently represent a methine group or a nitrogen atom; $X^2$ represents an oxygen atom, a sulfur atom, a methylene group or an imino group; $L^{21}$ represents —O—, —C(=O)—, —O—CO—, —CO—O—, —O—CO—O—, —S—, —NH—, —SO$_2$—, —CH$_2$—, —CH=CH—, or —C≡C—; $L^{22}$ represents a divalent linking group selected from the group consisting of —O—, —S—, —C(=O)—, —SO$_2$—, —NH—, —CH$_2$—, —CH=CH— and —C≡C—, and their combinations; when the above-mentioned groups contain a hydrogen atom, then the hydrogen atom may be substituted with a substituent; $Q^{21}$ each independently represents a polymerizable group or a hydrogen atom,

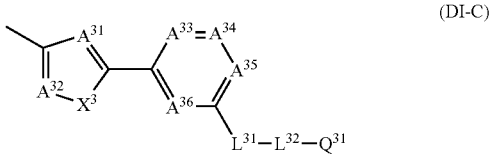

(DI-C)

wherein, in formula (DI-C), $A^{31}$, $A^{32}$, $A^{33}$, $A^{34}$, $A^{35}$ and $A^{36}$ each independently represent a methine group or a nitrogen atom; $X^3$ represents an oxygen atom, a sulfur atom, a methylene group or an imino group; $L^{31}$ represents —O—, —C(=O)—, —O—CO—, —CO—O—, —O—CO—O—, —S—, —NH—, —SO$_2$—, —CH$_2$—, —CH=CH—, or —C≡C—; $L^{32}$ represents a divalent linking group selected from the group consisting of —O—, —S—, —C(=O)—, —SO$_2$—, —NH—, —CH$_2$—, —CH=CH— and —C≡C—, and their combinations; when the above-mentioned groups contain a hydrogen atom, then the hydrogen atom may be substituted with a substituent; $Q^{31}$ each independently represents a polymerizable group or a hydrogen atom.

(2) The compound of above (1) wherein $A^{11}$, $A^{12}$, $A^{21}$, $A^{22}$, $A^{31}$ and $A^{32}$ represent a nitrogen atom.

(3) The compound of above (1) or (2) wherein $X^1$, $X^2$ and $X^3$ represent an oxygen atom.

(4) The compound of any one of above (1) to (3) wherein $A^{13}$, $A^{14}$, $A^{15}$, $A^{16}$, $A^{23}$, $A^{24}$, $A^{25}$, $A^{26}$, $A^{33}$, $A^{34}$, $A^{35}$ and $A^{36}$ represent a methine group.

(5) The compound of any one of above (1) to (4) wherein $R^{11}$, $R^{12}$ and $R^{13}$ represents a group of formula (DI-A).

(6) The compound of above (5) wherein $L^{11}$ represents —O—, —CO—O— or —C≡C—.

(7) A composition comprising the compound of any one of above (1) to (6).

(8) A retardation plate comprising at least one optically-anisotropic layer on a transparent support, wherein the optically-anisotropic layer is formed of a composition comprising a compound represented by the following formula (DII):

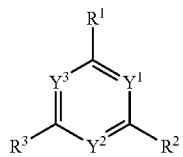

wherein, in formula (DII), $Y^1$, $Y^2$ and $Y^3$ each independently represent a methine group or a nitrogen atom; $R^1$, $R^2$ and $R^3$ each independently represent a group of the following formula (DII-H):

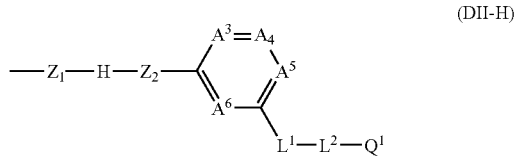

(DII-H)

wherein, in formula (DII-H), H represents a divalent 5-membered cyclic group; $Z^1$ and $Z^2$ each independently represent a single bond or a divalent linking group; $A^3$, $A^4$, $A^5$ and $A^6$ each independently represent a methine group or a nitrogen atom; $L^1$ represents —O—, —C(=O)—, —O—CO—, —CO—O—, —O—CO—O—, —S—, —NH—, —SO$_2$—, —CH$_2$—, —CH=CH—, or —C≡C—; $L^2$ represents a divalent linking group selected from the group consisting of —O—, —S—, —C(=O)—, —SO$_2$—, —NH—, —CH$_2$—, —CH=CH— and —C≡C—, and their combinations; when the above-mentioned groups contain a hydrogen atom, then the hydrogen atom may be substituted with a substituent; $Q^1$ each independently represents a polymerizable group or a hydrogen atom.

(9) An elliptically-polarizing plate comprising the retardation plate of above (8) and a polarizing film.

(10) A liquid-crystal display device comprising the retardation plate of above (8).

(11) A liquid-crystal display device comprising the elliptically-polarizing plate of above (9).

DESCRIPTION OF THE PREFERRED EMBODIMENT

The invention is described in detail hereinunder. In this description, the numerical range expressed by the wording "a number to another number" means the range that falls between the former number indicating the lowermost limit of the range and the latter number indicating the uppermost limit thereof. A liquid-crystalline compound as referred to herein means a compound that expresses liquid-crystallinity.

The compound of the invention is represented by the following formula (DI):

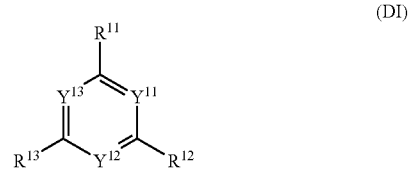

(DI)

In formula (DI), $Y^{11}$, $Y^{12}$ and $Y^{13}$ each independently represent a methine group or a nitrogen atom.

When $Y^{11}$, $Y^{12}$ and $Y^{13}$ each are a methine group, then the hydrogen atom of the methine group may be substituted with a substituent. Preferred examples of the substituent which the methine group may have are an alkyl group, an alkoxy group, an aryloxy group, an acyl group, an alkoxycarbonyl group, an acyloxy group, an acylamino group, an alkoxycarbonylamino group, an alkylthio group, an arylthio group, a halogen atom and a cyano group. Of those substituents, more preferred are an alkyl group, an alkoxy group, an alkoxycarbonyl group, an acyloxy group, a halogen atom and a cyano group; and even more preferred are an alkyl group having from 1 to 12 carbon atoms, an alkoxy group having from 1 to 12 carbon atoms, an alkoxycarbonyl group having from 2 to 12 carbon atoms, an acyloxy group having from 2 to 12 carbon atoms, a halogen atom and a cyano group.

More preferably, $Y^{11}$, $Y^{12}$ and $Y^{13}$ are all methine groups in point of the easiness in producing the compounds and of the cost thereof; and even more preferably, the methine groups are unsubstituted methine groups.

$R^{11}$, $R^{12}$ and $R^{13}$ each independently represent a group of the following formula (DI-A), (DI-B) or (DI-C) When the wavelength dispersibility of the intrinsic birefringence is desired to be lower, then the group of formula (DI-A) or (DI-C) is preferred; and the group of formula (DI-A) is more preferred. Preferably, $R^{11}$, $R^{12}$ and $R^{13}$ are $R^{11}$=$R^{12}$=$R^{13}$.

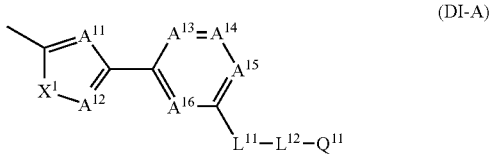

(DI-A)

In formula (DI-A), $A^{11}$, $A^{12}$, $A^{13}$, $A^{14}$, $A^{15}$ and $A^{16}$ each independently represent a methine group or a nitrogen atom.

Preferably, at least one of $A^{11}$ and $A^{12}$ is a nitrogen atom; and more preferably, the two are both nitrogen atoms.

Preferably, at least three of $A^{13}$, $A^{14}$, $A^{15}$ and $A^{16}$ are methine groups; and more preferably, they are all methine groups. Preferably, the methine groups are unsubstituted.

Examples of the substituent for the methine group for $A^{11}$, $A^{12}$, $A^{13}$, $A^{14}$, $A^{15}$ and $A^{16}$ include a halogen atom (fluorine atom, chlorine atom, bromine atom, iodine atom), a cyano group, a nitro group, an alkyl group having from 1 to 16 carbon atoms, an alkenyl group having from 2 to 16 carbon atoms, an alkynyl group having from 2 to 16 carbon atoms, a halogen-substituted alkyl group having from 1 to 16 carbon atoms, an alkoxy group having from 1 to 16 carbon atoms, an acyl group having from 2 to 16 carbon atoms, an alkylthio group having from 1 to 16 carbon atoms, an acyloxy group having from 2 to 16 carbon atoms, an alkoxycarbonyl group having from 2 to 16 carbon atoms, a carbamoyl group, an alkyl-substituted carbamoyl group having from 2 to 16 carbon atoms, and an acylamino group having from 2 to 16 carbon atoms. Of those, preferred are a halogen atom, a cyano group, an alkyl group having from 1 to 6 carbon atoms, a halogen-substituted alkyl group having from 1 to 6 carbon atoms; more preferred are a halogen atom, an alkyl group having from 1 to 4 carbon atoms, a halogen-substituted alkyl group having from 1 to 4 carbon atoms; and even more preferred are a halogen atom, an alkyl group having from 1 to 3 carbon atoms, and a trifluoromethyl group.

$X^1$ represents an oxygen atom, a sulfur atom, a methylene group or an imino group, preferably an oxygen atom.

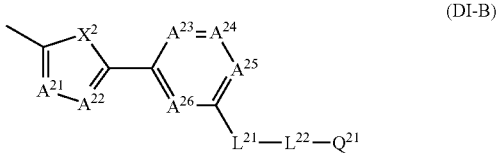

(DI-B)

In formula (DI-B), $A^{21}$, $A^{22}$, $A^{23}$, $A^{24}$, $A^{25}$ and $A^{26}$ each independently represent a methine group or a nitrogen atom.

Preferably, at least one of $A^{21}$ and $A^{22}$ is a nitrogen atom; and more preferably, the two are both nitrogen atoms.

Preferably, at least three of $A^{23}$, $A^{24}$, $A^{25}$ and $A^{26}$ are methine groups; and more preferably, they are all methine groups.

When $A^{21}$, $A^{22}$, $A^{23}$, $A^{24}$, $A^{25}$ or $A^{26}$ is a methine group, examples of the substituent for the methine group include a halogen atom (fluorine atom, chlorine atom, bromine atom, iodine atom), a cyano group, a nitro group, an alkyl group having from 1 to 16 carbon atoms, an alkenyl group having from 2 to 16 carbon atoms, an alkynyl group having from 2 to 16 carbon atoms, a halogen-substituted alkyl group having from 1 to 16 carbon atoms, an alkoxy group having from 1 to 16 carbon atoms, an acyl group having from 2 to 16 carbon atoms, an alkylthio group having from 1 to 16 carbon atoms, an acyloxy group having from 2 to 16 carbon atoms, an alkoxycarbonyl group having from 2 to 16 carbon atoms, a carbamoyl group, an alkyl-substituted carbamoyl group having from 2 to 16 carbon atoms, and an acylamino group having from 2 to 16 carbon atoms. Of those, preferred are a halogen atom, a cyano group, an alkyl group having from 1 to 6 carbon atoms, a halogen-substituted alkyl group having from 1 to 6 carbon atoms; more preferred are a halogen atom, an alkyl group having from 1 to 4 carbon atoms, a halogen-substituted alkyl group having from 1 to 4 carbon atoms; and even more preferred are a halogen atom, an alkyl group having from 1 to 3 carbon atoms, and a trifluoromethyl group.

$X^2$ represents an oxygen atom, a sulfur atom, a methylene group or an imino group, preferably an oxygen atom.

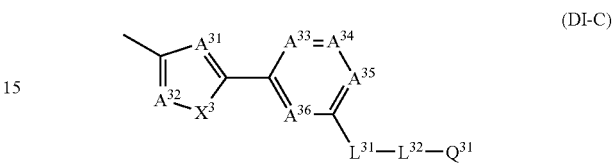

(DI-C)

In formula (DI-C), $A^{31}$, $A^{32}$, $A^{33}$, $A^{34}$, $A^{35}$ and $A^{36}$ each independently represent a methine group or a nitrogen atom.

Preferably, at least one of $A^{31}$ and $A^{32}$ is a nitrogen atom; and more preferably, the two are both nitrogen atoms.

Preferably, at least three of $A^{33}$, $A^{34}$, $A^{35}$ and $A^{36}$ are methine groups; and more preferably, they are all methine groups.

When $A^{31}$, $A^{32}$, $A^{33}$, $A^{34}$, $A^{35}$ or $A^{36}$ is a methine group, then the methine group may have a substituent. Examples of the substituent include a halogen atom (fluorine atom, chlorine atom, bromine atom, iodine atom), a cyano group, a nitro group, an alkyl group having from 1 to 16 carbon atoms, an alkenyl group having from 2 to 16 carbon atoms, an alkynyl group having from 2 to 16 carbon atoms, a halogen-substituted alkyl group having from 1 to 16 carbon atoms, an alkoxy group having from 1 to 16 carbon atoms, an acyl group having from 2 to 16 carbon atoms, an alkylthio group having from 1 to 16 carbon atoms, an acyloxy group having from 2 to 16 carbon atoms, an alkoxycarbonyl group having from 2 to 16 carbon atoms, a carbamoyl group, an alkyl-substituted carbamoyl group having from 2 to 16 carbon atoms, and an acylamino group having from 2 to 16 carbon atoms. Of those, preferred are a halogen atom, a cyano group, an alkyl group having from 1 to 6 carbon atoms, a halogen-substituted alkyl group having from 1 to 6 carbon atoms; more preferred are a halogen atom, an alkyl group having from 1 to 4 carbon atoms, a halogen-substituted alkyl group having from 1 to 4 carbon atoms; and even more preferred are a halogen atom, an alkyl group having from 1 to 3 carbon atoms, and a trifluoromethyl group.

$X^3$ represents an oxygen atom, a sulfur atom, a methylene group or an imino group, preferably an oxygen atom.

$L^{11}$ in formula (DI-A), $L^{21}$ in formula (DI-B), and $L^{31}$ in formula (DI-C) each independently represent —O—, —C(=O)—, —O—CO—, —CO—O—, —O—CO—O—, —S—, —NH—, —SO$_2$—, —CH$_2$—, —CH=CH—, or —C≡C—; preferably —O—, —C(=O)—, —O—CO—, —CO—O—, —O—CO—O—, —CH$_2$—, —CH=CH—, or —C≡C—; more preferably —O—, —O—CO—, —CO—O—, —O—CO—O—, or —C≡C—. In particular, $L^{11}$ in formula (DI-A) is especially preferably —O—, —CO—O— or —C≡C—, as the wavelength dispersibility of the intrinsic birefringence may be expected to be lower; and above all, $L^{11}$ is even more preferably —CO—O—, as the compound may express a discotic nematic phase at a higher temperature. When the above-mentioned groups contain a hydrogen atom, then the hydrogen atom may be substituted with a substituent. Preferred examples of the substituent are a halogen atom, a cyano group, a nitro group, an alkyl group having from 1 to 6 carbon atoms, a halogen-substituted alkyl group having from 1 to 6 carbon atoms, an alkoxy group having from 1 to 6 carbon atoms, an acyl group having from 2 to 6 carbon atoms, an alkylthio group having from 1 to 6 carbon atoms, an acyloxy group having from 2 to 6 carbon atoms, an alkoxycarbonyl group having from 2 to 6 carbon atoms, a carbamoyl group, an alkyl-substituted carbamoyl group having from 2 to 6 carbon atoms, and an acylamino group having from 2 to 6 carbon atoms. More preferred are a halogen atom, and an alkyl group having from 1 to 6 carbon atoms.

$L^{12}$ in formula (DI-A), $L^{22}$ in formula (DI-B), and $L^{32}$ in formula (DI-C) each independently represent a divalent linking group selected from the group consisting of —O—, —S—, —C(=O)—, —SO$_2$—, —NH—, —CH$_2$—, —CH=CH— and —C≡C—, and their combinations. In these, the hydrogen atom of —NH—, —CH$_2$— and —CH=CH— may be substituted with a substituent. Preferred examples of the substituent are a halogen atom, a cyano group, a nitro group, a hydroxyl group, a carboxyl group, an alkyl group having from 1 to 6 carbon atoms, a halogen-substituted alkyl group having from 1 to 6 carbon atoms, an alkoxy group having from 1 to 6 carbon atoms, an acyl group having from 2 to 6 carbon atoms, an alkylthio group having from 1 to 6 carbon atoms, an acyloxy group having from 2 to 6 carbon atoms, an alkoxycarbonyl group having from 2 to 6 carbon atoms, a carbamoyl group, an alkyl-substituted carbamoyl group having from 2 to 6 carbon atoms, and an acylamino group having from 2 to 6 carbon atoms. More preferred are a halogen atom, a hydroxyl group, and an alkyl group having from 1 to 6 carbon atoms; and even more preferred are a halogen atom, a methyl group and an ethyl group.

Preferably, $L^{12}$, $L^{22}$ and $L^{32}$ are independently selected from the group consisting of —O—, —C(=O)—, —CH$_2$—, —CH=CH— and —C≡C—, and their combinations.

More preferably, $L^{12}$, $L^{22}$ and $L^{32}$ independently have from 1 to 20 carbon atoms, even more preferably from 2 to 14 carbon atoms. Preferably, they independently have from 1 to 16 (—CH$_2$-)s, more preferably from 2 to 12 (—CH$_2$-)s.

The number of the carbon atoms constituting $L^{12}$, $L^{22}$ and $L^{32}$ has an influence on the phase-transition temperature of the liquid crystal and on the solubility of the compound in solvents. In general, when the number of the carbon atoms is larger, then the temperature for phase transition from the discotic nematic phase (N$_D$ phase) to the isotropic liquid phase tends to be lower. On the other hand, the solubility of the compound in solvent tends to be higher when the number of the carbon atoms is larger.

$Q^{11}$ in formula (DI-A), $Q^{21}$ in formula (DI-B) and $Q^{31}$ in formula (DI-C) each independently represent a polymerizable group or a hydrogen atom. When the compound of the invention is used in an optical film such as an optically-compensatory film, of which the retardation is desired not to change by heat, then $Q^{11}$, $Q^{21}$ and $Q^{31}$ are preferably a polymerizable group. The polymerization reaction is preferably addition polymerization (including ring-cleavage polymerization) or condensation polymerization. Specifically, it is desirable that the polymerizable group is a functional group capable of undergoing addition polymerization or condensation polymerization. Examples of the polymerizable group are mentioned below.

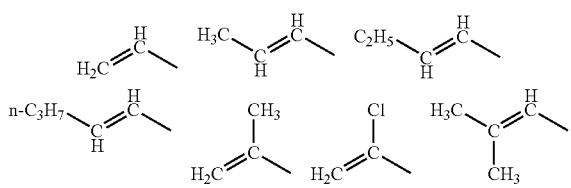

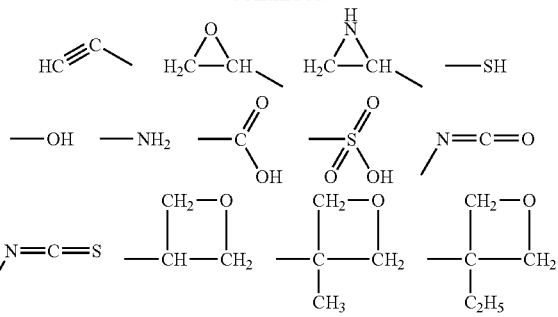

More preferably, the polymerizable group is a functional group capable of undergoing addition polymerization. The polymerizable group of the type is preferably a polymerizable ethylenic unsaturated group or a ring-cleavage polymerizable group.

Examples of the polymerizable ethylenic unsaturated group are the following formulae (M-1) to (M-6):

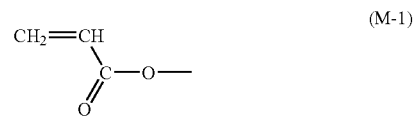

(M-1)

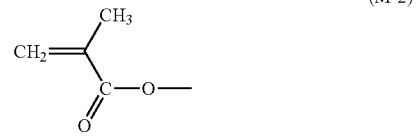

(M-2)

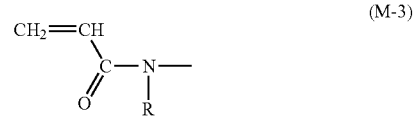

(M-3)

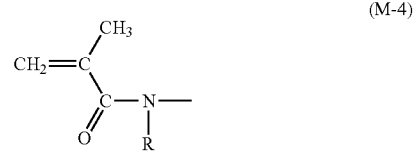

(M-4)

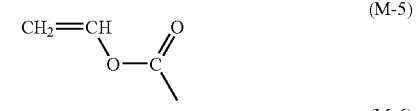

(M-5)

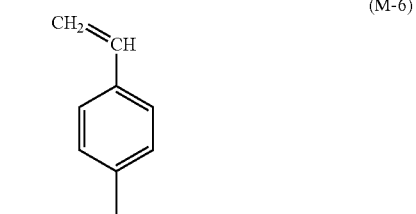

(M-6)

In formulae (M-3) and (M-4), R represents a hydrogen atom or an alkyl group, preferably a hydrogen atom or a methyl group.

Of formulae (M-1) to (M-6), preferred are (M-1) and (M-2); and more preferred is (M-1).

The ring-cleavage polymerizable group is preferably a cyclic ether group, more preferably an epoxy group or an oxetanyl group.

Examples of the compounds of formula (DI) are mentioned below, to which, however, the invention should not be limited.

| | | | |
|---|---|---|---|
| Ar: 1,3,5-trisubstituted benzene (R,R,R) | R = 5-methyl-3-(3-X-phenyl)-1,2,4-oxadiazole | X = —OC₄H₉ | D-1 |
| | | —OC₅H₁₁ | D-2 |
| | | —OC₆H₁₃ | D-3 |
| | | —OC₇H₁₅ | D-4 |
| | | —OC₈H₁₇ | D-5 |
| | | —OCH₂CH(CH₃)C₄H₉ | D-6 |
| | | —O(CH₂)₂OCOCH=CH₂ | D-7 |
| | | —O(CH₂)₃OCOCH=CH₂ | D-8 |
| | | —O(CH₂)₄OCOCH=CH₂ | D-9 |
| | | —O(CH₂)₅OCOCH=CH₂ | D-10 |
| | | —O(CH₂)₆OCOCH=CH₂ | D-11 |
| | | —O(CH₂)₇OCOCH=CH₂ | D-12 |
| | | —O(CH₂)₈OCOCH=CH₂ | D-13 |
| | | —O(CH₂)₂CH(CH₃)OCOCH=CH₂ | D-14 |
| | | —O(CH₂)₃CH(CH₃)OCOCH=CH₂ | D-15 |
| | | —O(CH₂CH₂O)₂COCH=CH₂ | D-16 |
| | | —O(CH₂)₄OCOC(CH₃)=CH₂ | D-17 |
| | | —O(CH₂)₄OCOCH=CHCH₃ | D-18 |
| | | —O(CH₂)₄OCH=CH₂ | D-19 |
| | | —O(CH₂)₄—CH(—O—)CH₂ (glycidyl) | D-20 |

| | | | |
|---|---|---|---|
| Ar: 1,3,5-trisubstituted benzene (R,R,R) | R = 5-methyl-3-(3-X-phenyl)-1,2,4-oxadiazole | X = —OCOC₄H₉ | D-21 |
| | | —OCOC₅H₁₁ | D-22 |
| | | —OCOC₆H₁₃ | D-23 |
| | | —OCO(CH₂)₂OCOCH=CH₂ | D-24 |
| | | —OCO(CH₂)₃OCOCH=CH₂ | D-25 |
| | | —OCO(CH₂)₄OCOCH=CH₂ | D-26 |
| | | —OCO(CH₂)₅OCOCH=CH₂ | D-27 |
| | | —OCO(CH₂)₆OCOCH=CH₂ | D-28 |
| | | —OCO(CH₂)₇OCOCH=CH₂ | D-29 |
| | | —OCO(CH₂)₂CH(CH₃)OCOCH=CH₂ | D-30 |
| | | —OCO(CH₂)₂OCOC(CH₃)=CH₂ | D-31 |
| | | —OCO(CH₂)₂OCOCH=CHCH₃ | D-32 |
| | | —OCO(CH₂)₄OCH=CH₂ | D-33 |
| | | —OCO(CH₂)₄—CH(—O—)CH₂ | D-34 |

| | | | |
|---|---|---|---|
| Ar: 1,3,5-trisubstituted benzene (R,R,R) | R = 5-methyl-3-(3-X-phenyl)-1,2,4-oxadiazole | X = —OCOOC₄H₉ | D-35 |
| | | —OCOOC₅H₁₁ | D-36 |
| | | —OCOOC₆H₁₃ | D-37 |
| | | —OCOO(CH₂)₂OCOCH=CH₂ | D-38 |
| | | —OCOO(CH₂)₃OCOCH=CH₂ | D-39 |
| | | —OCOO(CH₂)₄OCOCH=CH₂ | D-40 |
| | | —OCOO(CH₂)₅OCOCH=CH₂ | D-41 |
| | | —OCOO(CH₂)₆OCOCH=CH₂ | D-42 |
| | | —OCOO(CH₂)₇OCOCH=CH₂ | D-43 |
| | | —OCOOCH(CH₃)CH₂CH₂OCOCH=CH₂ | D-44 |
| | | —OCOOC(CH₂CH₂O)₂COCH=CH₂ | D-45 |
| | | —OCOO(CH₂)₂OCOC(CH₃)=CH₂ | D-46 |
| | | —OCOO(CH₂)₂OCOCH=CHCH₃ | D-47 |
| | | —OCOO(CH₂)₄OCH=CH₂ | D-48 |
| | | —OCOO(CH₂)₄—CH(—O—)CH₂ | D-49 |

| R | R = | X | |
|---|---|---|---|
| 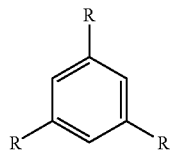 | 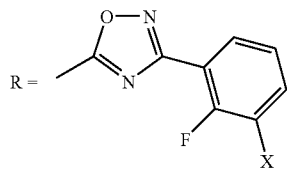 | X = —OC$_6$H$_{13}$ | D-50 |
| | | —OCOC$_5$H$_{11}$ | D-51 |
| | | —OCOOC$_4$H$_9$ | D-52 |
| | | —O(CH$_2$)$_4$OCOCH=CH$_2$ | D-53 |
| | | —O(CH$_2$)$_6$OCOCH=CH$_2$ | D-54 |
| | | —OCO(CH$_2$)$_3$OCOCH=CH$_2$ | D-55 |
| | | —OCO(CH$_2$)$_4$OCOCH=CH$_2$ | D-56 |
| | | —OCOO(CH$_2$)$_2$OCOCH=CH$_2$ | D-57 |
| | | —OCOO(CH$_2$)$_4$OCOCH=CH$_2$ | D-58 |
| | | 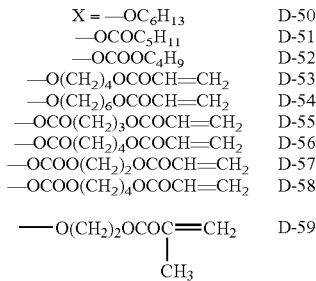 | D-59 |
| | | —O(CH$_2$)$_2$OCOCH=CHCH$_3$ | D-60 |
| | | —O(CH$_2$)$_4$OCH=CH$_2$ | D-61 |
| | | —O(CH$_2$)$_4$—CH—CH$_2$ (epoxide) | D-62 |
| 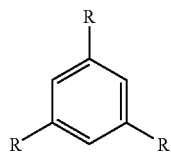 | 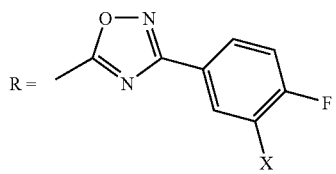 | X = —OC$_6$H$_{13}$ | D-63 |
| | | —OCOC$_5$H$_{11}$ | D-64 |
| | | —OCOOC$_4$H$_9$ | D-65 |
| | | —O(CH$_2$)$_4$OCOCH=CH$_2$ | D-66 |
| | | —O(CH$_2$)$_6$OCOCH=CH$_2$ | D-67 |
| | | —OCO(CH$_2$)$_3$OCOCH=CH$_2$ | D-68 |
| | | —OCO(CH$_2$)$_4$OCOCH=CH$_2$ | D-69 |
| | | OCOO(CH$_2$)$_2$OCOCH=CH$_2$ | D-70 |
| | | —OCOO(CH$_2$)$_4$OCOCH=CH$_2$ | D-71 |
| | | 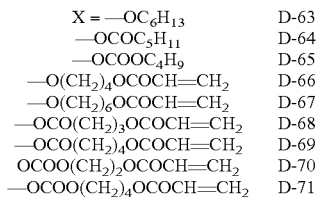 | D-72 |
| | | —O(CH$_2$)$_2$OCOCH=CHCH$_3$ | D-73 |
| | | —O(CH$_2$)$_4$OCH=CH$_2$ | D-74 |
| | | —O(CH$_2$)$_4$—CH—CH$_2$ (epoxide) | D-75 |
| 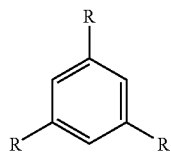 | 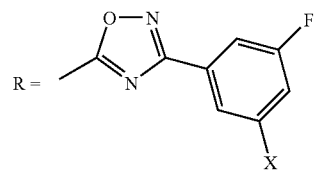 | X = —OC$_6$H$_{13}$ | D-76 |
| | | —OCOC$_5$H$_{11}$ | D-77 |
| | | —OCOOC$_4$H$_9$ | D-78 |
| | | —O(CH$_2$)$_4$OCOCH=CH$_2$ | D-79 |
| | | —O(CH$_2$)$_6$OCOCH=CH$_2$ | D-80 |
| | | —OCO(CH$_2$)$_3$OCOCH=CH$_2$ | D-81 |
| | | —OCO(CH$_2$)$_4$OCOCH=CH$_2$ | D-82 |
| | | —OCOO(CH$_2$)$_2$OCOCH=CH$_2$ | D-83 |
| | | —OCOO(CH$_2$)$_4$OCOCH=CH$_2$ | D-84 |
| | | 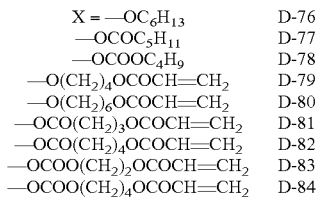 | D-85 |
| | | —O(CH$_2$)$_2$OCOCH=CHCH$_3$ | D-86 |
| | | —O(CH$_2$)$_4$OCH=CH$_2$ | D-87 |
| | | —O(CH$_2$)$_4$—CH—CH$_2$ (epoxide) | D-88 |
| 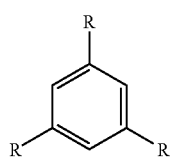 | 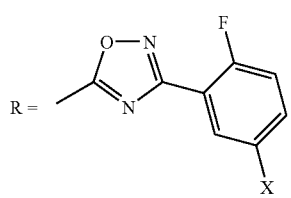 | X = —OC$_6$H$_{13}$ | D-89 |
| | | —OCOC$_5$H$_{11}$ | D-90 |
| | | —OCOOC$_4$H$_9$ | D-91 |
| | | —O(CH$_2$)$_4$OCOCH=CH$_2$ | D-92 |
| | | —O(CH$_2$)$_6$OCOCH=CH$_2$ | D-93 |
| | | —OCO(CH$_2$)$_3$OCOCH=CH$_2$ | D-94 |
| | | —OCO(CH$_2$)$_4$OCOCH=CH$_2$ | D-95 |
| | | —OCOO(CH$_2$)$_2$OCOCH=CH$_2$ | D-96 |
| | | —OCOO(CH$_2$)$_4$OCOCH=CH$_2$ | D-97 |
| | | 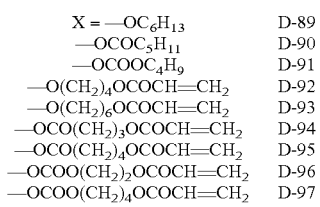 | D-98 |
| | | —O(CH$_2$)$_2$OCOCH=CHCH$_3$ | D-99 |

-continued

| | | | |
|---|---|---|---|
| | | —O(CH₂)₄OCH=CH₂ | D-100 |
| | | —O(CH₂)₄—CH—CH₂ (epoxide) | D-101 |
| R = 1,3,5-trisubstituted benzene | 5-R-3-(4-chloro-3-X-phenyl)-1,2,4-oxadiazole | X = —OC₆H₁₃ | D-102 |
| | | —OCOC₅H₁₁ | D-103 |
| | | —OCOOC₄H₉ | D-104 |
| | | —O(CH₂)₄OCOCH=CH₂ | D-105 |
| | | —O(CH₂)₆OCOCH=CH₂ | D-106 |
| | | —OCO(CH₂)₃OCOCH=CH₂ | D-107 |
| | | —OCO(CH₂)₄OCOCH=CH₂ | D-108 |
| | | —OCOO(CH₂)₂OCOCH=CH₂ | D-109 |
| | | —OCOO(CH₂)₄OCOCH=CH₂ | D-110 |
| | | —O(CH₂)₂OCOC(CH₃)=CH₂ | D-111 |
| | | —O(CH₂)₂OCOCH=CHCH₃ | D-112 |
| | | —O(CH₂)₄OCH=CH₂ | D-113 |
| | | —O(CH₂)₄—CH—CH₂ (epoxide) | D-114 |
| R = 1,3,5-trisubstituted benzene | 5-R-3-(4-bromo-3-X-phenyl)-1,2,4-oxadiazole | X = —OC₆H₁₃ | D-115 |
| | | —OCOC₅H₁₁ | D-116 |
| | | —OCOOC₄H₉ | D-117 |
| | | —O(CH₂)₄OCOCH=CH₂ | D-118 |
| | | —O(CH₂)₆OCOCH=CH₂ | D-119 |
| | | —OCO(CH₂)₃OCOCH=CH₂ | D-120 |
| | | —OCO(CH₂)₄OCOCH=CH₂ | D-121 |
| | | —OCOO(CH₂)₂OCOCH=CH₂ | D-122 |
| | | —OCOO(CH₂)₄OCOCH=CH₂ | D-123 |
| | | —O(CH₂)₂OCOC(CH₃)=CH₂ | D-124 |
| | | —O(CH₂)₂OCOCH=CHCH₃ | D-125 |
| | | —O(CH₂)₄OCH=CH₂ | D-126 |
| | | —O(CH₂)₄—CH—CH₂ (epoxide) | D-127 |
| R = 1,3,5-trisubstituted benzene | 5-R-3-(4-methyl-3-X-phenyl)-1,2,4-oxadiazole | X = —OC₆H₁₃ | D-128 |
| | | —OCOC₅H₁₁ | D-129 |
| | | —OCOOC₄H₉ | D-130 |
| | | —O(CH₂)₄OCOCH=CH₂ | D-131 |
| | | —O(CH₂)₆OCOCH=CH₂ | D-132 |
| | | —OCO(CH₂)₃OCOCH=CH₂ | D-133 |
| | | —OCO(CH₂)₄OCOCH=CH₂ | D-134 |
| | | —OCOO(CH₂)₂OCOCH=CH₂ | D-135 |
| | | —OCOO(CH₂)₄OCOCH=CH₂ | D-136 |
| | | —O(CH₂)₂OCOC(CH₃)=CH₂ | D-137 |
| | | —O(CH₂)₂OCOCH=CHCH₃ | D-138 |
| | | —O(CH₂)₄OCH=CH₂ | D-139 |
| | | —O(CH₂)₄—CH—CH₂ (epoxide) | D-140 |
| R = 1,3,5-trisubstituted benzene | 3-R-5-(3-X-phenyl)-1,2,4-oxadiazole | X = —OC₆H₁₃ | D-141 |
| | | —OCOC₅H₁₁ | D-142 |
| | | —OCOOC₄H₉ | D-143 |
| | | —O(CH₂)₄OCOCH=CH₂ | D-144 |
| | | —O(CH₂)₆OCOCH=CH₂ | D-145 |
| | | —OCO(CH₂)₃OCOCH=CH₂ | D-146 |
| | | —OCO(CH₂)₄OCOCH=CH₂ | D-147 |
| | | —OCOO(CH₂)₂OCOCH=CH₂ | D-148 |
| | | —OCOO(CH₂)₄OCOCH=CH₂ | D-149 |

-continued

| | | |
|---|---|---|
| | —O(CH₂)₂OCOC(CH₃)=CH₂ | D-150 |
| | —O(CH₂)₂OCOCH=CHCH₃ | D-151 |
| | —O(CH₂)₄OCH=CH₂ | D-152 |
| | —O(CH₂)₄—CH-CH₂ (epoxide) | D-153 |

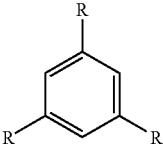

| X = —OC₆H₁₃ | D-154 |
|---|---|
| —OCOC₅H₁₁ | D-155 |
| —OCOOC₄H₉ | D-156 |
| —O(CH₂)₄OCOCH=CH₂ | D-157 |
| —O(CH₂)₆OCOCH=CH₂ | D-158 |
| —OCO(CH₂)₃OCOCH=CH₂ | D-159 |
| —OCO(CH₂)₄OCOCH=CH₂ | D-160 |
| —OCOO(CH₂)₂OCOCH=CH₂ | D-161 |
| —OCOO(CH₂)₄OCOCH=CH₂ | D-162 |
| —O(CH₂)₂OCOC(CH₃)=CH₂ | D-163 |
| —O(CH₂)₂OCOCH=CHCH₃ | D-164 |
| —O(CH₂)₄OCH=CH₂ | D-165 |
| —O(CH₂)₄—CH-CH₂ (epoxide) | D-166 |

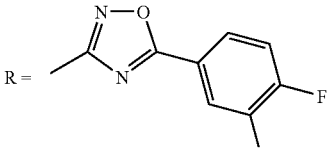 X = —O(CH₂)₄OCOCH=CH₂   D-167

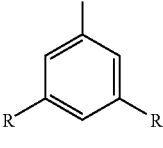 X = —O(CH₂)₄OCOCH=CH₂   D-168

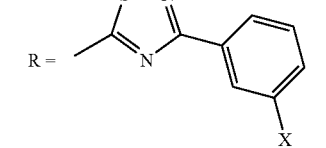 X = —O(CH₂)₄OCOCH=CH₂   D-169

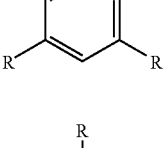 X = —O(CH₂)₄OCOCH=CH₂   D-170

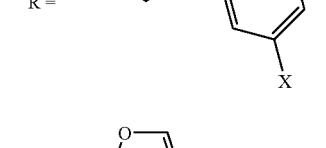 X = —O(CH₂)₄OCOCH=CH₂   D-171

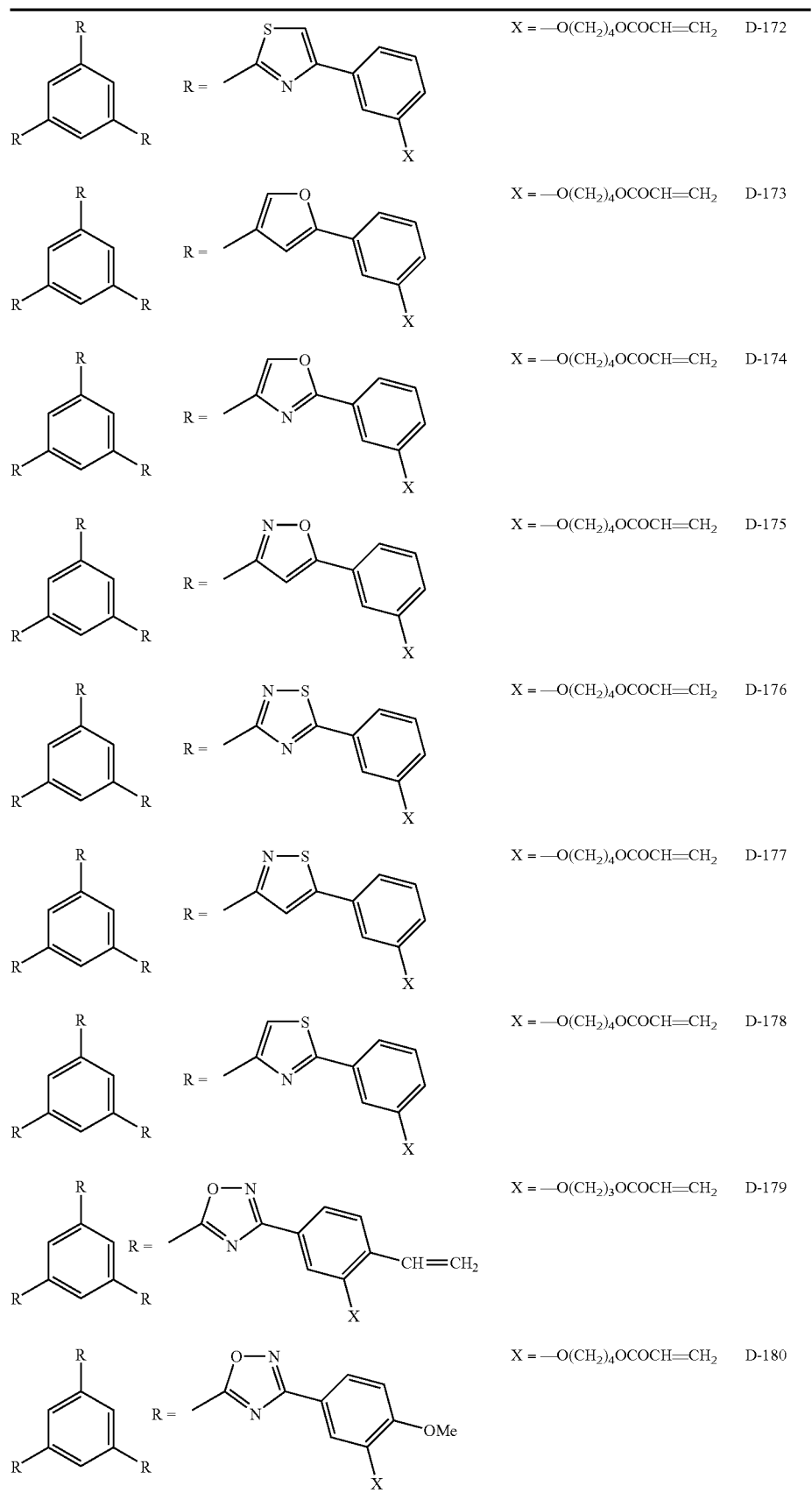

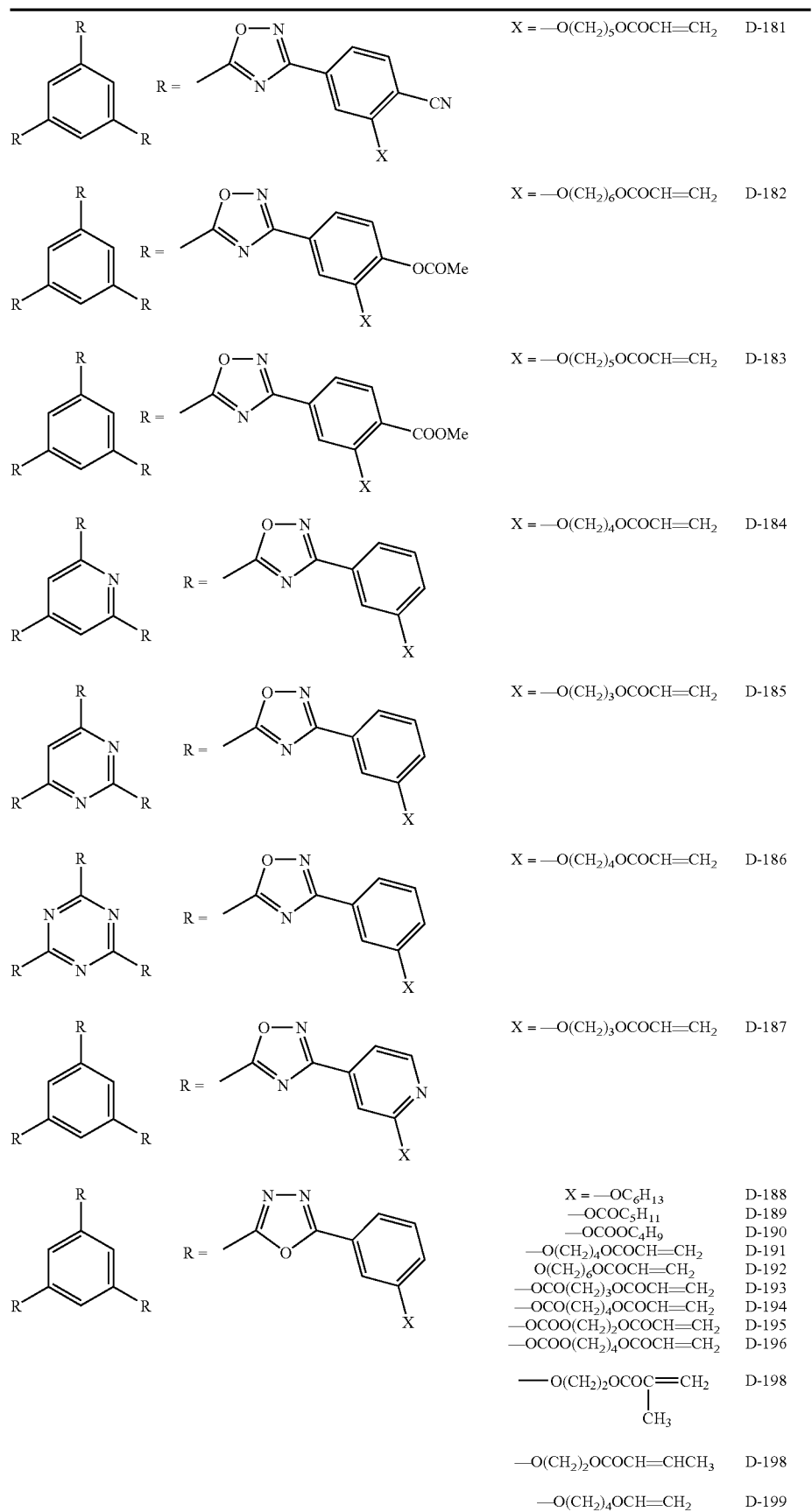

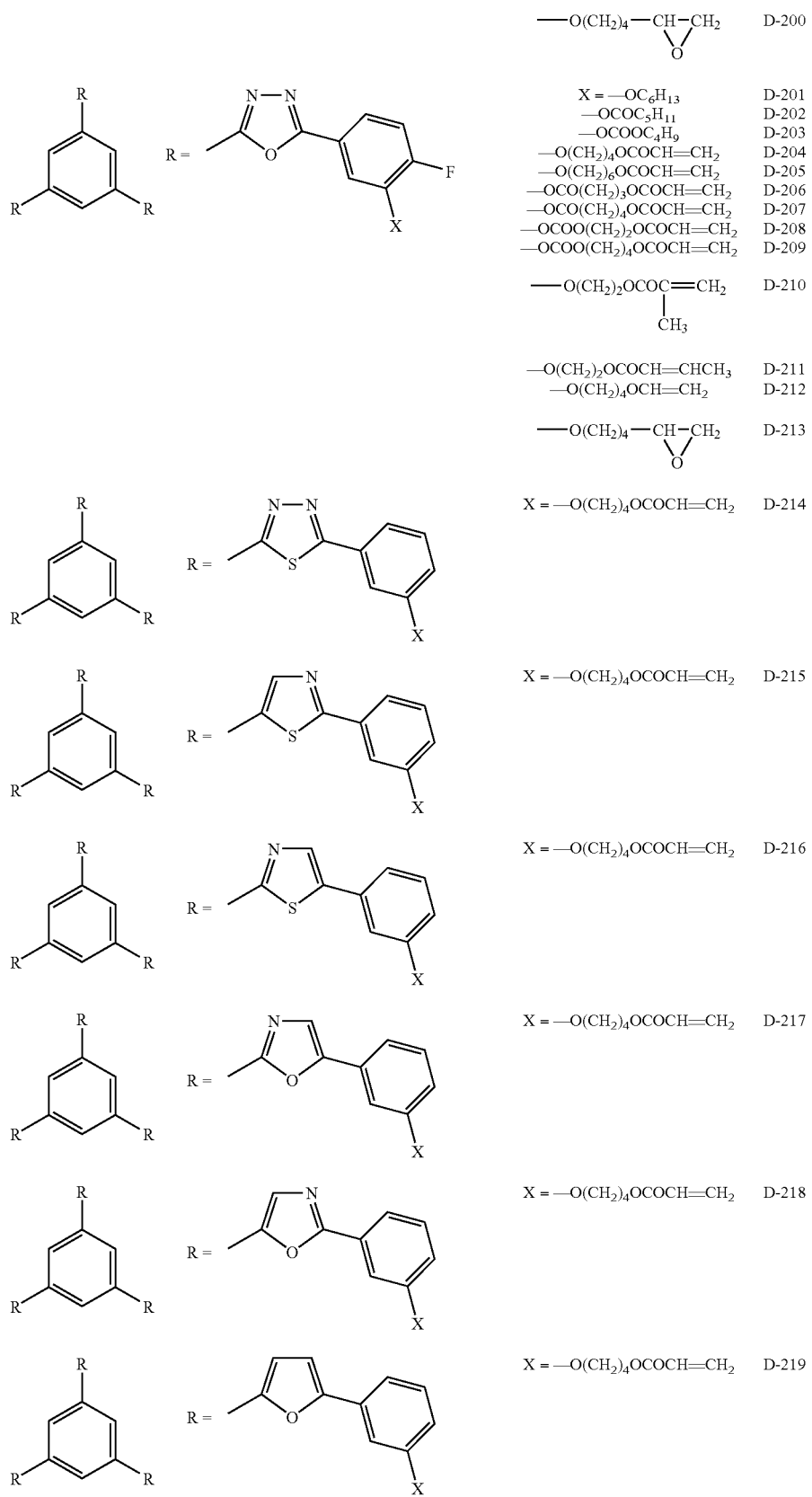

-continued

| Core (R-substituted benzene) | R = | X / substituent | Code |
|---|---|---|---|
| 1,3,5-tri-R-benzene | 2-(3-X-phenyl)thien-5-yl | X = —O(CH$_2$)$_4$OCOCH=CH$_2$ | D-220 |
| 1,3,5-tri-R-benzene | 5-methyl-3-(3-X-phenyl)-1,2,4-oxadiazol-... (O—N / N) | X = —COOC$_4$H$_9$ | D-221 |
| | | —COOC$_5$H$_{11}$ | D-222 |
| | | —COOC$_6$H$_{13}$ | D-223 |
| | | —COO(CH$_2$)$_2$OCOCH=CH$_2$ | D-224 |
| | | —COO(CH$_2$)$_3$OCOCH=CH$_2$ | D-225 |
| | | —COO(CH$_2$)$_4$OCOCH=CH$_2$ | D-226 |
| | | —COO(CH$_2$)$_5$OCOCH=CH$_2$ | D-227 |
| | | —COO(CH$_2$)$_6$OCOCH=CH$_2$ | D-228 |
| | | —COO(CH$_2$)$_7$OCOCH=CH$_2$ | D-229 |
| | | —COO(CH$_2$)$_8$OCOCH=CH$_2$ | D-230 |
| | | —COO(CH$_2$CH$_2$O)$_2$COCH=CH$_2$ | D-231 |
| | | —COO(CH$_2$)$_2$CH(CH$_3$)OCOCH=CH$_2$ | D-232 |
| | | —COO(CH$_2$)$_3$CH(CH$_3$)OCOCH=CH$_2$ | D-233 |
| | | —COO(CH$_2$)$_4$CH(CH$_3$)OCOCH=CH$_2$ | D-234 |
| | | —COOCH$_2$CH(CH$_3$)CH$_2$OCOCH=CH$_2$ | D-235 |
| | | —COO(CH$_2$)$_2$CH(CH$_3$)(CH$_2$)$_2$OCOCH=CH$_2$ | D-236 |
| | | —COOCH(CH$_3$)(CH$_2$)$_2$OCOCH=CH$_2$ | D-237 |
| | | —COO(CH$_2$)$_5$OCOC(CH$_3$)=CH$_2$ | D-238 |
| | | —COO(CH$_2$)$_4$OCH=CH$_2$ | D-239 |
| | | —COO(CH$_2$)$_4$—CH(—O—)CH$_2$ (epoxide) | D-240 |
| 1,3,5-tri-R-benzene | 3-methyl-5-(3-X-phenyl)-1,2,4-oxadiazol-... (N—O / N) | X = —COOC$_4$H$_9$ | D-241 |
| | | —COOC$_5$H$_{11}$ | D-242 |
| | | —COOC$_6$H$_{13}$ | D-243 |
| | | —COO(CH$_2$)$_2$OCOCH=CH$_2$ | D-244 |
| | | —COO(CH$_2$)$_3$OCOCH=CH$_2$ | D-245 |
| | | —COO(CH$_2$)$_4$OCOCH=CH$_2$ | D-246 |
| | | —COO(CH$_2$)$_5$OCOCH=CH$_2$ | D-247 |
| | | —COO(CH$_2$)$_6$OCOCH=CH$_2$ | D-248 |
| | | —COO(CH$_2$)$_7$OCOCH=CH$_2$ | D-249 |
| | | —COO(CH$_2$)$_8$OCOCH=CH$_2$ | D-250 |
| | | —COO(CH$_2$CH$_2$O)$_2$COCH=CH$_2$ | D-251 |
| | | —COO(CH$_2$)$_2$CH(CH$_3$)OCOCH=CH$_2$ | D-252 |
| | | —COO(CH$_2$)$_3$CH(CH$_3$)OCOCH=CH$_2$ | D-253 |
| | | —COO(CH$_2$)$_4$CH(CH$_3$)OCOCH=CH$_2$ | D-254 |
| | | —COOCH$_2$CH(CH$_3$)CH$_2$OCOCH=CH$_2$ | D-255 |
| | | —COO(CH$_2$)$_2$CH(CH$_3$)(CH$_2$)$_2$OCOCH=CH$_2$ | D-256 |
| | | —COOCH(CH$_3$)(CH$_2$)$_2$OCOCH=CH$_2$ | D-257 |
| | | —COO(CH$_2$)$_5$OCOC(CH$_3$)=CH$_2$ | D-258 |
| | | —COO(CH$_2$)$_4$OCH=CH$_2$ | D-259 |
| | | —COO(CH$_2$)$_4$—CH(—O—)CH$_2$ (epoxide) | D-260 |

-continued

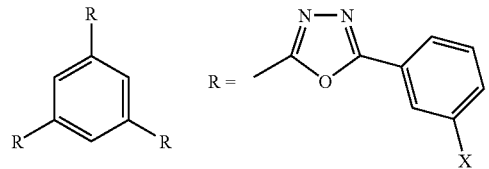

| | |
|---|---|
| X = —COOC$_4$H$_9$ | D-261 |
| —COOC$_5$H$_{11}$ | D-262 |
| —COOC$_6$H$_{13}$ | D-263 |
| —COO(CH$_2$)$_2$OCOCH=CH$_2$ | D-264 |
| —COO(CH$_2$)$_3$OCOCH=CH$_2$ | D-265 |
| —COO(CH$_2$)$_4$OCOCH=CH$_2$ | D-266 |
| —COO(CH$_2$)$_5$OCOCH=CH$_2$ | D-267 |
| —COO(CH$_2$)$_6$OCOCH=CH$_2$ | D-268 |
| —COO(CH$_2$)$_7$OCOCH=CH$_2$ | D-269 |
| —COO(CH$_2$)$_8$OCOCH=CH$_2$ | D-270 |
| —COO(CH$_2$CH$_2$O)$_2$COCH=CH$_2$ | D-271 |
| —COO(CH$_2$)$_2$CH(CH$_3$)OCOCH=CH$_2$ | D-272 |
| —COO(CH$_2$)$_3$CH(CH$_3$)OCOCH=CH$_2$ | D-273 |
| —COO(CH$_2$)$_4$CH(CH$_3$)OCOCH=CH$_2$ | D-274 |
| —COOCH$_2$CH(CH$_3$)CH$_2$OCOCH=CH$_2$ | D-275 |
| —COO(CH$_2$)$_2$CH(CH$_3$)(CH$_2$)$_2$OCOCH=CH$_2$ | D-276 |
| —COOCH(CH$_3$)(CH$_2$)$_2$OCOCH=CH$_2$ | D-277 |

—COO(CH$_2$)$_5$OCOC(CH$_3$)=CH$_2$    D-278

—COO(CH$_2$)$_4$OCH=CH$_2$    D-279

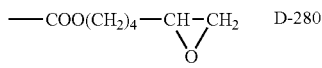
—COO(CH$_2$)$_4$—CH—CH$_2$ (epoxide)    D-280

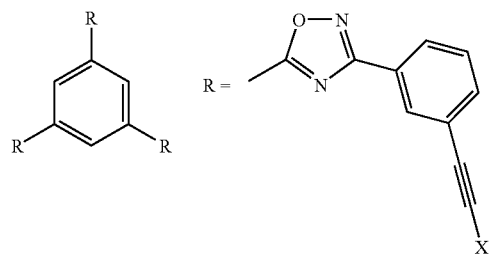

| | |
|---|---|
| X = —C$_4$H$_9$ | D-281 |
| —C$_5$H$_{11}$ | D-282 |
| —C$_6$H$_{13}$ | D-283 |
| —CH$_2$CH(CH$_3$)C$_4$H$_9$ | D-284 |
| —O(CH$_2$)$_2$OCOCH=CH$_2$ | D-285 |
| —(CH$_2$)$_3$OCOCH=CH$_2$ | D-286 |
| —(CH$_2$)$_4$OCOCH=CH$_2$ | D-287 |
| —(CH$_2$)$_5$OCOCH=CH$_2$ | D-289 |
| —(CH$_2$)$_2$CH(CH$_3$)OCOCH=CH$_2$ | D-290 |

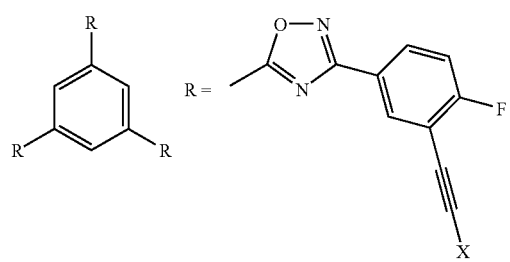

—(CH$_2$)$_3$OCOCH=CH$_2$    D-291

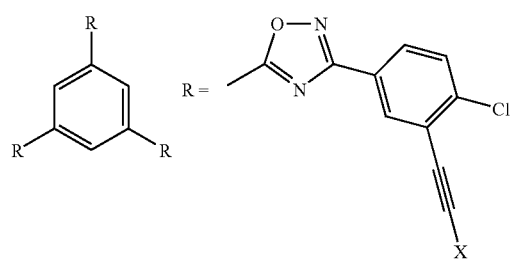

—(CH$_2$)$_3$OCOCH=CH$_2$    D-292

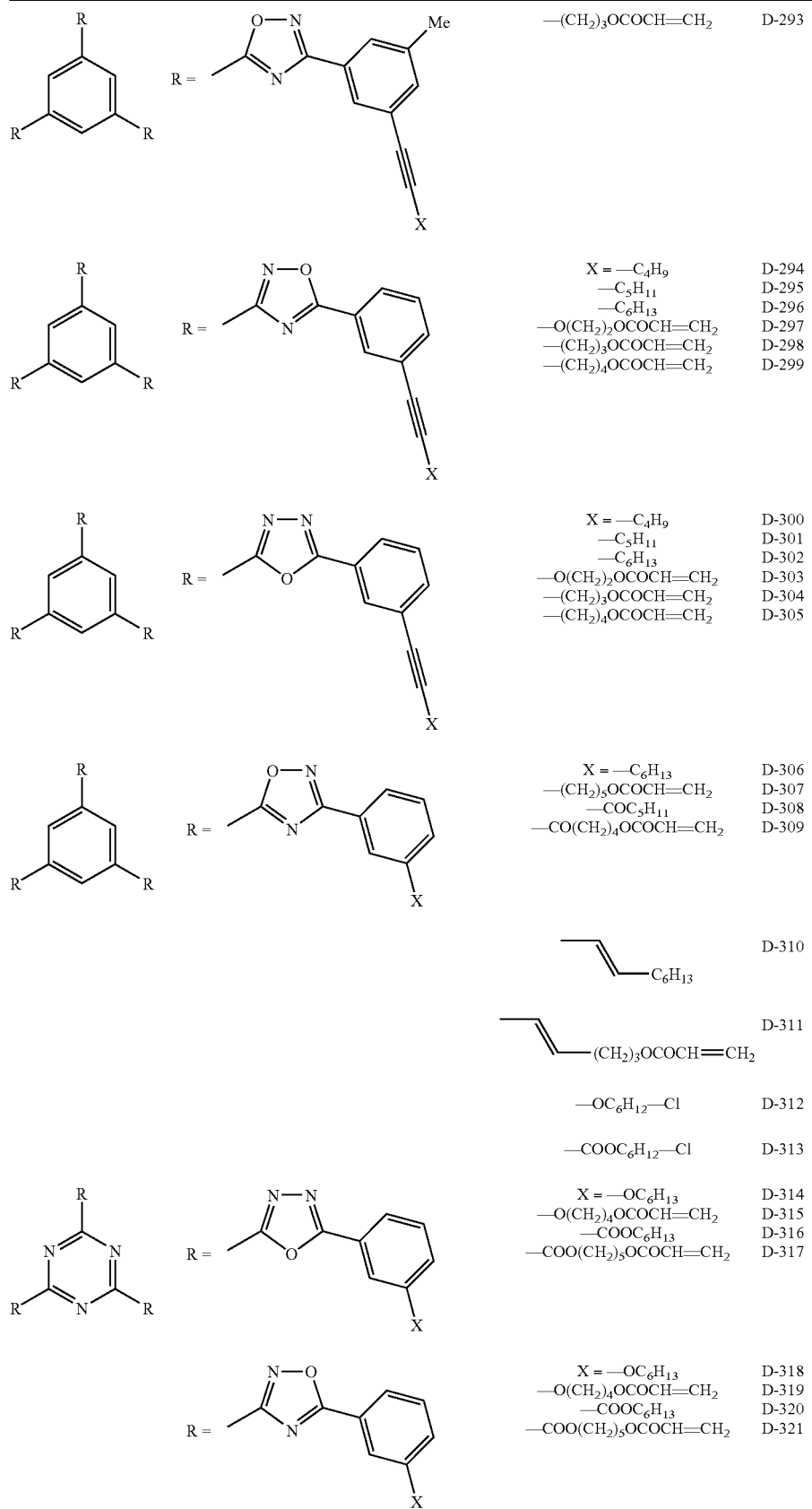

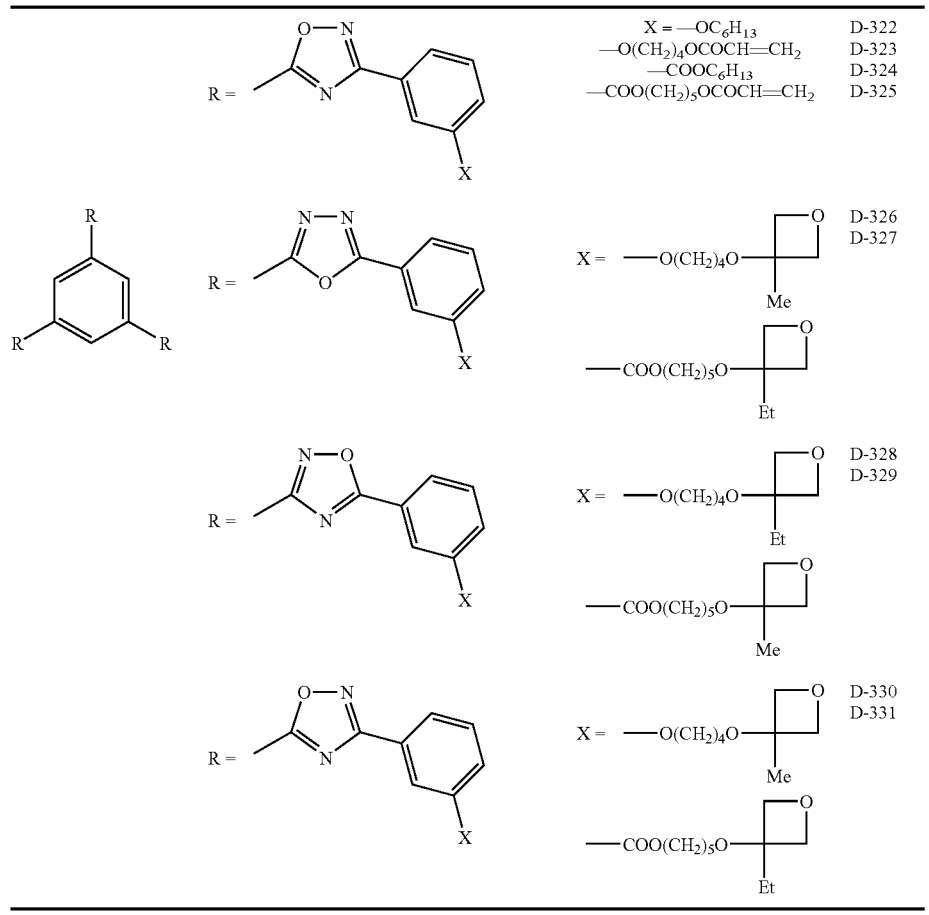

All the compounds of the invention may be produced according to known production methods. In the compounds of the invention, the construction of the 5-membered cyclic group is a matter of importance in their production. For example, a compound of the invention having a 1,3,4-oxadiazole skeleton may be produced, for example, according to a process mentioned below.

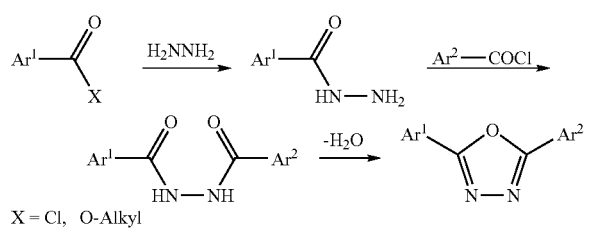

For example, a compound of the invention having a 1,2,4-oxadiazole skeleton may be produced, for example, according to a process mentioned below.

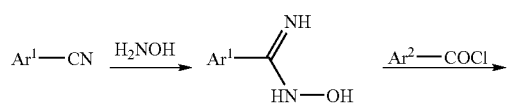

Many of the carboxylic acid analogue compound or the nitrile compound used as the starting material are easily available. However, if hardly available, they may be produced through conversion from their precursors according to ordinary methods. For example, they may be derived from the following precursors.

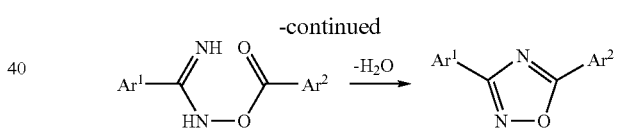

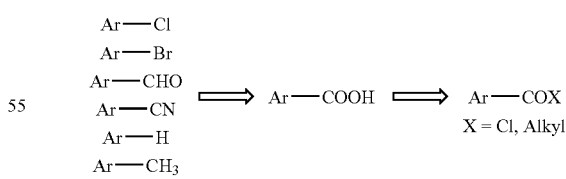

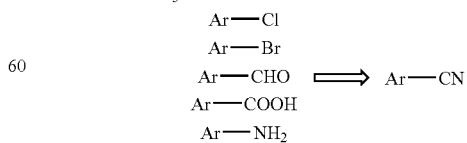

For construction of other 5-membered cyclic groups and for formation of other functional groups than 5-membered cyclic groups, for example, referred to is RODD'S CHEM- ISTRY OF CARBON COMPOUNDS SECOND EDITION; ELSEVIER SCIENTIFIC PUBLISHING COMPANY.

Preferably, the compound of the invention expresses liquid-crystallinity. The liquid-crystal phase which the compound may express is, for example, a columnar phase and a discotic nematic phase ($N_D$ phase). Of those liquid-crystal phases, preferred is a discotic nematic phase ($N_D$ phase) having a good monodomain property.

Preferably, the compound of the invention expresses a liquid-crystal phase at a temperature falling within a range of from 20° C. to 300° C., more preferably from 40° C. to 280° C., even more preferably from 60° C. to 250° C. Expressing a liquid-crystal phase at 20° C. to 300° C., as referred to herein, includes a case where the liquid-crystal temperature range covers 20° C. and around it (for example, from 10° C. to 22° C.), and a case where it covers 300° C. and around it (for example, 298° C. to 310° C.); and the same shall apply to the others of expressing a liquid-crystal phase at 40° C. to 280° C., and at 60° C. to 250° C.

(Retardation Plate)
Optically-Anisotropic Layer:

The compound of formula (DII) to form the optically-anisotropic layer of the retardation plate of the invention is described in detail.

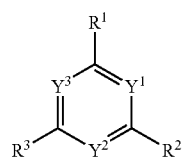

(DII)

In formula (DII), $Y^1$, $Y^2$ and $Y^3$ have the same meanings as $Y^{11}$, $Y^{12}$ and $Y^{13}$ in formula (DI), and their preferred ranges are the same as those of the latter.

$R^1$, $R^2$ and $R^3$ each independently represent a group of the following formula (DII-H). Preferably, $R^1=R^2=R^3$.

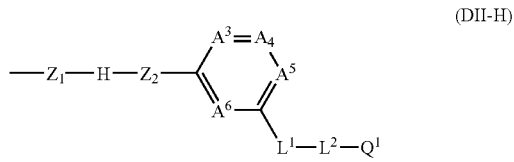

(DII-H)

In formula (DII-H), $Z^1$ and $Z^2$ each independently represent a single bond or a divalent linking group. When $Z^1$ and $Z^2$ represent a divalent linking group, it is desirable that they independently represent a divalent linking group selected from the group consisting of —O—, —S—, —C(=O)—, —SO—, —SO$_2$—, —NR$^7$—, —CH=CH—, —C≡C—, a divalent cyclic group and their combinations. $R^7$ represents an alkyl group having from 1 to 7 carbon atoms, or a hydrogen atom, preferably an alkyl group having from 1 to 4 carbon atoms, or a hydrogen atom, more preferably a methyl group, an ethyl group or a hydrogen atom, most preferably a hydrogen atom.

The divalent cyclic group for $Z^1$ and $Z^2$ is a divalent linking group having at least one cyclic structure. The ring in the divalent cyclic group is preferably a 5-membered ring, a 6-membered ring or a 7-membered ring, more preferably a 5-membered ring or a 6-membered ring, most preferably a 6-membered ring. The ring in the cyclic group may be a condensed ring. For it, however, a monocyclic ring is preferred to a condensed ring. The ring to be contained in the cyclic group may be any of an aromatic ring, an aliphatic ring or a heterocyclic ring. Examples of the aromatic ring include a benzene ring and a naphthalene ring. Examples of the aliphatic ring include a cyclohexane ring. Examples of the heterocyclic ring include a pyridine ring and a pyrimidine ring. For the cyclic group, preferred are an aromatic ring and a heterocyclic ring.

Of the divalent cyclic group for $Z^1$ and $Z^2$, the cyclic group having a benzene ring is preferably a 1,4-phenylene group. The cyclic group having a naphthalene ring is preferably a naphthalene-1,5-diyl or naphthalene-2,6-diyl group. The cyclic group having a cyclohexane ring is preferably a 1,4-cyclohexylene group. The cyclic group having a pyridine ring is preferably a pyridine-2,5-diyl group. The cyclic group having a pyrimidine ring is preferably a pyrimidine-2,5-diyl group.

The divalent cyclic group for $Z^1$ and $Z^2$ may have a substituent. Examples of the substituent include a halogen atom, a cyano group, a nitro group, an alkyl group having from 1 to 16 carbon atoms, a halogen-substituted alkyl group having from 1 to 16 carbon atoms, an alkoxy group having from 1 to 16 carbon atoms, an acyl group having from 2 to 16 carbon atoms, an alkylthio group having from 1 to 16 carbon atoms, an acyloxy group having from 2 to 16 carbon atoms, an alkoxycarbonyl group having from 2 to 16 carbon atoms, a carbamoyl group, an alkyl-substituted carbamoyl group having from 2 to 16 carbon atoms, and an acylamino group having from 2 to 16 carbon atoms.

Preferably, $Z^1$ and $Z^2$ represent a single bond, —O—CO—, —CO—O—, —CH=CH—, —C≡C—, -divalent cyclic group-, —O—CO-divalent cyclic group-, —CO—O-divalent cyclic group-, —CH=CH-divalent cyclic group, —C≡C-divalent cyclic group-, -divalent cyclic group-O—CO—, -divalent cyclic group-CO—O—, -divalent cyclic group-CH=CH—, or -divalent cyclic group-C≡C—; more preferably a single bond, —CH=CH—, —C≡C—, —CH=CH-divalent cyclic group-, or —C≡C-divalent cyclic group.

H in formula (DII-H) each independently represents a divalent 5-membered cyclic group.

The divalent 5-membered cyclic group is preferably a hetero ring. The hetero atom includes, for example, an oxygen atom, a nitrogen atom, a sulfur atom, a boron atom, a phosphorus atom. Especially preferred are an oxygen atom, a nitrogen atom, and a sulfur atom. More preferred is a hetero ring containing a nitrogen atom and an oxygen atom.

Preferably, the divalent 5-membered cyclic group has at least one methine group, more preferably two methine groups. Also preferably, the hydrogen atom of the methine group is substituted with $Z^1$ or $Z^2$.

The divalent 5-membered cyclic group includes, for example, a thiophene-2,5-diyl group, a furan-2,5-diyl group, an oxazole-2,5-diyl group, an imidazole-2,5-diyl group, a 1,3,4-oxadiazole-2,5-diyl group, a 1,2,4-oxadiazole-2,5-diyl group, a tetrahydrofuran-2,4-diyl group.

The divalent 5-membered cyclic group may have a substituent. For the substituent, referred to are the same as those for the substituent of $Y^{11}$, $Y^{12}$ and $Y^{13}$.

$A^3$, $A^4$, $A^5$ and $A^6$ in formula (DII-A) have the same meanings as $A^{13}$, $A^{14}$, $A^{15}$ and $A^{16}$ in formula (DI-A), and their preferred ranges are also the same as those of the latter.

$L^1$ in formula (DII-A) has the same meanings as $L^{11}$ in formula (DI-A), and its preferred range is also the same as that of the latter.

$L^2$ in formula (DII-A) has the same meanings as $L^{12}$ in formula (DI-A), and its preferred range is also the same as that of the latter.

$Q^1$ in formula (DII-A) has the same meanings as $Q^{11}$ in formula (DI-A), and its preferred range is also the same as that of the latter.

More preferably, the compound of formula (DII), which is to form the optically-anisotropic layer of the retardation plate of the invention, is a compound of formula (DI).

Preferably, the compound of formula (DII) is uniformly aligned in the optically-anisotropic layer of the retardation plate of the invention. For obtaining the uniformly-aligned thin film, for example, any other additive is optionally added to the liquid-crystalline compound to prepare a liquid-crystalline composition, then the liquid-crystalline composition is applied onto a substrate, and the coating layer is uniformly aligned in its liquid-crystalline state. Examples of the additives that may be added to the liquid-crystalline compound are an air interface alignment-controlling agent, a repelling inhibitor, a polymerization initiator and a polymerizable monomer, which are described hereinunder.

The alignment state of the compound of the invention is preferably a homeotropic alignment, a hybrid alignment and a vertical alignment.

The thickness of the thin film in which the molecules of the liquid-crystalline composition of the invention are uniformly aligned is preferably from 0.2 to 10.0 μm, more preferably from 0.4 to 4.0 μm.

For realizing the uniformly-aligned state, it is desirable to provide an alignment film. However, when the optical axis direction of discotic liquid-crystalline compounds is the same as the normal line direction of the thin film plane (in homeotropic alignment), then the alignment film is not always necessary.

The alignment film may be provided by various methods of rubbing treatment of an organic compound (preferably, polymer), or oblique deposition of an inorganic compound, or formation of a layer having microgrooves, or a Langmuir-Blodgett process of building up an organic compound (e.g., ω-tricosanoic acid, methyl stearate) (LB film). Further, there are known other various alignment films capable of expressing an alignment function through exposure to an electric field or a magnetic field or exposure to light.

The alignment film may have any layer so far as it may impart an intended alignment to the liquid-crystalline composition of the invention. In the invention, preferred is an alignment film formed through rubbing treatment or exposure to light. More preferred is an alignment film formed through rubbing treatment of polymer. The rubbing treatment may be attained generally by rubbing a few times the surface of a polymer layer with paper or cloth in a predetermined direction. Preferably in the invention, the treatment is attained according to the methods described in *Handbook of Liquid Crystals* (by Maruzen). Preferably, the thickness of the alignment film is from 0.01 to 10 μm, more preferably from 0.05 to 3 μm.

A fixed alignment state as referred to herein means a state where the alignment is fixed and kept as such as the most typical and preferred embodiment thereof, to which, however, the invention should not be limited. For example, the fixed alignment state further includes any other state where the fixed liquid-crystalline composition is not fluid generally within a temperature range of from 0° C. to 50° C., but even under a severe condition within a temperature range of from −30° C. to 70° C., and where the alignment condition is not changed by any external field or any external force and therefore the alignment condition can be kept stable as such. When an optically-anisotropic layer where the alignment state has been finally fixed is formed, then the liquid-crystalline composition of the invention may no more exhibit liquid-crystallinity. For example, since a polymerizable group-having compound is used as the liquid-crystalline compound, it may after all polymerize or crosslink through exposure to heat or light to form a polymer compound and the resulting polymer compound may lose liquid-crystallinity.

In forming such an optically-anisotropic layer, some additive may be added to the liquid-crystalline composition of the invention. Examples of the additive are an air interface alignment-controlling agent, a repelling inhibitor, a polymerization initiator and a polymerizable monomer.

[Air Interface Alignment-Controlling Agent]

Homeotropic alignment, hybrid alignment and vertical alignment may be realized by selecting the additive to be localized in air interface and the type of the alignment film.

For realizing the alignment state, an external field such as an electric field or a magnetic field may be employed, or an additive to be localized in air interface may be used. Preferably, an additive is used. As the additive, preferred is a compound having, in the molecule, at least one group of a substituted or unsubstituted aliphatic group having from 6 to 40 carbon atoms or a substituted or unsubstituted aliphatic-substituted oligosiloxanoxy group having from 6 to 40 carbon atoms, and more preferred is a compound having at least two such groups in the molecule. For example, for the air interface alignment-controlling agent, usable are those described in JP-A 11-352328 and 2002-20363.

The amount of the air interface alignment-controlling agent to be added to the liquid-crystalline composition of the invention is preferably from 0.001% by mass to 20% by mass, more preferably from 0.01% by mass to 10% by mass, most preferably from 0.1% by mass to 5% by mass of the composition.

[Repelling Inhibitor]

The liquid-crystalline composition of the invention may contain a repelling inhibitor, which is for preventing the composition from being repelled by the substrate coated with the composition. In general, a polymer compound is preferred for the repelling inhibitor.

Not specifically defined, the polymer usable for the purpose may be any one not extremely interfering with the tile angle change or the alignment of the molecules of the liquid-crystalline composition of the invention.

Examples of the polymer are described in JP-A 8-95030. Especially preferred examples of the polymer are cellulose esters. Examples of the cellulose esters are cellulose acetate, cellulose acetate propionate, hydroxypropyl cellulose and cellulose acetate butyrate.

The amount of the polymer used for repelling prevention to be added so as not to interfere with the alignment of the molecules of the liquid-crystalline composition of the invention is preferably from 0.1 to 10% by mass, more preferably from 0.1 to 8% by mass, even more preferably from 0.1 to 5% by mass of the composition.

Surfactant may also be used herein. The surfactant may be any known compound, but is preferably a fluorine compound. Concretely, for example, herein usable are those described in JP-A 2001-330725, paragraphs [0028] to [0056]; and those described in JP-A 2005-179636, paragraphs [0100] to [0118]. The amount of the surfactant that may be in the composition of the invention may be generally from 0.005 to 8% by mass, but preferably from 0.05 to 2.5% by mass of the discotic compound therein.

[Polymerization Initiator]

For fixing the alignment state of liquid-crystalline molecules in the invention, employable is a method comprising once heating the liquid-crystalline composition up to the liquid-crystal phase-forming temperature thereof and then cooling it while keeping the alignment state whereby the composition is fixed as such not detracting from the alignment state in that liquid-crystal condition. A polymerization initiator may be added to the liquid-crystalline composition of the invention, and the resulting composition may be heated up to the liquid-crystal phase-forming temperature thereof, then polymerized and cooled whereby the alignment state of the liquid-crystal phase of the composition may be fixed as such. Preferably, the alignment state in the invention is fixed according to the latter polymerization method. The polymerization includes thermal polymerization with a thermal polymerization initiator, photopolymerization with a photopolymerization initiator, and polymerization through exposure to electron rays. For preventing the support from being deformed or deteriorated by heat, preferred is photopolymerization or polymerization through exposure to electron rays.

Examples of the photopolymerization initiator are α-carbonyl compounds (as in U.S. Pat. Nos. 2,367,661, 2,367,670), acyloin ethers (as in U.S. Pat. No. 2,448,828), α-hydrocarbon-substituted aromatic acyloin compounds (as in U.S. Pat. No. 2,722,512), polycyclic quinone compounds (as in U.S. Pat. Nos. 3,046,127, 2,951,758), combination of triarylimidazole dimer and p-aminophenylketone (as in U.S. Pat. No. 3,549,367), acridine and phenazine compounds (as in JP-A 60-105667, U.S. Pat. No. 4,239,850), and oxadiazole compounds (as in U.S. Pat. No. 4,212,970).

The amount of the photopolymerization initiator to be used is preferably from 0.01 to 20% by mass, more preferably from 0.5 to 5% by mass of the solid content of the coating liquid for the optically-anisotropic layer.

For light irradiation for polymerization, preferably employed are UV rays. The irradiation energy is preferably from 10 mJ to 50 J/cm$^2$, more preferably from 50 mJ to 800 mJ/cm$^2$. For promoting the photopolymerization reaction, the light irradiation may be attained under heat. The oxygen concentration in the polymerization atmosphere may have some influence on the degree of polymerization. Therefore, when the desired degree of polymerization could not be obtained in polymerization in air, then it is desirable that the oxygen concentration in the polymerization atmosphere is lowered through nitrogen purging or the like. Preferably, the oxygen concentration in the polymerization atmosphere is at most 10%, more preferably at most 7%, most preferably at most 3%.

[Polymerizable Monomer]

A polymerizable monomer may be added to the liquid-crystalline composition of the invention. Not specifically defined, the polymerizable monomer usable in the invention may be any one that is miscible with the compound of the invention and does not significantly detract from the alignment of the liquid-crystalline composition of the invention. For the monomer, for example, preferred are compound having a polymerization-active ethylenic unsaturated group, such as a vinyl group, a vinyloxy group, an acryloyl group or a methacryloyl group. Preferably, the amount of the polymerizable monomer to be added to the composition is from 0.5 to 50% by mass, more preferably from 1 to 30% by mass of the liquid-crystalline compound in the composition. Monomers having at least two reactive functional groups are especially preferably used herein, as they may be effective for increasing the adhesiveness between the alignment film and the optically-anisotropic layer.

[Coating Solvent]

An organic solvent is preferably used in preparing the liquid-crystalline composition of the invention. Examples of the organic solvent are amides (e.g., N,N-dimethylformamide), sulfoxides (e.g., dimethylsulfoxide), heterocyclic compounds (e.g., pyridine), hydrocarbons (e.g., toluene, hexane), alkyl halides (e.g., chloroform, dichloromethane), esters (e.g., methyl acetate, butyl acetate), ketones (e.g., acetone, methyl ethyl ketone, methyl isobutyl ketone, cyclohexanone), ethers (e.g., tetrahydrofuran, 1,2-dimethoxyethane). Preferred are alkyl halides, esters and ketones. Two or more such organic solvents may be used as combined.

[Coating Method]

The thin film of the invention may be formed by preparing a coating liquid of the liquid-crystalline composition of the invention by the use of the above-mentioned solvent, applying the coating liquid onto an alignment film, and aligning the liquid-crystalline composition of the invention. The coating liquid may be applied in any known method (for example, spin-coating method, wire bar-coating method, extrusion-coating method, direct gravure-coating method, reverse gravure-coating method, die-coating method).

The retardation plate of the invention has an optically-anisotropic layer formed of the liquid-crystalline composition of the invention, on a transparent support thereof.

Combined with a polarizing film, the retardation plate of the invention may be used as an elliptically-polarizing plate. In addition, when used in a transmission-type, a reflection-type or a semitransmission-type liquid-crystal display device also as combined with a polarizing film, then the retardation plate may be effective for enlarging the viewing angle of the device.

[Transparent Support]

Not specifically defined, the material of the transparent support of the retardation plate of the invention may be any one that is essentially optically isotropic and has a light transmittance of at least 80%. For the material, preferred is a polymer film or glass.

Examples of the polymer are films of cellulose acylates (e.g., cellulose diacetate, cellulose triacetate), norbornene polymers, poly(meth)acrylate esters, and many commercially-available polymers may be favorably used herein. Of those, preferred are cellulose esters from the viewpoint of the optical properties thereof, and more preferred are lower fatty acid esters of cellulose. The lower fatty acids are preferably those having at most 6 carbon atoms. The number of the carbon atoms constituting the acids is preferably 2 (e.g., cellulose acetate), 3 (e.g., cellulose propionate) or 4 (e.g., cellulose butyrate). Especially preferred is cellulose triacetate. Mixed fatty acid esters such as cellulose acetate propionate and cellulose acetate butyrate are also usable herein. In addition, polymers capable of readily expressing birefringence such as conventional polycarbonates and polysulfones, as well as polymers of which the ability to express birefringence has been lowered through molecular modification, such as those described in a pamphlet of WO00/26705, are also usable herein.

Cellulose acylate (especially cellulose triacetate) favorably usable as the transparent support is described in detail hereinunder.

Cellulose acylate for use herein preferably has a degree of acetylation of from 55.0 to 62.5%, more preferably from 57.0 to 62.0%. The degree of acetylation means the overall amount of bonding acid amount per the cellulose unit mass. The degree of acetylation may be determined and calculated according to ASTM:D-817-91 (test method for cellulose acetate). Preferably, the viscosity-average degree of polymerization (DP) of the cellulose ester for use herein is at least 250, more preferably at least 290. Also preferably, the molecular weight distribution in terms of Mw/Mn (Mw is a mass-average molecular weight, and Mn is a number-average molecular weight) through gel permeation chromatography of the cellulose ester for use in the invention is narrow. Concretely, Mw/Mn of the cellulose ester is preferably from 1.0 to 1.7, more preferably from 1.3 to 1.65, most preferably from 1.4 to 1.6.

In cellulose acylate, the overall degree of substitution is not always distributed to ⅓ uniformly for the 2-, 3- and 6-positioned hydroxyl groups of cellulose, but the degree of substitution at the 6-positioned hydroxyl group tends to be small. In the invention, the degree of substitution at the 6-positioned hydroxyl group of cellulose is preferably as larger as possible than that at the 2- and 3-positioned hydroxyl groups. Preferably, the 6-positioned hydroxyl group is substituted with an acyl group to a degree of from 30 to 40% of the overall degree of substitution, more preferably from 31 to 40%, even more preferably from 32 to 40%. Preferably, the degree of substitution at 6-position is at least 0.88. The 6-positioned hydroxyl group may be substituted with any other acyl group having 3 or more carbon atoms (e.g., propionyl group, butyryl group, valeroyl group, benzoyl group, acryloyl group) than an acetyl group. The degree of substitution at each position may be determined through NMR. Cellulose esters having a high degree of substitution at the 6-positioned hydroxyl group may be produced with reference to Production Example 1 in paragraphs [0043] to [0044], Production Example 2 in paragraphs [0048] to [0049] and Production Example 3 in paragraphs [0051] to [0052] in JP-A 11-5851.

The polymer film, especially the cellulose acylate film for the transparent support may contain an aromatic compound having at least two aromatic rings as a retardation-increasing agent for controlling the retardation of the film. The amount of the retardation-increasing agent, if used in the film, is preferably from 0.01 to 20 parts by mass, more preferably from 0.05 to 15 parts by mass, even more preferably from 0.1 to 10 parts by mass relative to 100 parts by mass of the cellulose acylate for the film. Two or more such aromatic compounds may be combined for use herein.

The aromatic ring of the aromatic compound includes an aromatic hetero ring in addition to an aromatic hydrocarbon ring.

The aromatic hydrocarbon ring is preferably a 6-membered ring (that is, benzene ring).

The aromatic hetero ring is generally an unsaturated hetero ring. The aromatic hetero ring is preferably a 5-membered, 6-membered or 7-membered ring, more preferably a 5-membered or 6-membered ring. The aromatic hetero ring generally has a largest number of double bonds. The hetero atom is preferably a nitrogen atom, an oxygen atom and a sulfur atom, more preferably a nitrogen atom.

The aromatic ring is preferably a benzene ring, a furan ring, a thiophene ring, a pyrrole ring, an oxazole ring, a thiazole ring, an imidazole ring, a triazole ring, a pyridine ring, a pyrimidine ring, a pyrazine ring and a 1,3,5-triazine ring, more preferably a benzene ring and a 1,3,5-triazine ring. Especially preferably, the aromatic compound has at least one 1,3,5-triazine ring.

Examples of the aromatic hetero ring include a furan ring, a thiophene ring, a pyrrole ring, an oxazole ring, an isoxazole ring, a thiazole ring, an isothiazole ring, an imidazole ring, a pyrazole ring, a furazane ring, a triazole ring, a pyran ring, a pyridine ring, a pyridazine ring, a pyrimidine ring, a pyrazine ring and a 1,3,5-triazine ring.

Preferably, the number of the aromatic rings constituting the aromatic compound is from 2 to 20, more preferably from 2 to 12, even more preferably from 2 to 8, most preferably from 2 to 6. The bonding mode of two aromatic rings may be grouped into (a) a case of forming a condensed ring, (b) a case where the rings bond to each other via a single bond, and (c) a case where the rings bond to each other via a linking group (aromatic rings could not form spiro-bonding). The bonding mode in the invention may be any of these (a) to (c). The retardation-increasing agent of the type is described, for example, in a pamphlet of WO01/88574A1, a pamphlet of WO00/2619A1, and JP-A 2000-111914, 2000-275434, 2002-363343.

The cellulose acylate film is preferably produced from a prepared cellulose acylate solution (dope) according to a solution casting method. The above-mentioned retardation-increasing agent may be added to the dope.

The dope is cast onto a drum or a band, on which the solvent is evaporated away to form a film. Before cast, the concentration of the dope is preferably so controlled that the solid content thereof could be from 18 to 35% by mass. Preferably, the surface of the drum or the band is finished to a mirror condition. The casting and drying method for the solution casting method is described, for example, in U.S. Pat. Nos. 2,336,310, 2,367,603, 2,492,078, 2,492,977, 2,492,978, 2,607,704, 2,739,069, 2,739,070; British Patent Nos. 640, 731, 736,892; JP-B 45-4554, 49-5614; JP-A 60-176834, 60-203430, 62-115035.

Preferably, the dope is cast onto a drum or a band having a surface temperature of 10° C. or lower. After cast onto it, the dope is preferably dried by applying air thereto for 2 seconds or more. Thus formed, the film is peeled away from the drum or the band, and it may be dried in hot air of which the temperature is successively varied from 100° C. to 160° C., so that the remaining solvent could be evaporated away. The method is described in JP-B 5-17844. According to the method, the time to be taken from casting to peeling may be shortened. In carrying out the method, the cast dope must gel at the surface temperature of a drum or band.

Two or more layers may be formed to give a film, by casting the thus-prepared cellulose acylate solution (dope). The dope is cast onto a drum or a band and the solvent is evaporated away to form a film. Before cast, the concentration of the dope is preferably so controlled that the solid content thereof could be from 10 to 40%. Preferably, the surface of the drum or the band is finished to a mirror condition.

When a plurality of cellulose acylate solutions are cast, then cellulose acylate-containing solutions may be cast through plural casting ports disposed at intervals in the support-traveling direction, and they may be laminated to form a film on the support. For example, the method described in JP-A 61-158414, 1-122419, 11-198285 may be employed. Cellulose acylate solutions may be cast through two casting port to form a film. For example, the method described in JP-B 60-27562, JP-A 61-94724, 61-104813, 61-158413, 6-134933 may be employed. In addition, also employable herein is the casting method of forming a cellulose acetate film described in JP-A 56-162617, which comprises co-extruding a high-viscosity cellulose acetate solution and a low-viscosity cellulose acetate solution while enveloping the flow of the high-viscosity cellulose acetate solution in the flow of the low-viscosity cellulose acetate solution.

The cellulose acylate film may be stretched for controlling its retardation. Preferably, the draw ratio in stretching is within a range of from 0 to 100%. When the cellulose acylate film for use in the invention is stretched, a tenter is preferably used. For accurately controlling the slow axis of the film being stretched, it is desirable that the difference in the tenter clip speed and the timing for unclipping between the right and left sides of the film is as small as possible.

A plasticizer may be added to the cellulose acylate film for improving the mechanical properties of the film and for increasing the drying speed in producing the film. Phosphates or carboxylates may be used as the plasticizer. Examples of phosphates are triphenyl phosphate (TPP), diphenylbiphenyl phosphate, and tricresyl phosphate (TCP). Carboxylates are typically phthalates and citrates. Examples of phthalates include dimethyl phthalate (DMP), diethyl phthalate (DEP), dibutyl phthalate (DBP), dioctyl phthalate (DOP), diphenyl phthalate (DPP) and di-2-ethylhexyl phthalate (DEHP). Examples of citrates include triethyl O-acetylcitrate (OACTE) and tributyl O-acetylcitrate (OACTB). Examples of other carboxylates include butyl oleate, methylacetyl ricinoleate, dibutyl sebacate, and various trimellitates. Phthalate plasticizers (DMP, DEP, DBP, DOP, DPP, DEHP) are preferred for use herein. Preferably, the amount of the plasticizer to be added to the film is from 0.1 to 25% by mass, more preferably from 1 to 20% by mass, most preferably from 3 to 15% by mass of the amount of the cellulose ester for the film.

A deterioration inhibitor (e.g., antioxidant, peroxide-decomposing agent, radical inhibitor, metal inactivator, acid scavenger, amine) and a UV inhibitor may be added to the cellulose acylate film. The deterioration inhibitor is described, for example, in JP-A 3-199201, 5-197073, 5-194789, 5-271471, 6-107854. The amount of the deterioration inhibitor that may be in the film is preferably from 0.01 to 1% by mass, more preferably from 0.01 to 0.2% by mass of the solution (dope) for the film. If the amount is smaller than 0.01% by mass, then the deterioration inhibitor will be almost ineffective. When the amount is 1% by mass or less, then the deterioration inhibitor may be more effectively prevented from bleeding out on the surface of the film.

An especially preferred example of the deterioration inhibitor is butylated hydroxytoluene (BHT). The UV inhibitor is described in JP-A 7-11056.

Preferably, the cellulose acylate film is subjected to surface treatment. Concretely, the surface treatment includes corona discharge treatment, glow discharge treatment, flame treatment, acid treatment, alkali treatment, UV irradiation treatment. Providing an undercoat layer is also preferably employed herein, for example, as in JP-A 7-333433.

From the viewpoint of ensuring the surface smoothness of the cellulose acylate film, the temperature of the film during the treatment is preferably not higher than the glass transition temperature (Tg) of the film, concretely not higher than 150° C.

From the viewpoint of the adhesiveness thereof to an alignment film, the surface treatment of the cellulose acylate film is preferably acid treatment or alkali treatment, or that is, saponification of cellulose acylate. An example of alkali saponification is described below. A preferred process of alkali saponification comprises dipping the surface of a film in an alkali solution, then neutralizing it with an acid solution, and thereafter washing it with water and drying it. The alkali solution may be a potassium hydroxide solution or a sodium hydroxide solution. The hydroxide ion concentration in the solution is preferably from 0.1 to 3.0 mol/liter, more preferably from 0.5 to 2.0 mol/liter. The alkali solution temperature is preferably within a range of from room temperature (e.g., 18° C.) to 90° C., more preferably from 40 to 70° C.

Preferably, the surface energy of the cellulose acylate film is at least 55 mN/m, more preferably from 60 to 75 mN/m.

The surface energy may be determined according to a contact angle method, a wet heat method or an adsorption method, for example, as in *Basis and Application of Wetting* (by Realize, issued Dec. 10, 1989). For the cellulose acylate film for use in the invention, a contact angle method is preferred. Concretely, the method is as follows: props of two solutions of which the surface energy are applied to the cellulose acylate film. At the crossing at which the surface of the droplet and the film surface cross each other, the angle formed by a tangential line to the droplet and the film surface and including the droplet is referred to as a contact angle. Based on the contact angle thus measured, the surface energy of the film is calculated.

Preferably, the thickness of the cellulose acylate film is from 5 to 500 μm, more preferably from 20 to 250 μm, even more preferably from 30 to 180 μm, still more preferably from 30 to 110 μm.

[Elliptically-Polarizing Plate]

An elliptically-polarizing plate may be fabricated by laminating the retardation plate of the invention and a polarizing film. Using the retardation plate of the invention provides an elliptically-polarizing plate capable of enlarging the viewing angle of a liquid-crystal display device that comprises the elliptically-polarizing plate.

The polarizing film includes, for example, an iodine-containing polarizing film, a dichroic dye-containing polarizing film, and a polyene-type polarizing film. The iodine-containing polarizing film and the dye-containing polarizing film are generally produced by the use of a polyvinyl alcohol film. The polarization axis of the polarizing film corresponds to a direction perpendicular to the stretching direction of the film.

The polarizing film is laminated on the side of the optically-anisotropic layer of the retardation plate. Preferably, a transparent protective film is formed on the side opposite to the side of the polarizing film coated with the retardation plate. Preferably, the transparent protective film has a light transmittance of at least 80%. For the transparent protective film, preferred is a cellulose ester film, and more preferred is a triacetyl cellulose film. Preferably, the cellulose ester film is formed according to a solution casting method. Preferably, the thickness of the transparent protective film is from 20 to 500 μm, more preferably from 50 to 200 μm.

[Liquid-Crystal Display Device]

Using the retardation plate of the invention provides a liquid-crystal display device having an enlarged viewing angle. A retardation plate (optically-compensatory sheet) for TN-mode liquid-crystal cells is described in JP-A 6-214116, U.S. Pat. Nos. 5,583,679 and 5,646,703, and German Patent No. 3,911,620A1. An optically-compensatory sheet for IPS-mode or FLC-mode liquid-crystal cells is described in JP-A 10-54982. An optically-compensatory sheet for OCB-mode or HAN-mode liquid-crystal cells is described in U.S. Pat. No. 5,805,253 and a pamphlet of WO96/37804. An optically-compensatory sheet for STN-mode liquid-crystal cells is described in JP-A 9-26572. An optically-compensatory sheet for VA-mode liquid-crystal cells is described in Japanese Patent No. 2866372.

In the invention, retardation plates (optically-compensatory sheets) for liquid-crystal cells of various modes may be fabricated with reference to the above-mentioned patent publications. The retardation plate of the invention may be used in liquid-crystal display devices of various display modes such as TN (twisted nematic), IPS (in-plane switching), FLC (ferroelectric liquid-crystal), OCB (optically-compensatory bent), STN (super-twisted nematic), VA (vertically-aligned) and HAN (hybrid aligned nematic) modes.

The liquid-crystal display device comprises a liquid-crystal cell, a polarizer and a retardation plate (optically-compensatory sheet). The polarizer generally comprises a polarizing film and a protective film. For the polarizing film and the protective film, referred to are those described hereinabove in the section of the elliptically-polarizing plate.

EXAMPLES

The invention is described more concretely with reference to the following Examples, in which the material used, its amount and the ratio, the details of the treatment and the treatment process may be suitably modified or changed not overstepping the spirit and the scope of the invention. Accordingly, the invention should not be limitatively interpreted by the Examples mentioned below.

Example 1

Production of D-3

D-3 was produced according to the following scheme:

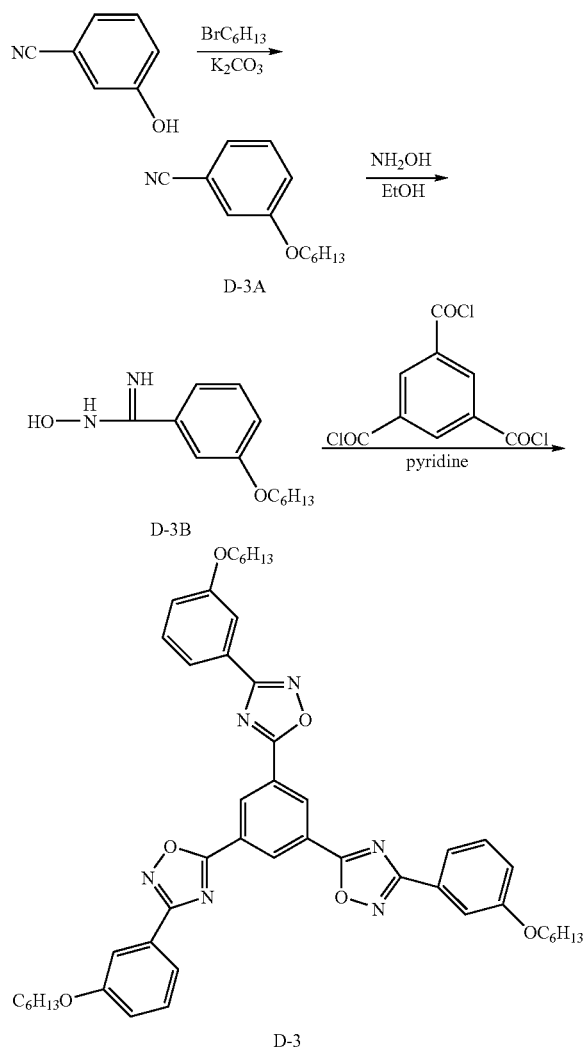

Production of D-3A 15.5 g of 3-cyanophenol was dissolved in 300 ml of dimethylformamide, and 21.2 g of potassium carbonate and 19.0 ml of 1-bromohexane were added thereto. Then, this was stirred in a nitrogen atmosphere at 110° C. for 5 hours. Water was added to the reaction solution, which was then extracted with ethyl acetate and washed with saturated saline. The organic layer was concentrated under reduced pressure, and purified through column chromatography to obtain 25.2 g of D-3A.

Production of D-3B 25.2 g of D-3A was dissolved in 200 ml of ethanol, and 26.0 ml of 50% hydroxylamine solution was added thereto, and stirred at 90° C. for 3 hours. After cooled, methanol was added to the reaction solution, and the deposited crystal was taken out through filtration and dried to obtain 28.8 g of a crystal of D-3B.

Production of D-3

28.8 g of D-3B was dissolved in 300 ml of 1,4-dioxane, and 10.2 g of trimesic acid chloride and 11.0 ml of pyridine were added thereto, and stirred at 90° C. for 7 hours. After cooled, methanol was added to it, and the deposited crystal was taken out through filtration. This was purified through column chromatography to obtain 24.0 g of D-3. Thus obtained, the NMR spectrum of D-3 is as follows:

$^1$H-NMR (solvent: CDCl$_3$, standard: tetramethylsilane) δ (ppm):

0.95 (9H, t)

1.30-1.40 (12H, m)

1.50-1.60 (6H, m)

1.80-1.90 (6H, m)

4.05 (6H, t)

7.05 (3H, d)

7.45 (3H, dd)

7.75 (3H, s)

7.85 (3H, d)

9.20 (3H, s)

The phase transition temperature of the thus-obtained D-3 was determined through texture observation with a polarizing microscope. The compound was heated, and at about 100° C., its crystal phase changed to a discotic nematic liquid-crystal phase. At over 140° C., its phase further changed to an isotropic liquid phase. Accordingly, it was found that D-3 shows a discotic nematic liquid-crystal phase within a range of from 100° C. to 140° C.

Example 2
Production of D-7
D-7 was produced according to the following scheme:
Tri-Hydroxy Compound
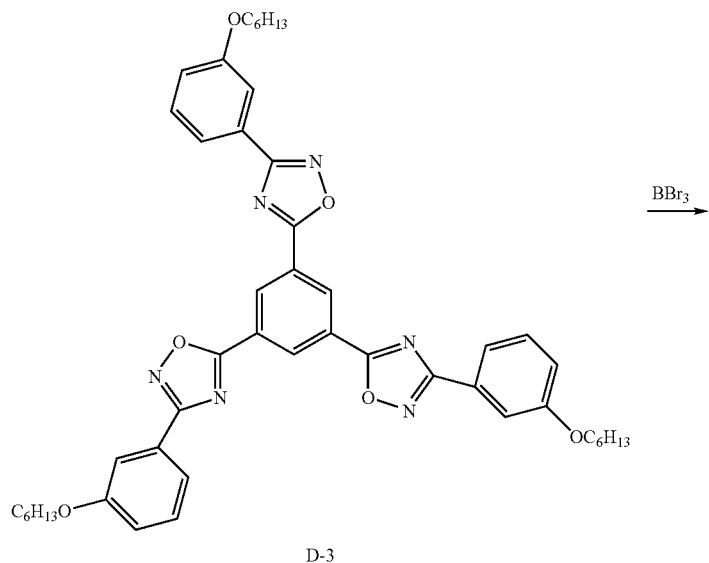
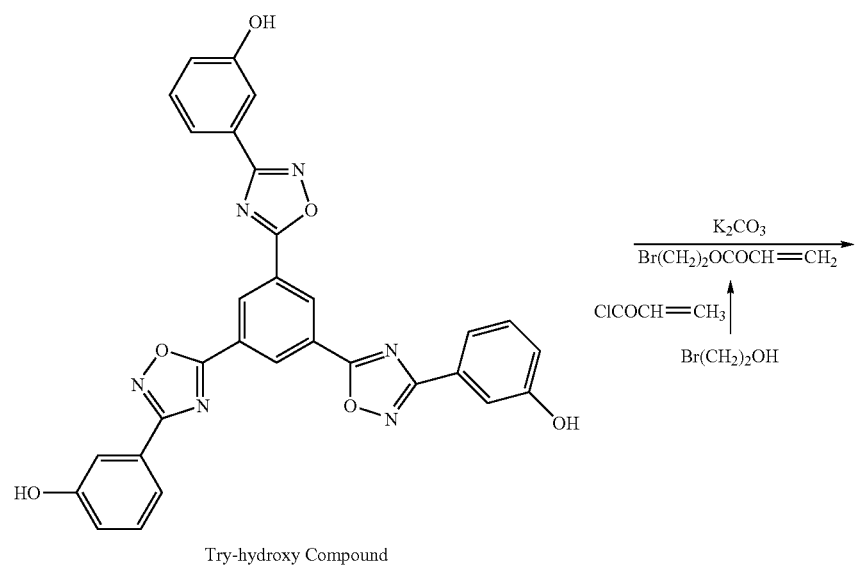
Try-hydroxy Compound

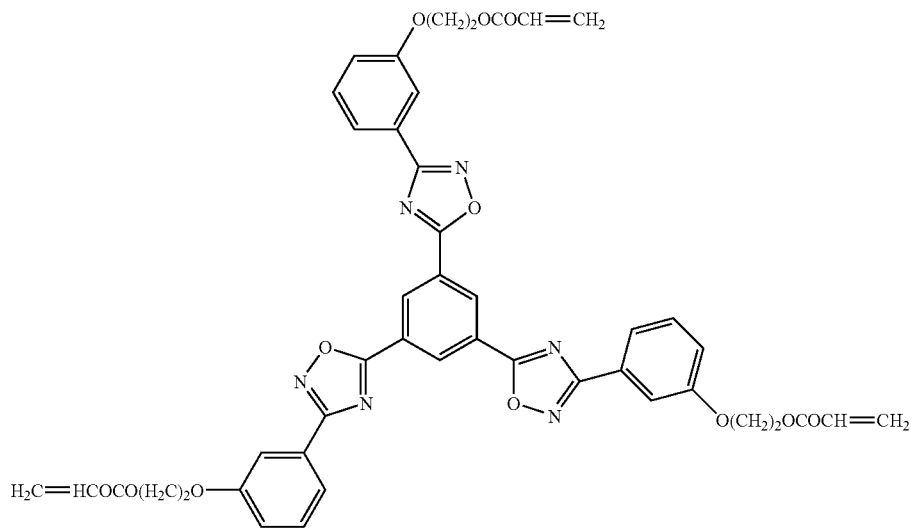

D-7

11.5 g of D-3 was dissolved in 100 ml of $CH_2Cl_2$, and 140 ml of borontrifluoride (1.0 M $CH_2Cl_2$ solution) was added thereto. After stirred at 40° C. for 8 hours, water was added to the reaction solution, and the deposited crystal was taken out through filtration. The crystal was dried to obtain 7.6 g of the trihydroxy compound.

0.34 g of 2-bromoethanol was dissolved in 5 ml of dimethylacetamide, and 0.26 ml of acrylic acid chloride was dropwise added thereto and stirred at room temperature for 1 hour, and then 20 ml of water and 20 ml of hexane were added thereto to wash the organic layer. After liquid-liquid separation, the hexane layer was evaporated away. 0.3 g of the above-mentioned trihydroxy compound, 0.44 g of potassium carbonate and 30 ml of dimethylformamide were added to this, and stirred at 90° C. for 5 hours. Water was added to the reaction solution and extracted with $CH_2Cl_2$, and the organic layer was concentrated and purified through column chromatography to obtain 0.35 g of a crystal of D-7. Thus obtained, the NMR spectrum of D-7 was as follows:

$^1$H-NMR (solvent: $CDCl_3$, standard: tetramethylsilane) δ (ppm):

4.33 (6H, t)
4.60 (6H, t)
5.89 (3H, dd)
6.20 (3H, dd)
6.50 (3H, dd)
7.15 (3H, d)
7.50 (3H, dd)
7.80 (3H, s)
7.90 (3H, d)
9.23 (3H, s)

The phase transition temperature of the thus-obtained D-7 was determined through texture observation with a polarizing microscope. The compound was heated, and at about 128° C., its crystal phase changed to a discotic nematic liquid-crystal phase. At over 131° C., its phase further changed to an isotropic liquid phase. Accordingly, it was found that D-7 shows a discotic nematic liquid-crystal phase within a range of from 128° C. to 131° C.

Example 3

Production of D-8

D-8 was produced according to the following scheme:

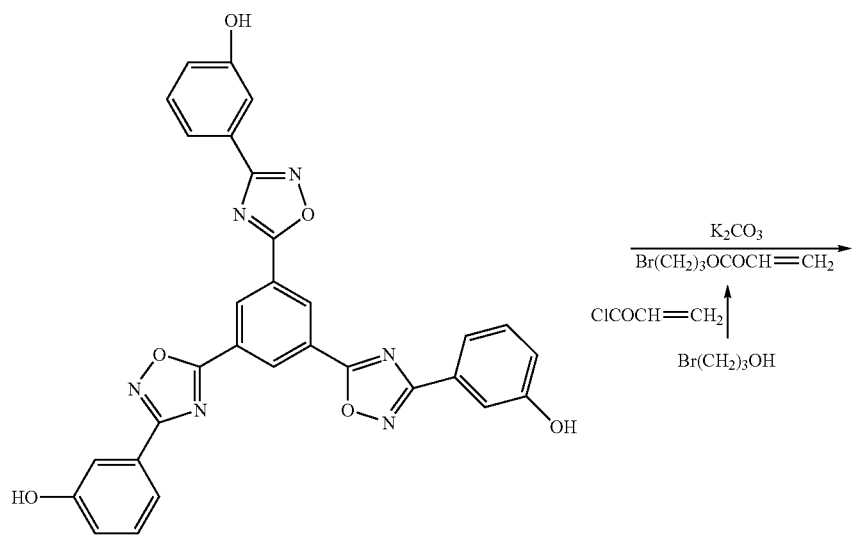

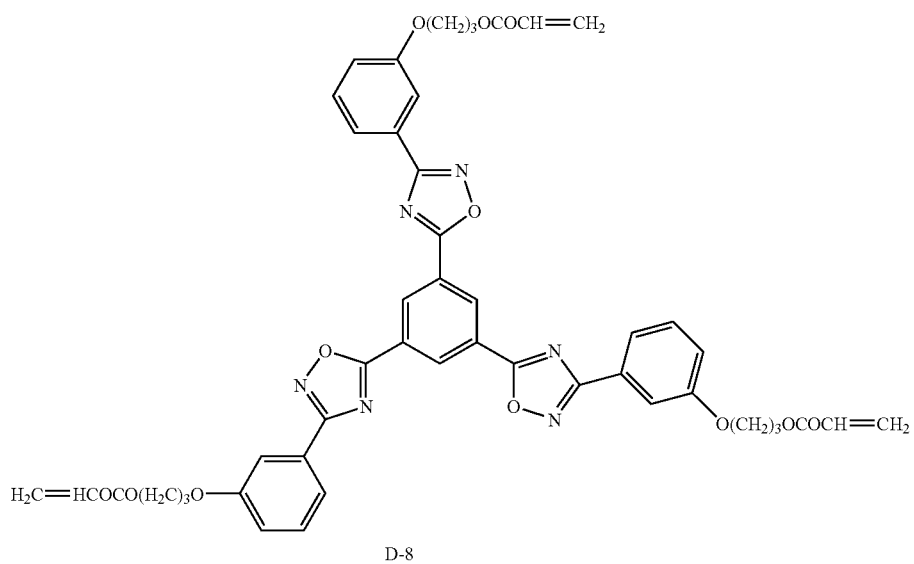

0.8 g of D-8 was obtained according to the same method as in Example 2, for which, however, the starting material was changed as in the above. Thus obtained, the NMR spectrum of D-8 was as follows:

$^1$H-NMR (solvent: CDCl$_3$, standard: tetramethylsilane) δ (ppm):
2.20-2.30 (6H, m)
4.20 (6H, t)
4.40 (6H, t)
5.85 (3H, dd)
6.25 (3H, dd)
6.45 (3H, dd)
7.15 (3H, d)
7.45 (3H, dd)
7.75 (3H, s)
7.85 (3H, d)
9.30 (3H, s)

The phase transition temperature of the thus-obtained D-8 was determined through texture observation with a polarizing microscope. The compound was heated, and at about 115° C., its crystal phase changed to a discotic nematic liquid-crystal phase. At over 129° C., its phase further changed to an isotropic liquid phase. Accordingly, it was found that D-8 shows a discotic nematic liquid-crystal phase within a range of from 115° C. to 129° C.

Example 4

Production of D-9

D-9 was produced according to the following scheme:

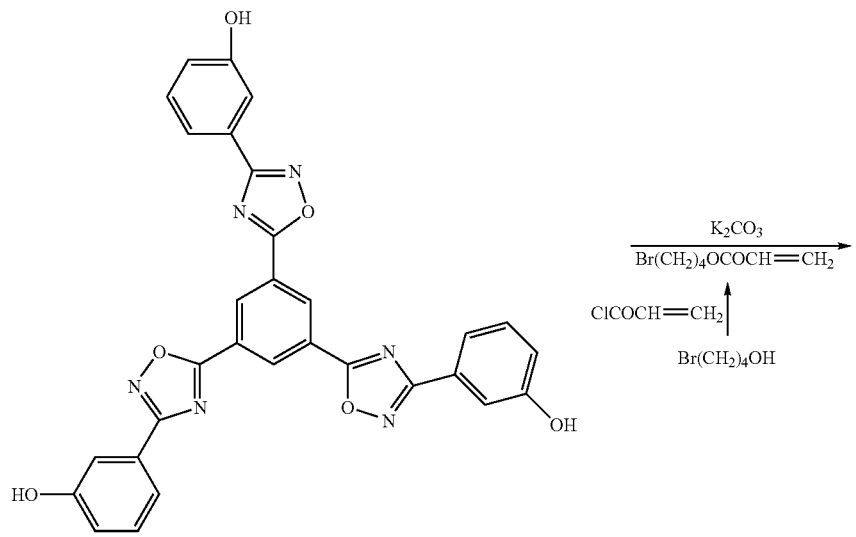

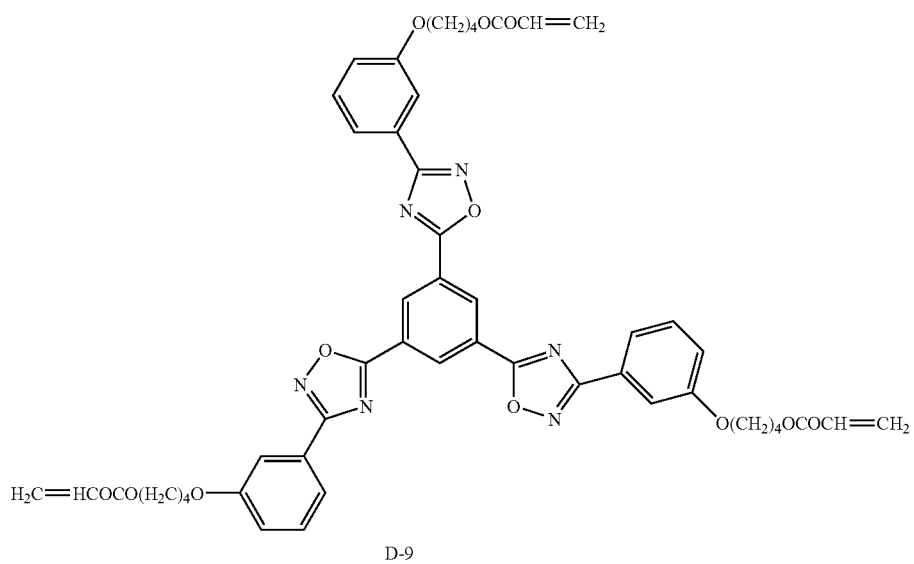

D-9

5.8 g of D-9 was obtained according to the same method as in Example 2, for which, however, the starting material was changed as in the above. Thus obtained, the NMR spectrum of D-9 was as follows:

$^1$H-NMR (solvent: $CDCl_3$, standard: tetramethylsilane) δ (ppm):
1.90-2.00 (12H, m)
4.15 (6H, t)
4.30 (6H, t)
5.85 (3H, dd)
6.15 (3H, dd)
6.45 (3H, dd)
7.15 (3H, d)
7.45 (3H, dd)
7.75 (3H, s)
7.85 (3H, d)
9.30 (3H, s)

The phase transition temperature of the thus-obtained D-9 was determined through texture observation with a polarizing microscope. The compound was heated, and at about 55° C., its crystal phase changed to a discotic nematic liquid-crystal phase. At over 116° C., its phase further changed to an isotropic liquid phase. Accordingly, it was found that D-9 shows a discotic nematic liquid-crystal phase within a range of from 55° C. to 116° C.

Example 5

Production of D-10

D-10 was produced according to the following scheme:

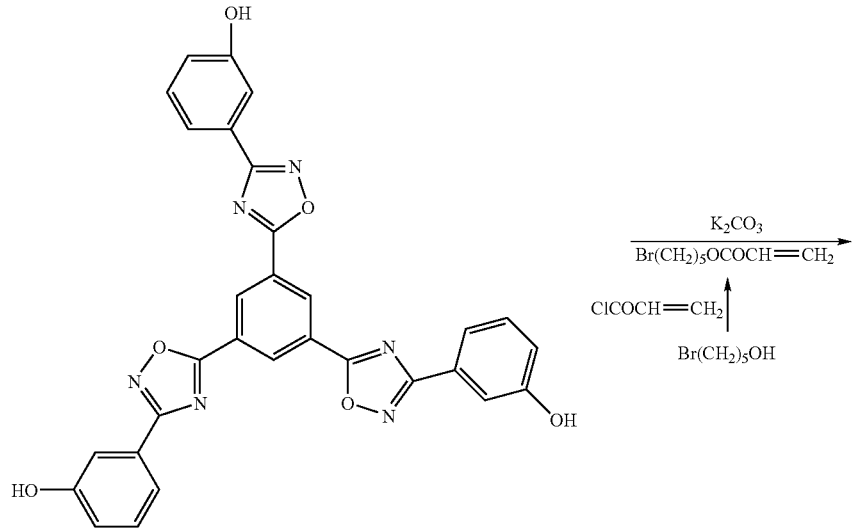

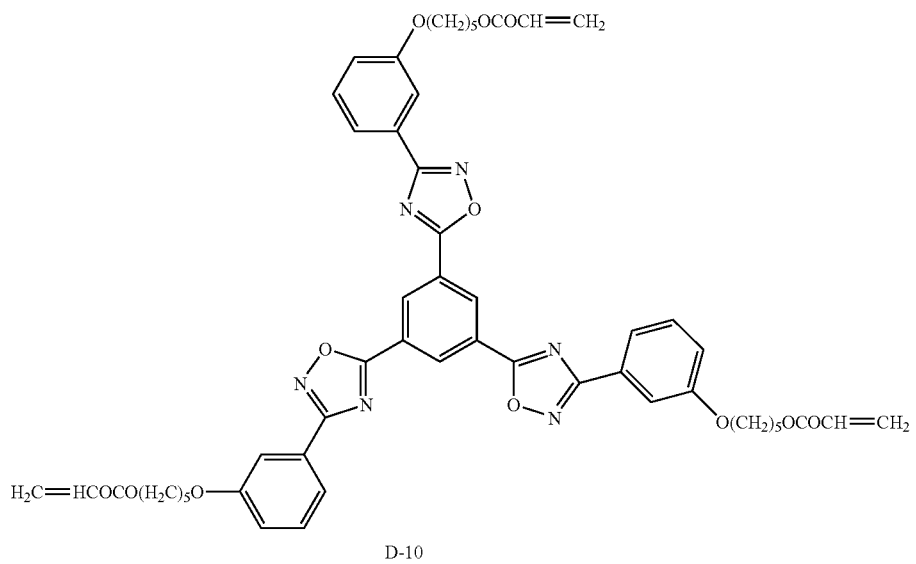

D-10

5.8 g of D-10 was obtained according to the same method as in Example 2, for which, however, the starting material was changed as in the above. Thus obtained, the NMR spectrum of D-10 was as follows:

$^1$H-NMR (solvent: CDCl$_3$, standard: tetramethylsilane) δ (ppm):
1.60-1.70 (6H, m)
1.75-1.85 (6H, m)
1.85-1.95 (6H, m)
4.15 (6H, t)
4.25 (6H, t)
5.85 (3H, dd)
6.15 (3H, dd)
6.45 (3H, dd)
7.15 (3H, d)
7.45 (3H, dd)
7.75 (3H, s)
7.85 (3H, d)
9.30 (3H, s)

The phase transition temperature of the thus-obtained D-10 was determined through texture observation with a polarizing microscope. The compound was heated, and at about 57° C., its crystal phase changed to a discotic nematic liquid-crystal phase. At over 100° C., its phase further changed to an isotropic liquid phase. Accordingly, it was found that D-10 shows a discotic nematic liquid-crystal phase within a range of from 57° C. to 100° C.

Example 6

Production of D-11

D-11 was produced according to the following scheme:

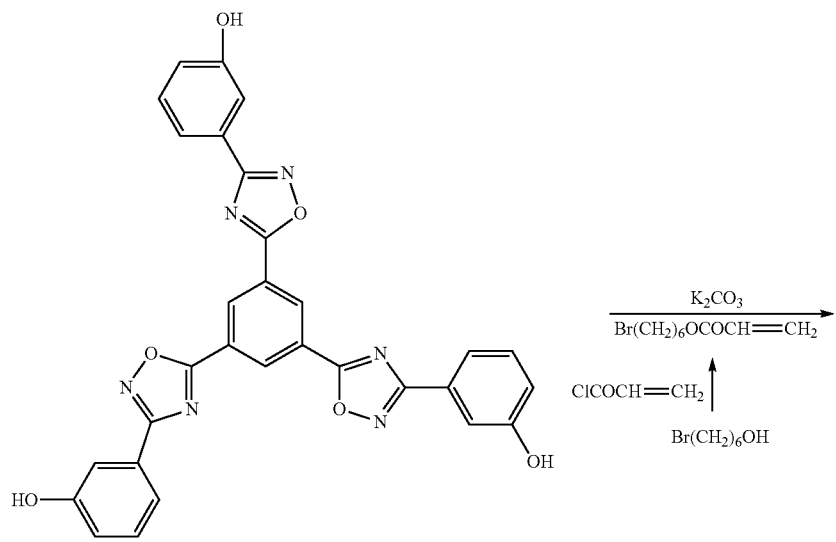

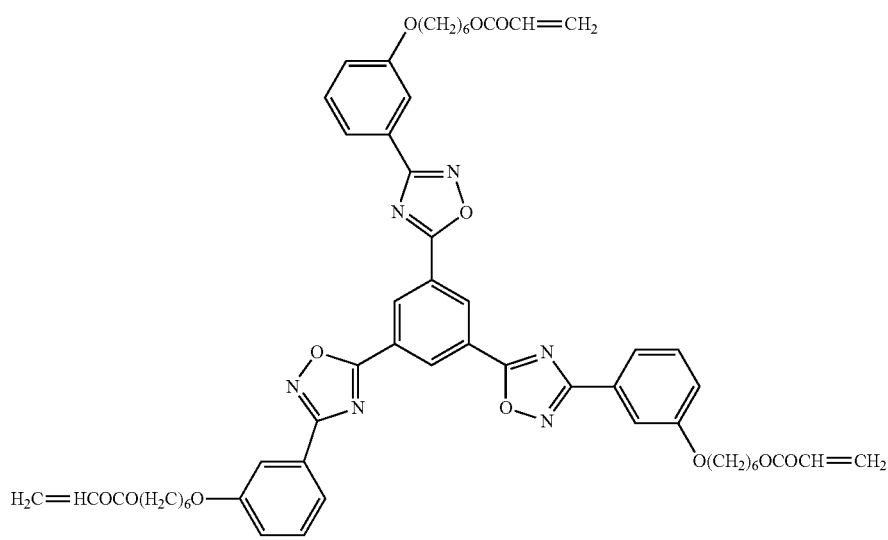

D-11

1.2 g of D-11 was obtained according to the same method as in Example 2, for which, however, the starting material was changed as in the above. Thus obtained, the NMR spectrum of D-11 was as follows:

$^1$H-NMR (solvent: CDCl$_3$, standard: tetramethylsilane) δ (ppm):
1.45-1.65 (12H, m)
1.70-1.80 (6H, m)
1.85-1.95 (6H, m)
4.15 (6H, t)
4.20 (6H, t)
5.85 (3H, dd)
6.15 (3H, dd)
6.40 (3H, dd)
7.10 (3H, d)
7.45 (3H, dd)
7.75 (3H, s)
7.85 (3H, d)
9.30 (3H, s)

The phase transition temperature of the thus-obtained D-11 was determined through texture observation with a polarizing microscope. The compound was heated, and at about 83° C., its crystal phase changed to a discotic nematic liquid-crystal phase. At over 86° C., its phase further changed to an isotropic liquid phase. Accordingly, it was found that D-11 shows a discotic nematic liquid-crystal phase within a range of from 83° C. to 86° C.

Example 7
Production of D-14
D-14 was produced according to the following scheme:
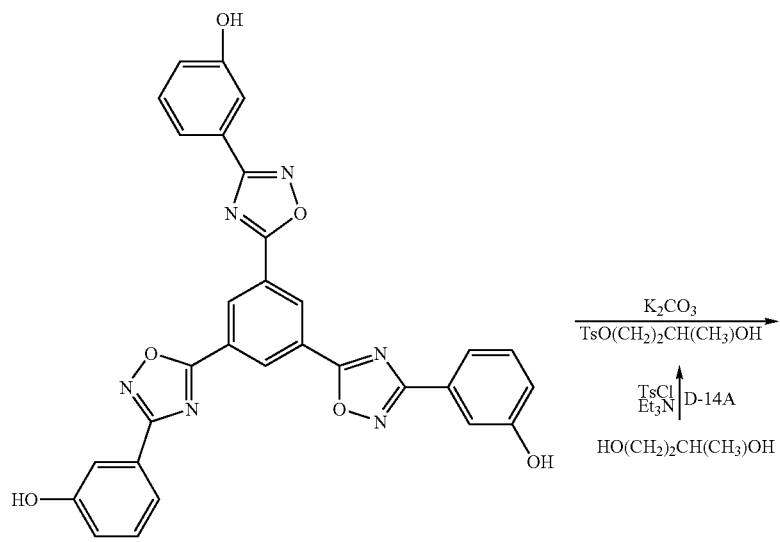
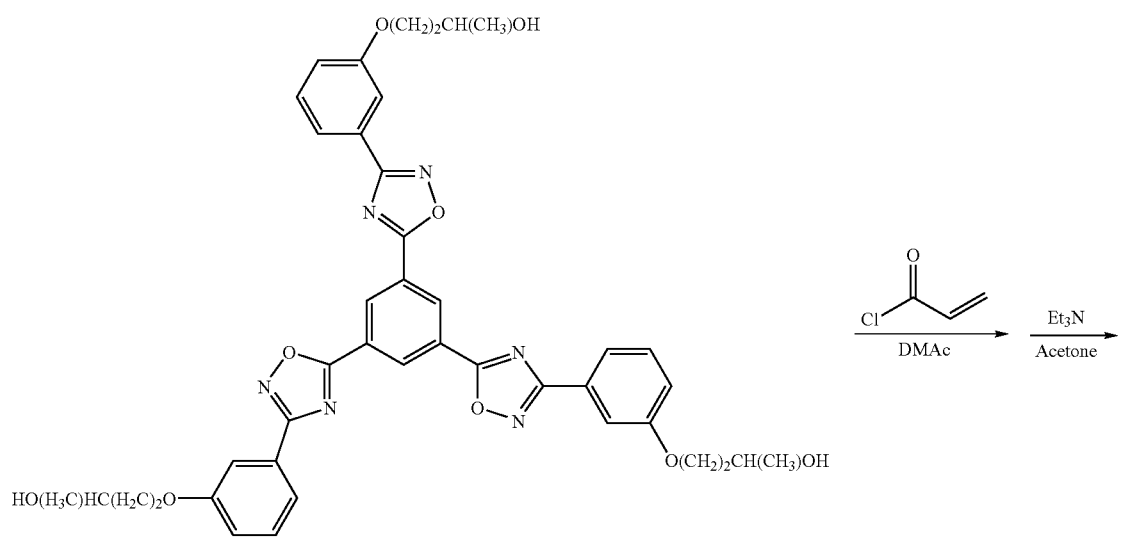
D-14 B

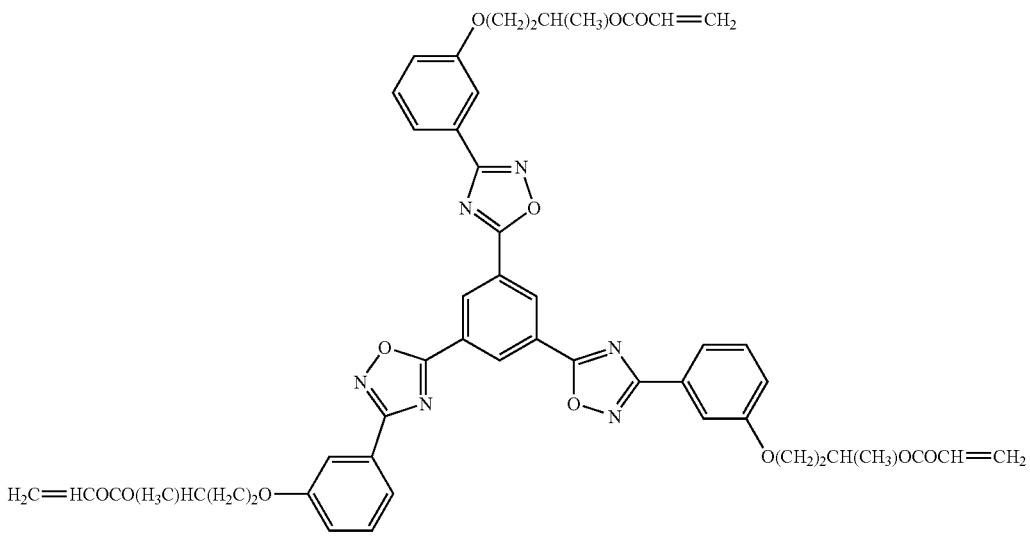

D-14

180 ml of 1-methyl-1,3-propanediol was dissolved in 150 ml of triethylamine, and 191 g of tosyl chloride dissolved in 200 ml of acetone was dropwise added thereto at room temperature. After stirred at 40° C. for 4 hours, water was added to the reaction solution, and this was then extracted with ethyl acetate. Next, water was added to the concentrated solution, and extracted with toluene, and the organic layer was concentrated under reduced pressure to obtain 161 g of D-14A. 10 g of the trihydroxy compound was dissolved in 100 ml of dimethylacetamide, and 15 g of potassium carbonate, 16 g of sodium iodide and 20 g of D-14A were added thereto, and stirred at 80° C. for 6 hours. After cooled, water was added to the reaction solution, and the deposited crystal was taken out through filtration to obtain D-14B. 2.5 g of D-14B was dissolved in 25 ml of dimethylacetamide (DMAc), and 3 ml of acryloyl chloride was dropwise added thereto. After stirred at 40° C. for 3 hours, this was cooled and methanol was added thereto. The deposited crystal was taken out through filtration. The resulting crystal was dissolved in 10 ml of dimethylacetamide, and 3 ml of triethylamine was added thereto. This was stirred at 60° C. for 4 hours. After cooled, methanol was added to it, and the deposited crystal was taken out through filtration. This was purified through column chromatography to obtain 2.3 g of D-14. Thus obtained, the NMR spectrum of D-14 was as follows:

$^1$H-NMR (solvent: CDCl$_3$, standard: tetramethylsilane) δ (ppm):

1.40 (9H, d)
2.10-2.25 (6H, m)
4.20 (6H, t)
5.20-5.30 (3H, m)
5.85 (3H, dd)
6.15 (3H, dd)
6.45 (3H, dd)
7.10 (3H, d)
7.45 (3H, dd)
7.75 (3H, s)
7.85 (3H, d)
9.30 (3H, s)

The phase transition temperature of the thus-obtained D-14 was determined through texture observation with a polarizing microscope. The compound was heated, and at about 93° C., its crystal phase changed to a discotic nematic liquid-crystal phase. At over 109° C., its phase further changed to an isotropic liquid phase. Accordingly, it was found that D-14 shows a discotic nematic liquid-crystal phase within a range of from 93° C. to 109° C.

Example 8

Production of D-38

D-38 was produced according to the following scheme:

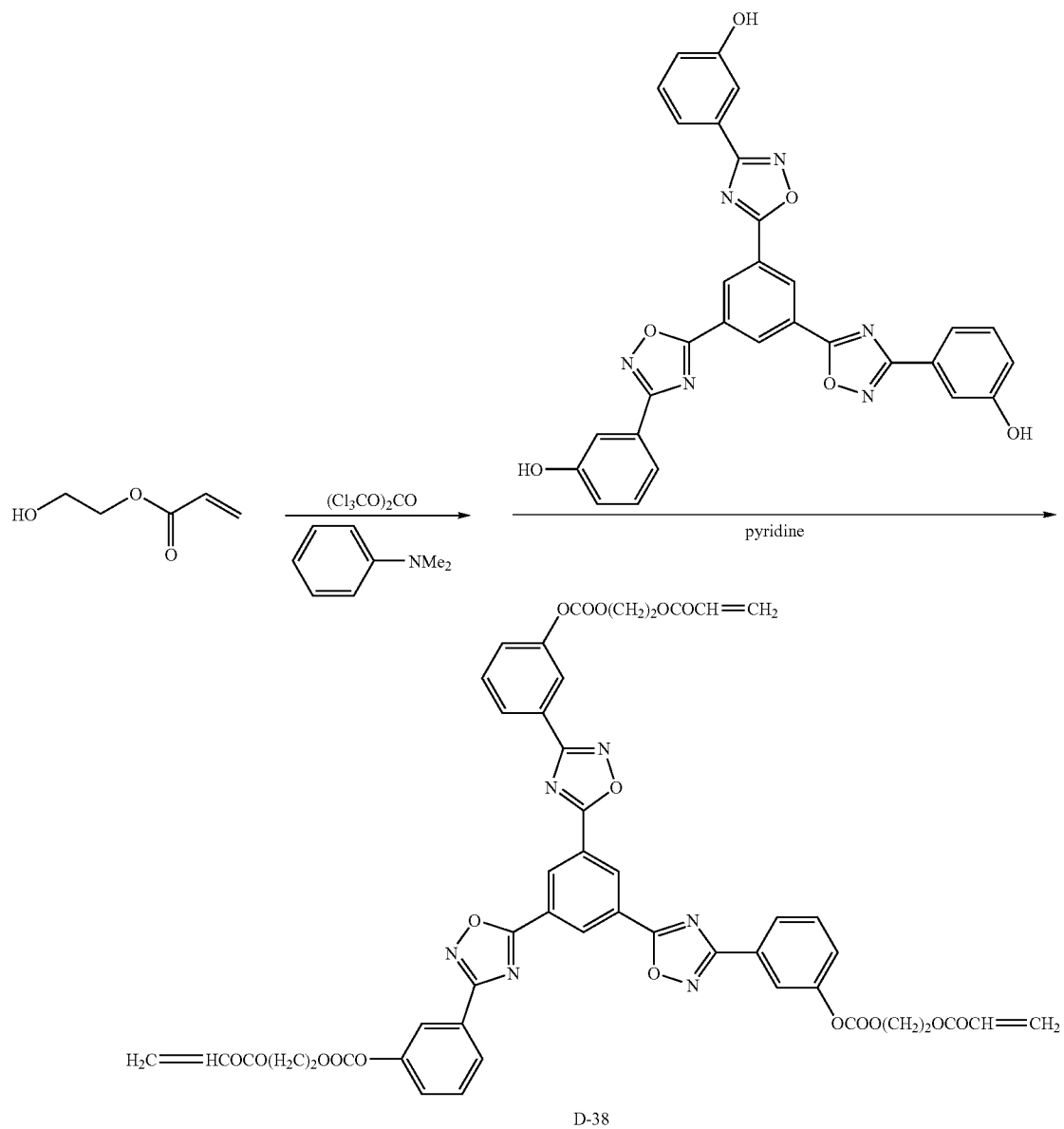

0.73 g of 2-hydroxyethyl acrylate was dissolved in 10 ml of tetrahydrofuran, and 0.84 ml of dimethylaniline was dropwise added thereto with cooling with ice, and 0.62 g of triphosgene was added thereto. After restored to room temperature and stirred for 2 hours, 0.35 g of the trihydroxy compound was added to it with cooling with ice, and 0.30 ml of pyridine was dropwise added thereto, and stirred at room temperature for 2 hours. After the reaction, methanol was added to it, and the deposited crystal was taken out through filtration. This was purified through column chromatography to obtain 0.37 g of D-38. Thus obtained, the NMR spectrum of D-38 was as follows:

$^1$H-NMR (solvent: CDCl$_3$, standard: tetramethylsilane) δ (ppm):

4.50 (6H, t)
4.60 (6H, t)
5.95 (3H, dd)
6.20 (3H, dd)
6.50 (3H, dd)
7.40 (3H, d)
7.60 (3H, dd)
8.10 (3H, s)
8.20 (3H, d)
9.30 (3H, s)

The phase transition temperature of the thus-obtained D-38 was determined through texture observation with a polarizing microscope. The compound was heated, and at about 104° C., its crystal phase changed to a discotic nematic liquid-crystal phase. At over 109° C., its phase further changed to an isotropic liquid phase. Accordingly, it was found that D-38 shows a discotic nematic liquid-crystal phase within a range of from 104° C. to 109° C.

Example 9

Production of D-40

D-40 was produced according to the following scheme:

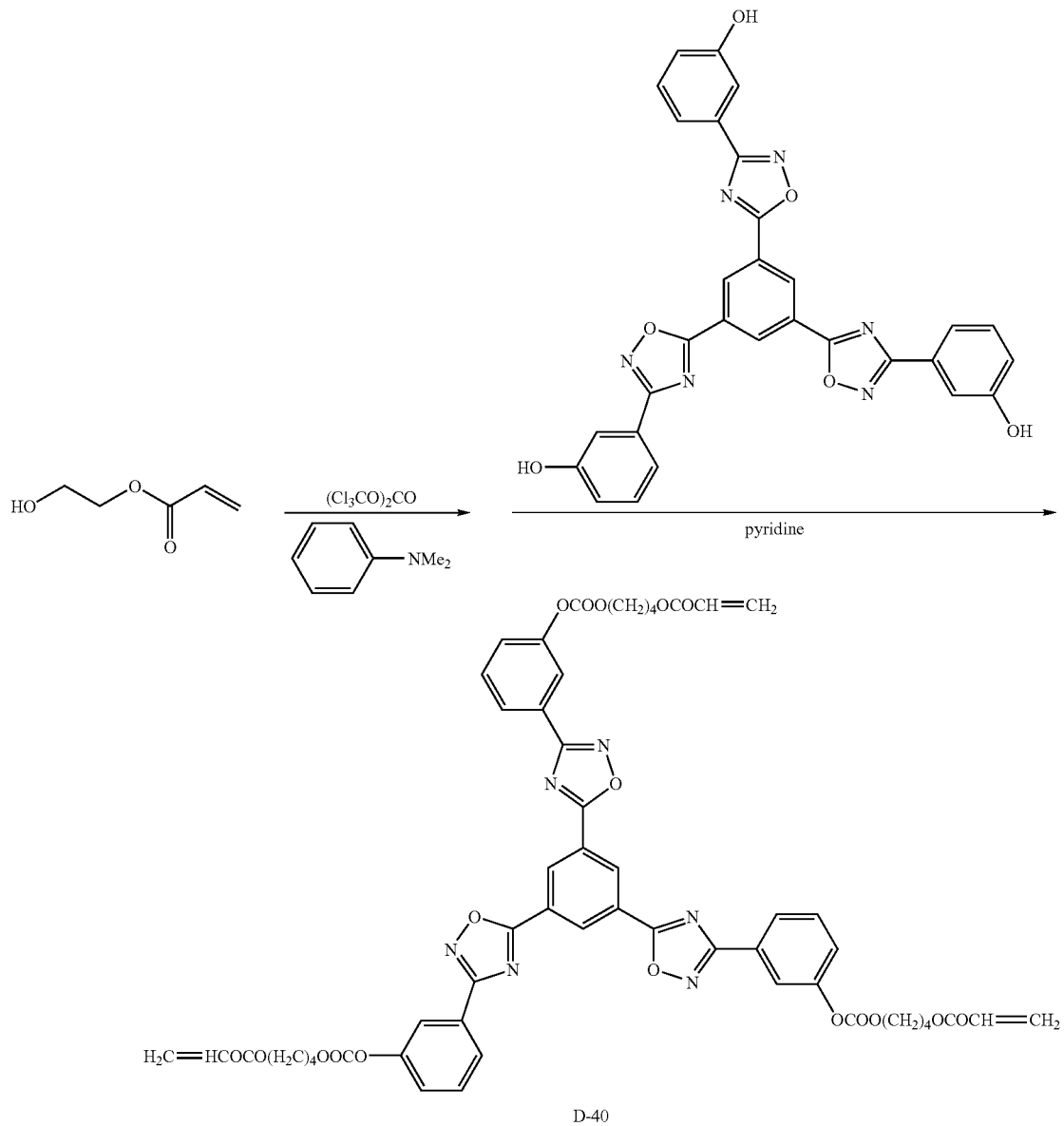

D-40

1.5 g of D-40 was obtained according to the same method as in Example 7, for which, however, 4-hydroxybutyl acrylate was used as the starting material. Thus obtained, the NMR spectrum of D-40 was as follows:

$^1$H-NMR (solvent: CDCl$_3$, standard: tetramethylsilane) δ (ppm):
1.80-2.00 (12H, m)
4.25 (6H, t)
4.35 (6H, t)
5.85 (3H, dd)
6.15 (3H, dd)
6.45 (3H, dd)
7.40 (3H, d)
7.60 (3H, dd)
8.10 (3H, s)
8.15 (3H, d)
9.30 (3H, s)

The phase transition temperature of the thus-obtained D-40 was determined through texture observation with a polarizing microscope. The compound was had a discotic nematic liquid-crystal phase at room temperature, but at over 53° C., its crystal phase changed to an isotropic liquid phase. Accordingly, it was found that D-40 shows a discotic nematic liquid-crystal phase within a range of from room temperature to 53° C.

Example 10

Formation of Thin Film of Uniformly Aligned D-9

An aqueous solution of polyvinyl alcohol (Kuraray's PVA-203) was applied onto a glass substrate, and dried at 100° C. for 3 minutes. The thickness of polyvinyl alcohol was 0.5 μm.

On the substrate on which the thin film of polyvinyl alcohol had been formed, a coating solution mentioned below was applied according to a spin-coating method. This was put into a thermostat at 80° C. and, after 5 minutes, this was exposed to 600 mJ of UV rays whereby its alignment state was fixed. This was left cooled to room temperature, and then its alignment state was observed with a polarizing microscope. It was found that the discotic liquid-crystalline compound was in homeotropic alignment with no defect therein. The thickness of the liquid-crystalline compound layer was 3.2 μm.

Coating Solution:

| | |
|---|---|
| Liquid-crystalline compound D-9 | 100 mas. pts. |
| Air interface alignment-controlling agent V-(1) mentioned below | 0.2 mas. pts. |
| Irgacure 907 (by Nagase Sangyo) | 3.0 mas. pts. |
| Diethylthioxanthone | 1.0 mas. pt. |
| Methyl ethyl ketone | 250 mas. pts. |

Air Interface Alignment-Controlling Agent V-(1):

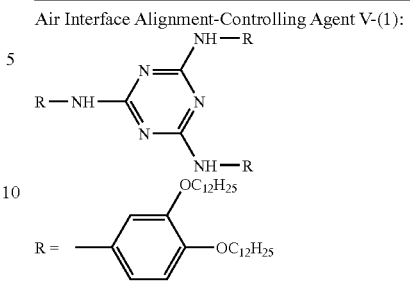

Example 11

Production of D-225

D-225 was produced according to the following scheme:

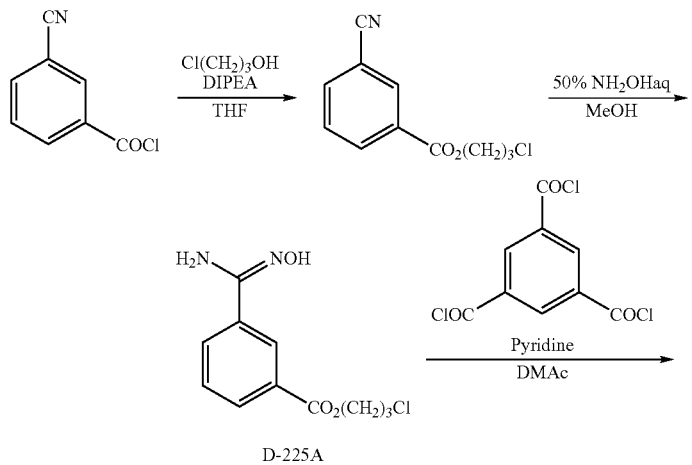

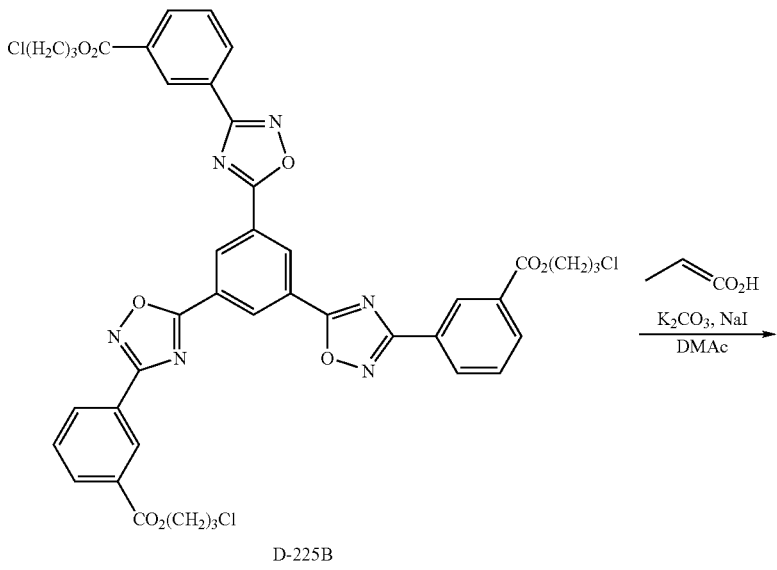

-continued

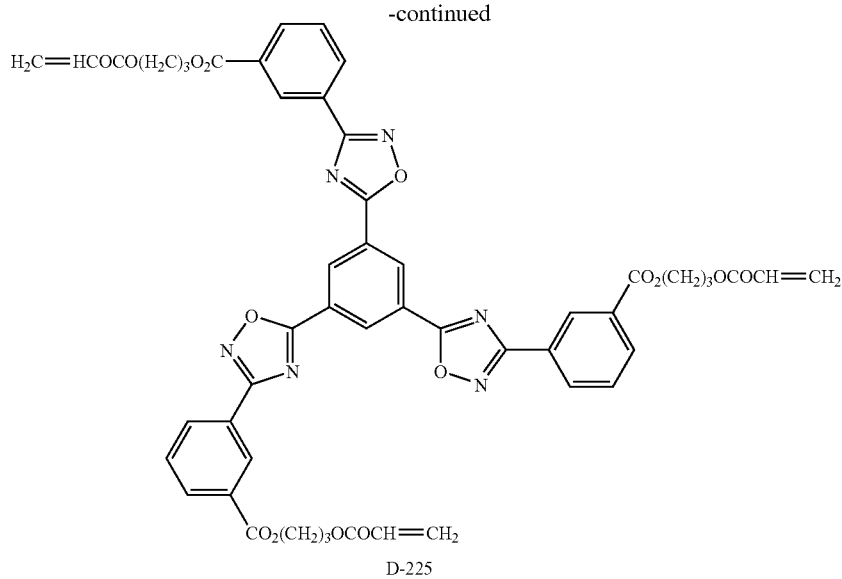

D-225

Production of D-225A 2.5 g of 3-cyanobenzoic acid chloride was dissolved in 20 ml of tetrahydrofuran (THF), and 1.3 ml of 3-chloro-1-propanol and 3.0 ml of diisopropylethylamine were added thereto and stirred at room temperature for 1 hour. Water was added to the reaction solution, and this was extracted with ethyl acetate. The organic layer was concentrated under reduced pressure. The residue was dissolved in 100 ml of methanol, and 2.8 ml of 50% hydroxylamine solution was added thereto, and stirred at 40° C. for 1 hour. After cooled, water was added to the reaction solution, and the deposited crystal was taken out through filtration and dried to obtain 3.4 g of D-225A.

Production of D-225B 3.4 g of D-225A was dissolved in 10 ml of dimethylacetamide, and 1.2 ml of pyridine and 1.2 g of trimesic acid chloride were added thereto and stirred at 120° C. for 1 hour. After cooled, methanol was added to it, and the deposited crystal was taken out and dried to obtain 3.9 g of D-225B.

Production of D-225

3.9 g of D-225B was dissolved in 50 ml of dimethylacetamide, and 3.7 g of potassium carbonate, 2.0 g of sodium iodide and 1.9 ml of acrylic acid were added thereto and stirred at 100° C. for 3 hours. Water was added to the reaction solution, and the deposited crystal was taken out through filtration. This was purified through column chromatography to obtain 3.0 g of D-225. Thus obtained, the NMR spectrum of D-225 was as follows:

$^1$H-NMR (solvent: $CDCl_3$, standard: tetramethylsilane) δ (ppm):
2.30 (6H, quint)
4.40 (6H, t)
4.55 (6H, t)
5.85 (3H, dd)
6.15 (3H, dd)
6.45 (3H, dd)
7.65 (3H, t)
8.25 (3H, d)
8.45 (3H, d)
8.90 (3H, s)
9.30 (3H, s)

The phase transition temperature of the thus-obtained D-225 was determined through texture observation with a polarizing microscope. The compound was heated, and at about 115° C., its crystal phase changed to a discotic nematic liquid-crystal phase. At over 178° C., its phase further changed to an isotropic liquid phase. Accordingly, it was found that D-225 shows a discotic nematic liquid-crystal phase within a range of from 115° C. to 178° C.

Example 12

Production of D-226

D-226 was produced according to the following scheme:

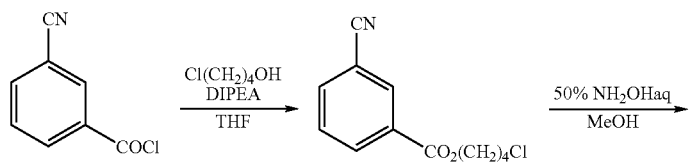

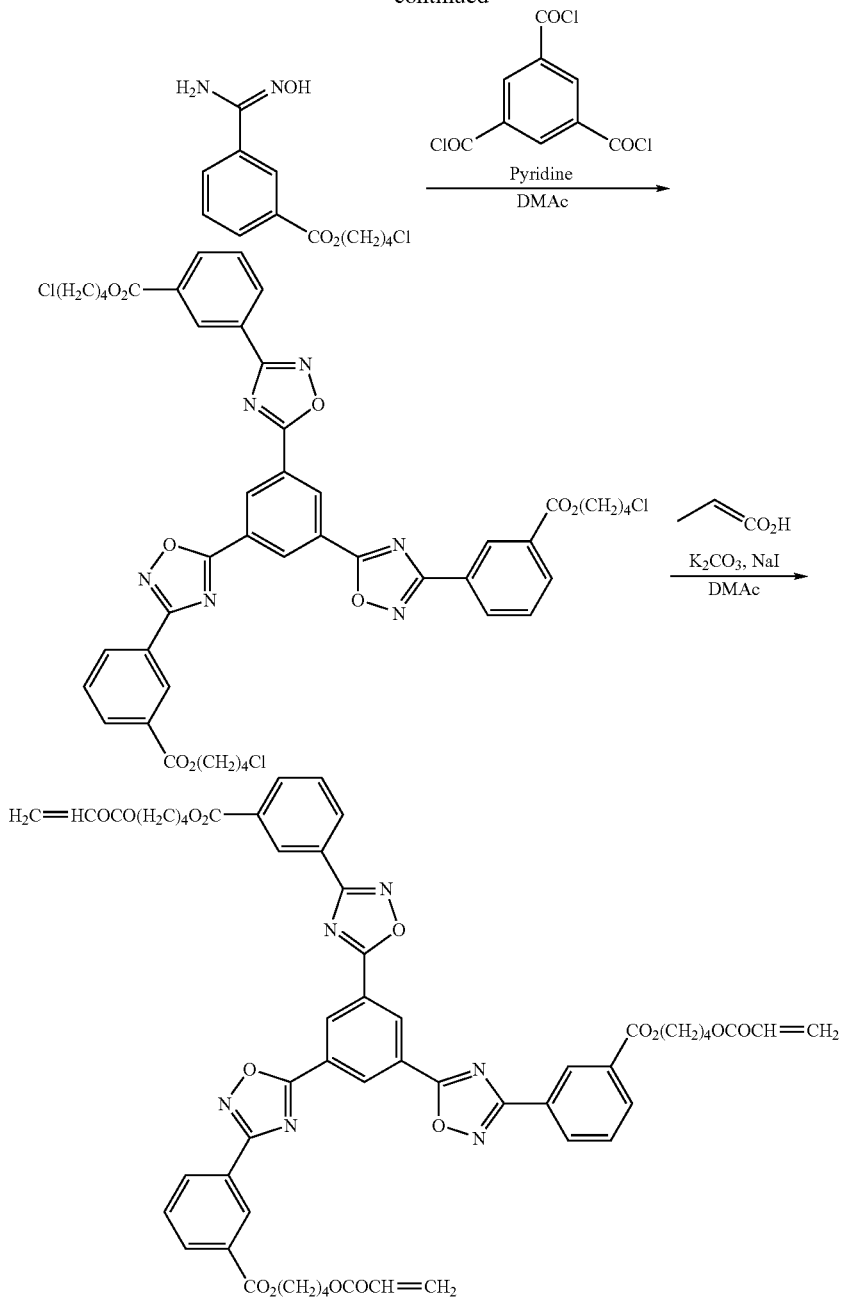

2.8 g of D-226 was obtained according to the same method as in Example 11, for which, however, 4-chloro-1-butanol was used in place of 3-chloro-1-propanol in Example 11. Thus obtained, the NMR spectrum of D-226 was as follows:

$^1$H-NMR (solvent: CDCl$_3$, standard: tetramethylsilane) δ (ppm):
1.85-2.00 (12H, m)
4.30 (6H, t)
4.45 (6H, t)
5.85 (3H, dd)
6.15 (3H, dd)
6.40 (3H, dd)
7.70 (3H, t)
8.25 (3H, d)
8.45 (3H, d)
8.90 (3H, s)
9.30 (3H, s)

The phase transition temperature of the thus-obtained D-226 was determined through texture observation with a polarizing microscope. The compound was heated, and at about 113° C., its crystal phase changed to a discotic nematic liquid-crystal phase. At over 165° C., its phase further changed to an isotropic liquid phase. Accordingly, it was found that D-226 shows a discotic nematic liquid-crystal phase within a range of from 113° C. to 165° C.

Example 13
Production of D-227
D-227 was produced according to the following scheme:
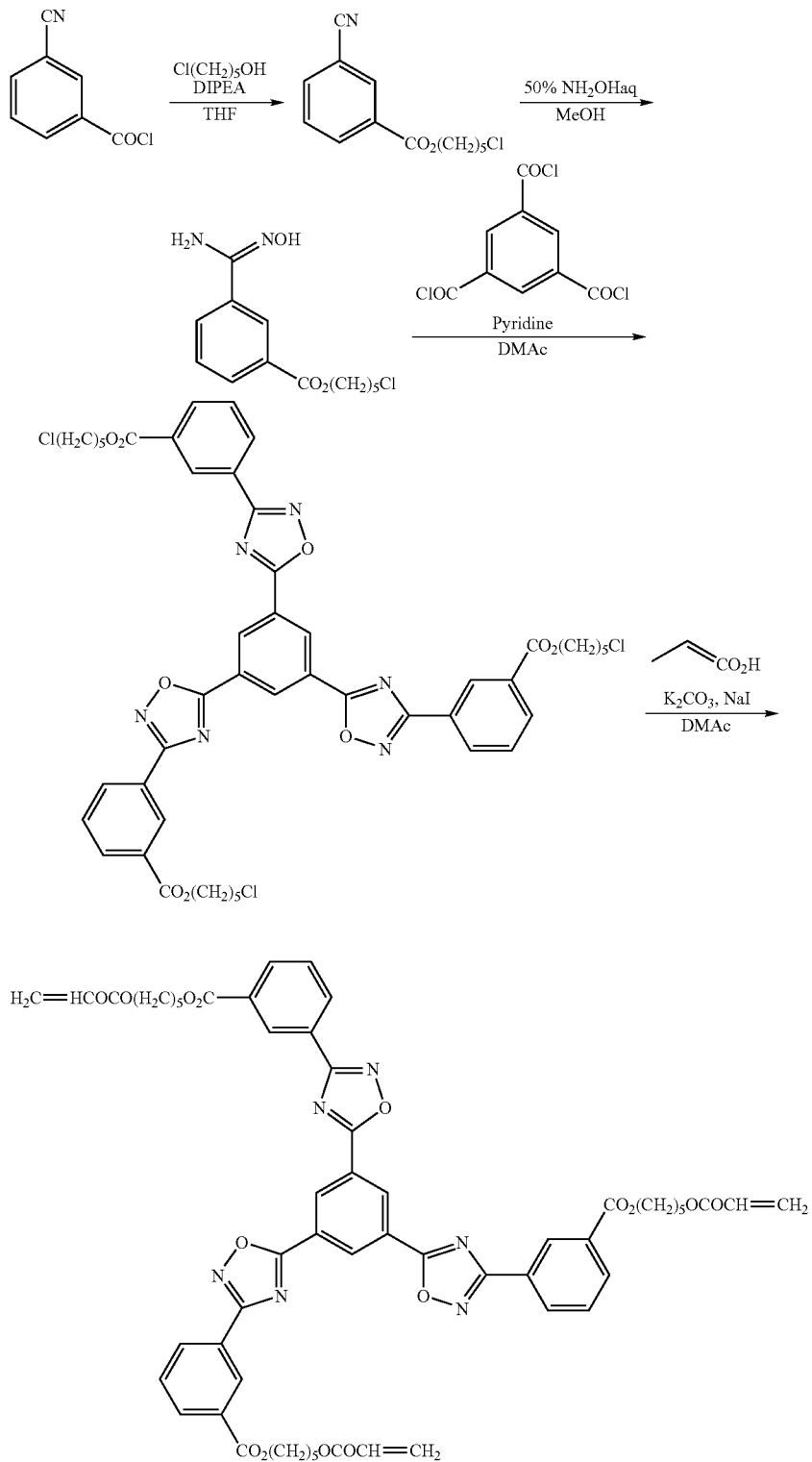

3.5 g of D-227 was obtained according to the same method as in Example 11, for which, however, 5-chloro-1-pentanol was used in place of 3-chloro-1-propanol in Example 11. Thus obtained, the NMR spectrum of D-227 was as follows:

$^1$H-NMR (solvent: CDCl$_3$, standard: tetramethylsilane) δ (ppm):
1.60 (6H, m)
1.80-1.90 (12H, m)
4.25 (6H, t)
4.45 (6H, t)
5.80 (3H, dd)
6.15 (3H, dd)
6.40 (3H, dd)
7.65 (3H, t)
8.25 (3H, d)
8.45 (3H, d)
8.90 (3H, s)
9.30 (3H, s)

The phase transition temperature of the thus-obtained D-227 was determined through texture observation with a polarizing microscope. The compound was heated, and at about 86° C., its crystal phase changed to a discotic nematic liquid-crystal phase. At over 142° C., its phase further changed to an isotropic liquid phase. Accordingly, it was found that D-227 shows a discotic nematic liquid-crystal phase within a range of from 86° C. to 142° C.

Example 14

Production of D-228

D-228 was produced according to the following scheme:

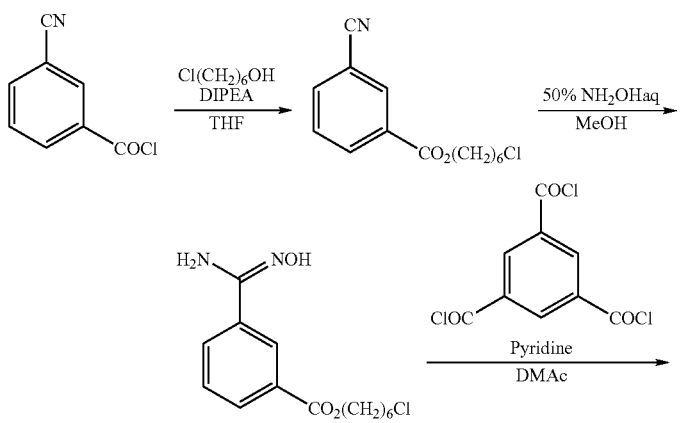

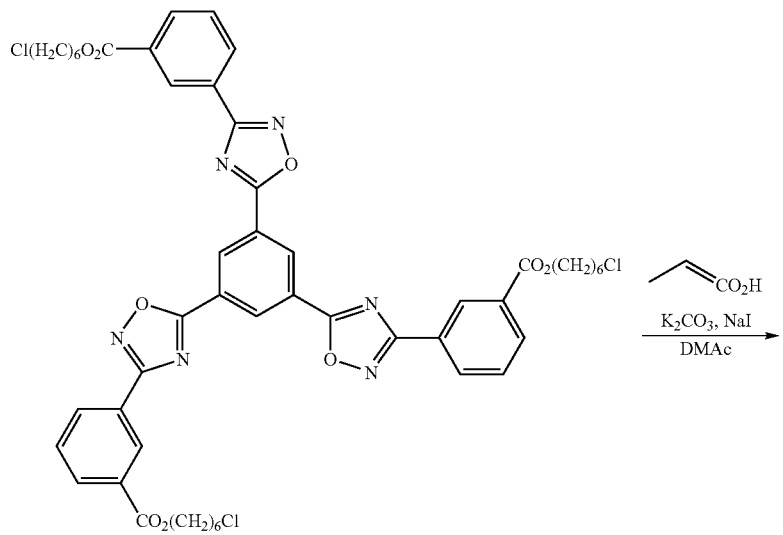

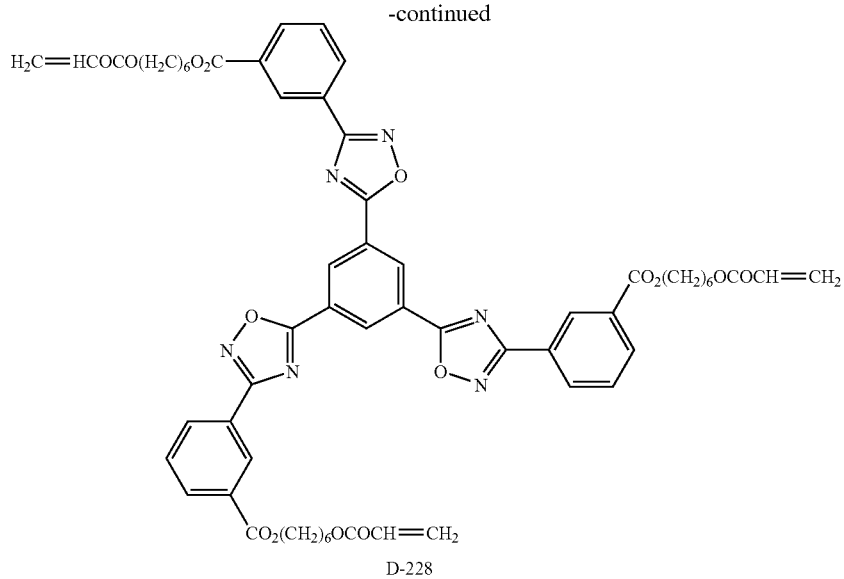

D-228

1.2 g of D-228 was obtained according to the same method as in Example 11, for which, however, 6-chloro-1-hexanol was used in place of 3-chloro-1-propanol in Example 11. Thus obtained, the NMR spectrum of D-228 was as follows:

$^1$H-NMR (solvent: CDCl$_3$, standard: tetramethylsilane) δ (ppm):
1.55 (12H, m)
1.75-1.90 (12H, m)
4.20 (6H, t)
4.40 (6H, t)
5.80 (3H, dd)
6.10 (3H, dd)
6.40 (3H, dd)
7.65 (3H, t)
8.25 (3H, d)
8.45 (3H, d)
8.90 (3H, s)
9.30 (3H, s)

The phase transition temperature of the thus-obtained D-228 was determined through texture observation with a polarizing microscope. The compound was heated, and at about 83° C., its crystal phase changed to a discotic nematic liquid-crystal phase. At over 130° C., its phase further changed to an isotropic liquid phase. Accordingly, it was found that D-228 shows a discotic nematic liquid-crystal phase within a range of from 83° C. to 130° C.

Example 15

Production of D-231

D-231 was produced according to the following scheme:

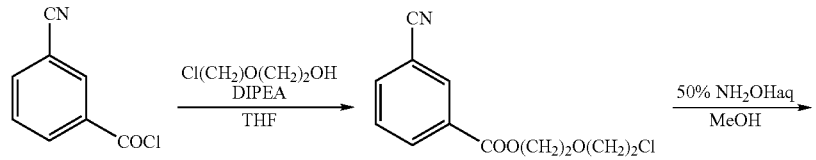

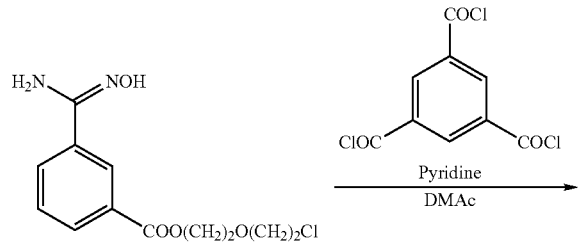

-continued

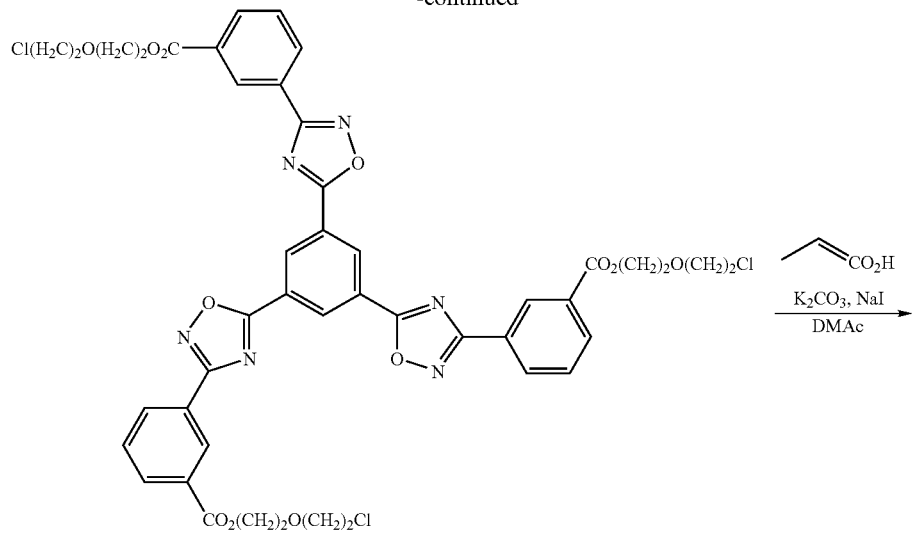

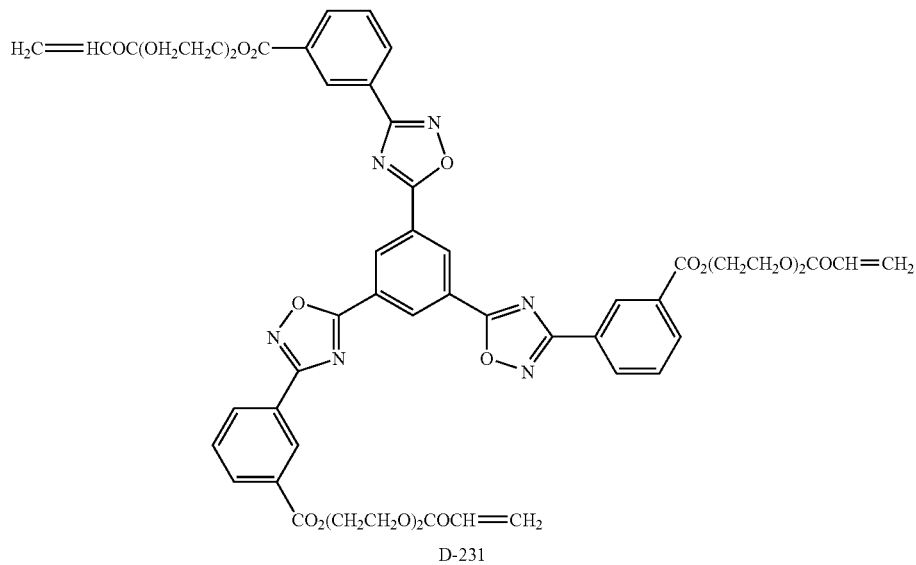

D-231

3.1 g of D-231 was obtained according to the same method as in Example 11, for which, however, 2-(2-chloroethoxy) ethanol was used in place of 3-chloro-1-propanol in Example 11. Thus obtained, the NMR spectrum of D-231 was as follows:

$^1$H-NMR (solvent: CDCl$_3$, standard: tetramethylsilane) δ (ppm):
3.85 (6H, t)
3.95 (6H, t)
4.40 (6H, t)
4.60 (6H, t)
5.80 (3H, dd)
6.15 (3H, dd)
6.40 (3H, dd)
7.65 (3H, t)
8.25 (3H, d)
8.45 (3H, d)
8.90 (3H, s)
9.30 (3H, s)

The phase transition temperature of the thus-obtained D-231 was determined through texture observation with a polarizing microscope. The compound was heated, and at about 91° C., its crystal phase changed to a discotic nematic liquid-crystal phase. At over 143° C., its phase further changed to an isotropic liquid phase. Accordingly, it was found that D-231 shows a discotic nematic liquid-crystal phase within a range of from 91° C. to 143° C.

Example 16
Production of D-238
D-238 was produced according to the following scheme:
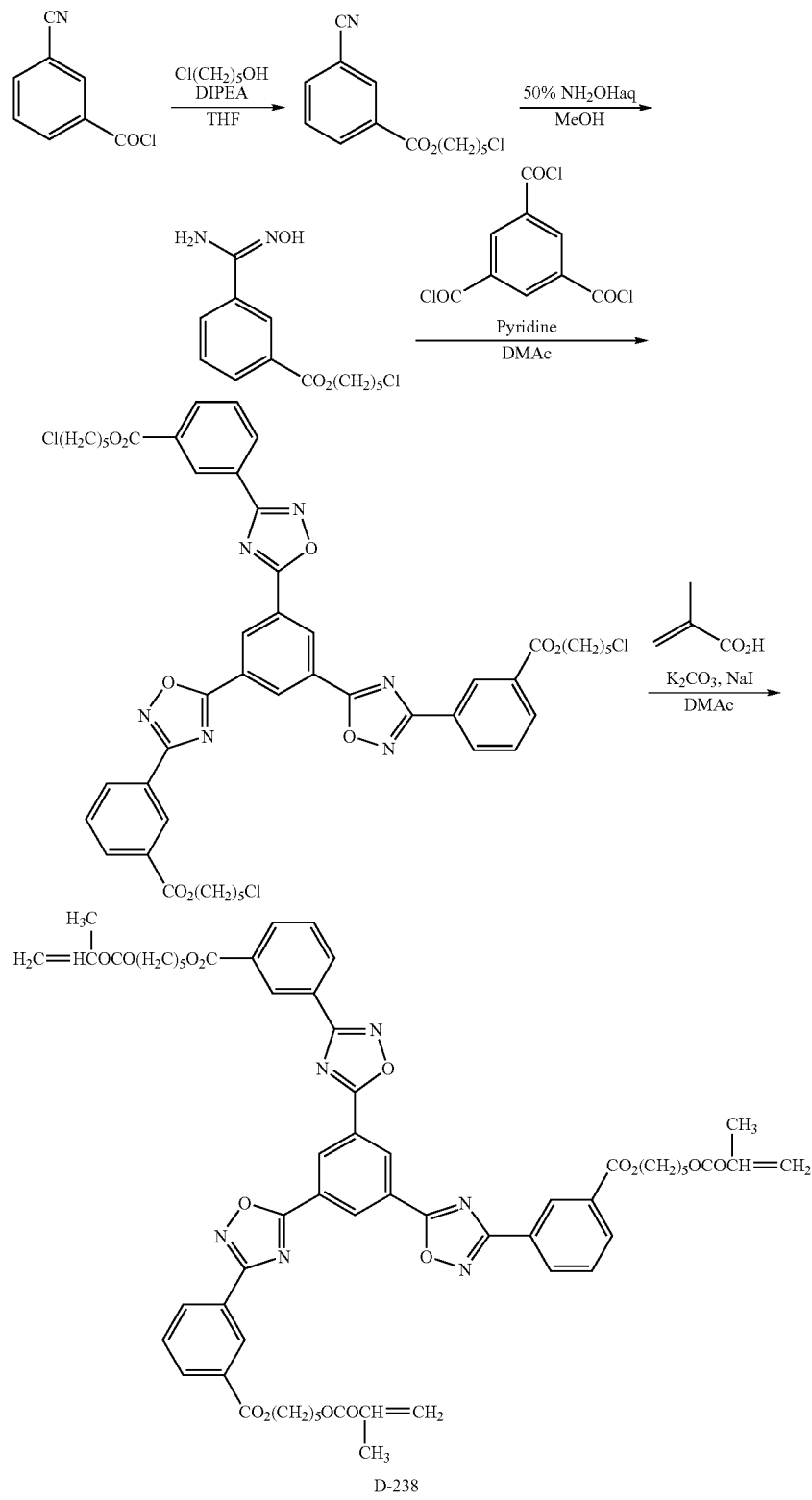

1.5 g of D-238 was obtained according to the same method as in Example 13, for which, however, methacrylic acid was used in place of acrylic acid in Example 13. Thus obtained, the NMR spectrum of D-238 was as follows:

$^1$H-NMR (solvent: CDCl$_3$, standard: tetramethylsilane) δ (ppm):
1.60 (6H, m)
1.80-1.90 (12H, m)
1.95 (9H, s)
4.20 (6H, t)
4.45 (6H, t)
5.50 (3H, s)
6.10 (3H, s)
7.70 (3H, t)
8.25 (3H, d)
8.45 (3H, d)
8.90 (3H, s)
9.30 (3H, s)

The phase transition temperature of the thus-obtained D-238 was determined through texture observation with a polarizing microscope. The compound was heated, and at about 83° C., its crystal phase changed to a discotic nematic liquid-crystal phase. At over 126° C., its phase further changed to an isotropic liquid phase. Accordingly, it was found that D-238 shows a discotic nematic liquid-crystal phase within a range of from 83° C. to 126° C.

Example 17

Production of D-268

D-268 was produced according to the following scheme:

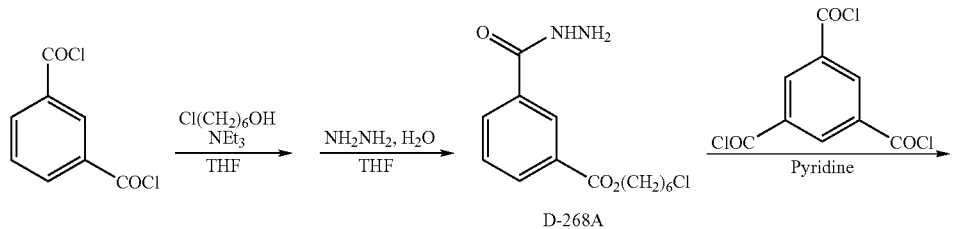

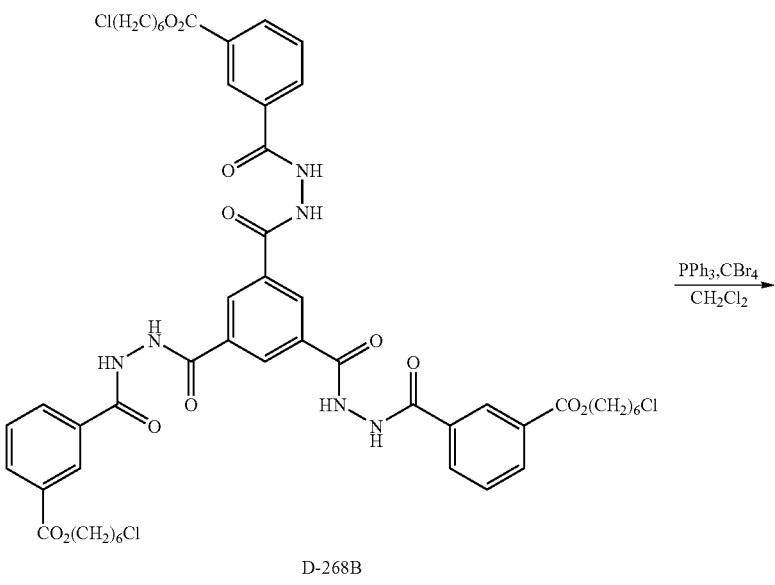

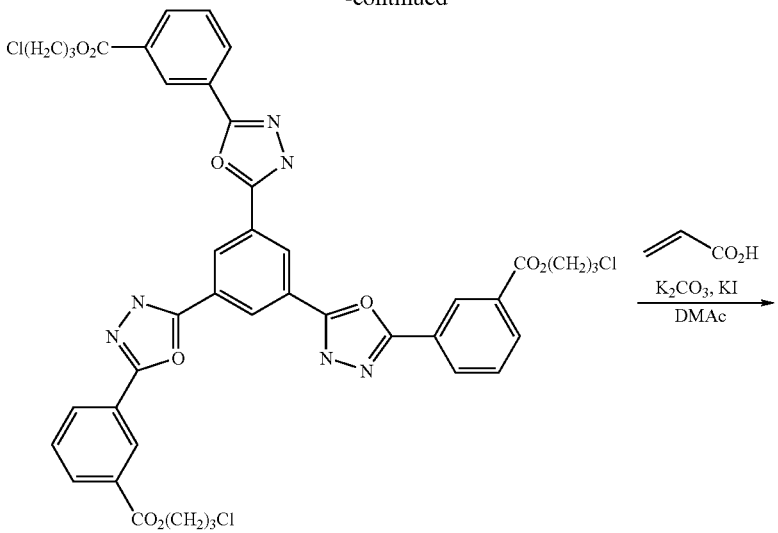

D-268C

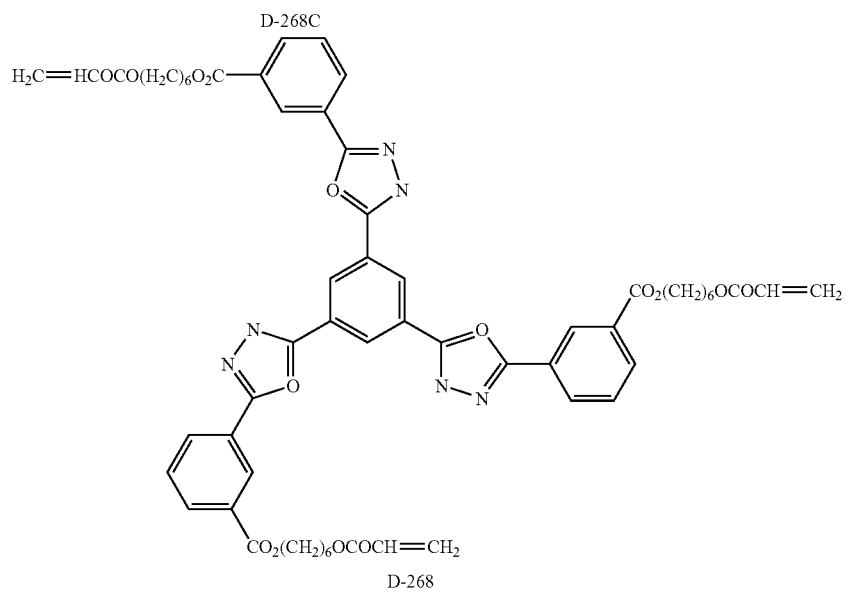

D-268

Production of D-268A 10.0 g of isophthaloyl chloride and 7.4 g of 6-chloro-1-hexanol were dissolved in 70 ml of THF, and cooled to −10° C., and 11.3 ml of triethylamine was added to it and stirred at room temperature for 1 hour. In a different flask, 49.3 g of hydrazine monohydrate was dissolved in 140 ml of THF, and cooled to −40° C., and the previous reaction solution was dropwise added to it. This was stirred at room temperature for 1 hour, and water was added to the reaction solution, and extracted with ethyl acetate. The organic layer was concentrated under reduced pressure. This was purified through column chromatography to obtain 6.0 g of D-268A.

Production of D-268B 5.6 g of D-268A was dissolved in 50 ml of THF, and 2.9 ml of triethylamine and 1.7 g of trimesic acid chloride were added thereto and stirred at room temperature for 1 hour. Water was added to the reaction solution, and extracted with ethyl acetate. The organic layer was concentrated under reduced pressure to obtain 6.6 g of D-268B.

Production of D-268C 6.6 g of D-268B and 6.4 g of triphenylphosphine were dissolved in 110 ml of methylene chloride, and 8.1 g of carbon tetrabromide and 6.7 ml of triethylamine were added to it and stirred at 40° C. for 1 hour. The reaction solution was concentrated under reduced pressure, and purified through column chromatography to obtain 3.8 g of D-268C.

Production of D-268

3.6 g of D-268C was dissolved in 50 ml of dimethylacetamide, and 6.0 g of potassium carbonate, 3.6 g of potassium iodide and 1.5 ml of acrylic acid were added thereto and stirred at 90° C. for 3 hours. Water was added to the reaction solution, and the deposited crystal was taken out through filtration. This was purified through column chromatography to obtain 2.8 g of D-268. Thus obtained, the NMR spectrum of D-268 was as follows:

¹H-NMR (solvent: CDCl₃, standard: tetramethylsilane) δ (ppm):
  1.50 (12H, m)
  1.75-1.90 (12H, m)
  4.20 (6H, t)
  4.45 (6H, t)
  5.80 (3H, dd)
  6.10 (3H, dd)
  6.40 (3H, dd)
  7.70 (3H, t)
  8.30 (3H, d)
  8.45 (3H, d)
  8.90 (3H, s)
  9.10 (3H, s)

The phase transition temperature of the thus-obtained D-268 was determined through texture observation with a polarizing microscope. The compound was heated, and at about 124° C., its columnar phase changed to an isotropic liquid phase. When gradually cooled from 124° C., then its phase changed to a discotic nematic phase at about 120° C. Accordingly, it was found that D-268 shows a discotic nematic phase while it is cooled.

Example 18

Production of D-286

D-286 was produced according to the following scheme:

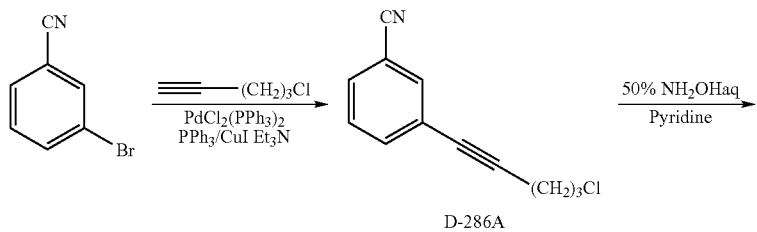

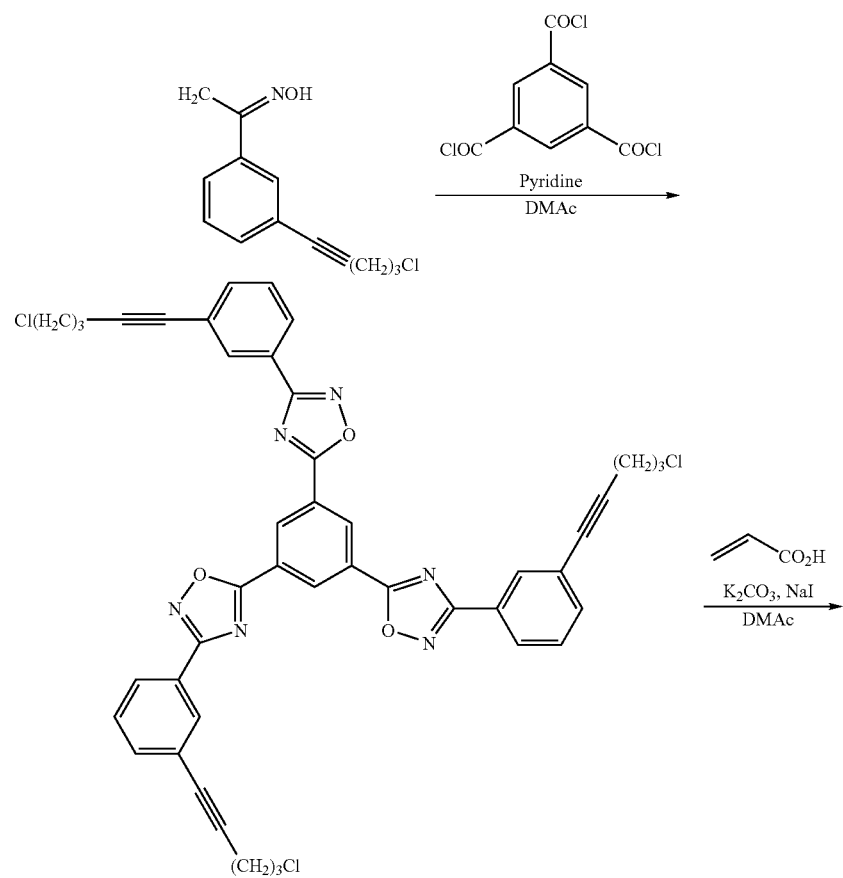

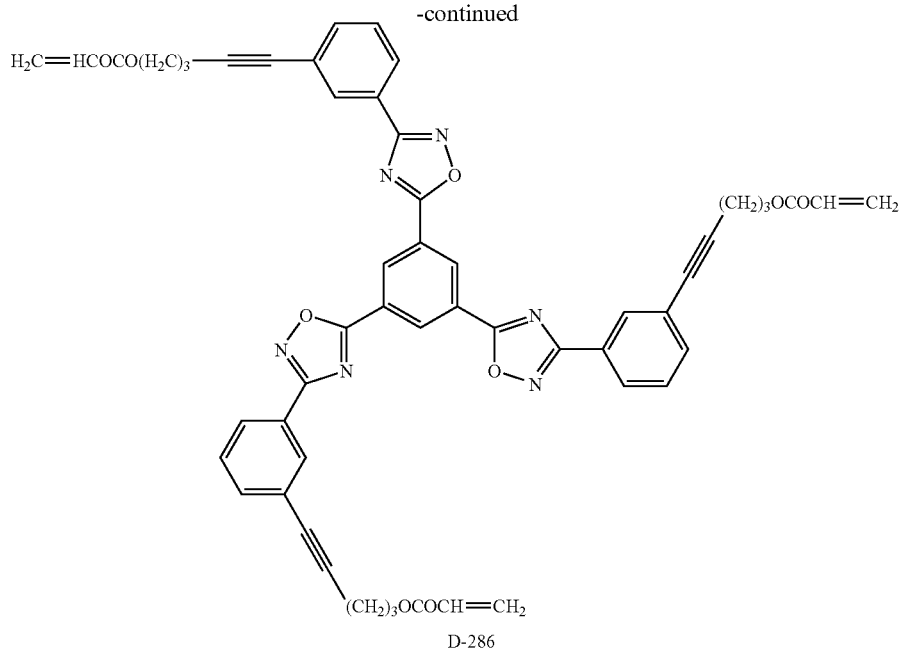

D-286A was produced from 3-bromobenzonitrile and 5-chloro-1-pentyne in an ordinary manner. Next, in the same manner as in Example 11, 2.8 g of D-286 was obtained. The NMR spectrum of D-286 was as follows:

$^{1}$H-NMR (solvent: CDCl$_3$, standard: tetramethylsilane) δ (ppm):
2.00-2.15 (6H, m)
2.62 (6H, t)
4.38 (6H, t)
5.85 (3H, dd)
6.18 (3H, dd)
6.45 (3H, dd)
7.50 (3H, t)
7.60 (3H, d)
8.15 (3H, d)
8.27 (3H, d)
9.24 (3H, s)

The phase transition temperature of the thus-obtained D-286 was determined through texture observation with a polarizing microscope. The compound was heated, and at about 63° C., its crystal phase changed to a discotic nematic liquid-crystal phase, and at over 113° C., it changed to an isotropic liquid phase. Accordingly, it was found that D-286 shows a discotic nematic liquid-crystal phase within a range of from 63° C. to 113° C.

Example 19

Production of D-291

D-291 was produced according to the following scheme:

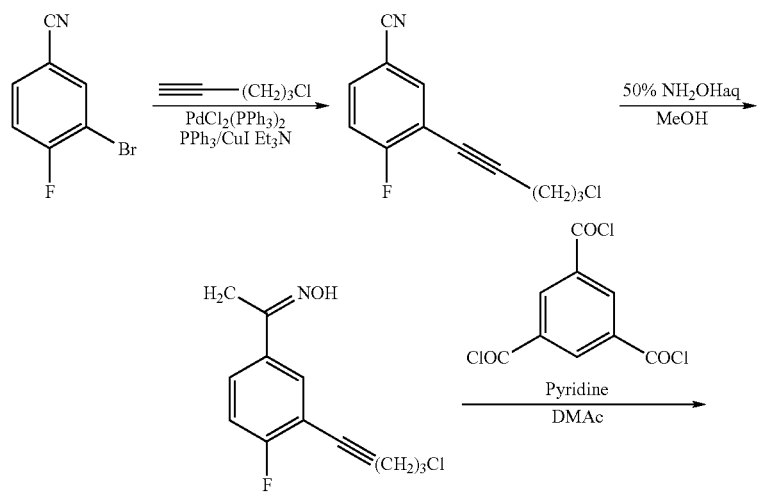

-continued

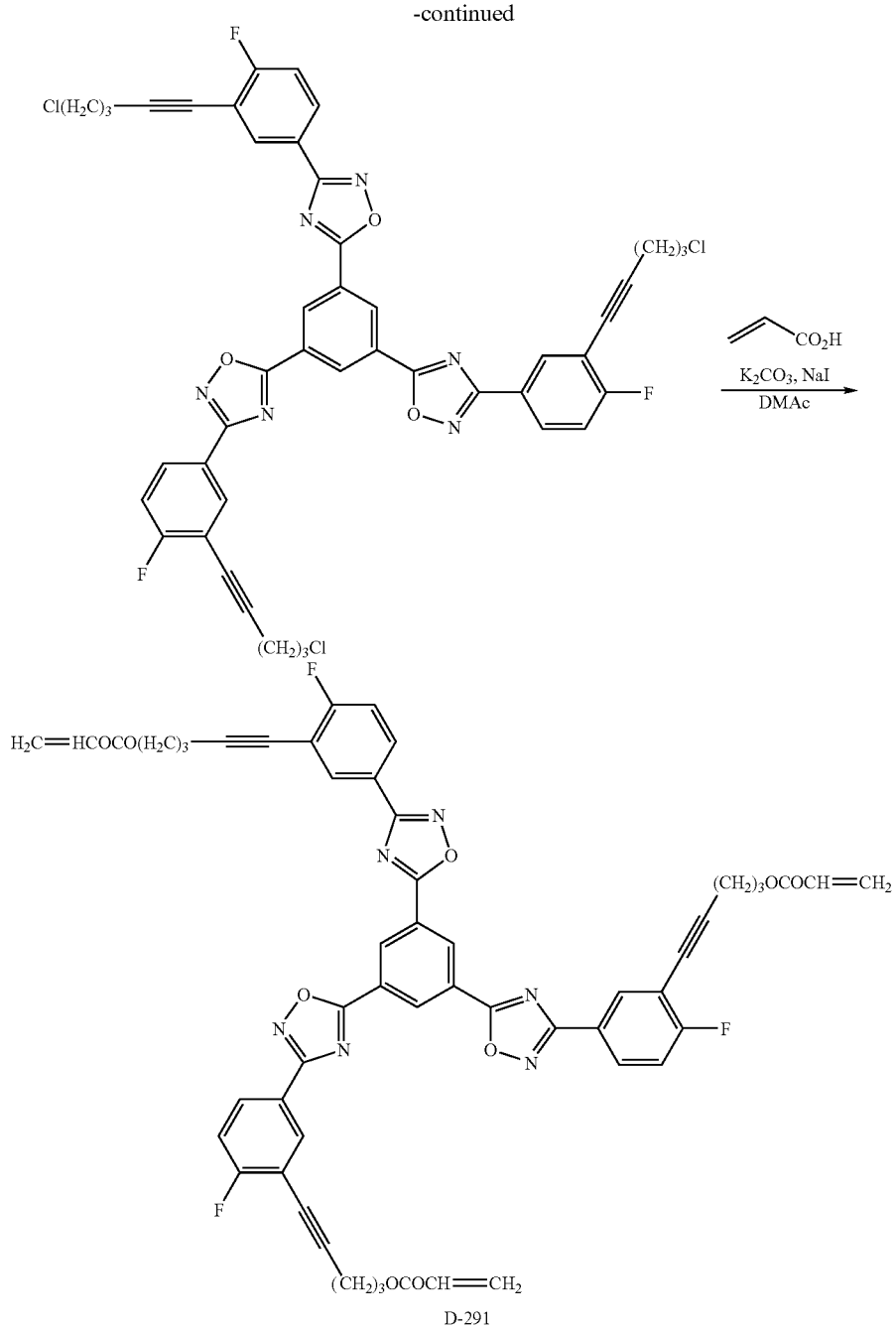

D-291

In the same manner as in Example 18 but using 3-bromo-4-fluorobenzonitrile in place of 3-bromobenzonitrile, 1.1 g of D-291 was obtained. The NMR spectrum of D-291 was as follows:

$^1$H-NMR (solvent: CDCl$_3$, standard: tetramethylsilane) δ (ppm):

2.00-2.15 (6H, m)
2.62 (6H, t)
4.38 (6H, t)
5.85 (3H, dd)
6.18 (3H, dd)
6.45 (3H, dd)
7.20-7.30 (3H, m)
8.10-8.20 (3H, m)
8.25-8.30 (3H, m)
9.24 (3H, s)

The phase transition temperature of the thus-obtained D-291 was determined through texture observation with a polarizing microscope. The compound was heated, and at about 112° C., its crystal phase changed to a discotic nematic liquid-crystal phase, and at over 182° C., it changed to an isotropic liquid phase. Accordingly, it was found that D-291 shows a discotic nematic liquid-crystal phase within a range of from 112° C. to 182° C.

Example 20

Production of D-141

D-141 was produced according to the following scheme:

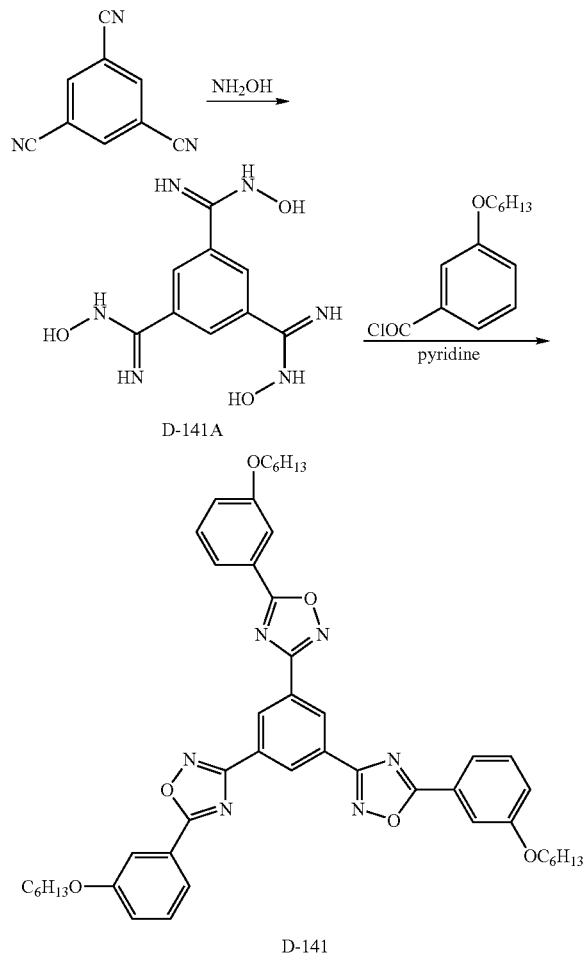

Production of D-141A 100 ml of methanol was added to 11.5 g of 1,3,5-tricyanobenzene produced in an ordinary manner, and then 26.0 ml of 50% hydroxylamine solution was added to it, and stirred at 60° C. for 3 hours. After cooled, water was added to the reaction liquid, and the deposited crystal was taken out through filtration and dried to obtain 8.0 g of a crystal of D-141A.

Production of D-141

1.0 g of D-141A was dissolved in 10 ml of dimethylacetamide, and 3.2 g of chloro-3-hexyloxybenzoate produced in an ordinary manner and 1.1 ml of pyridine were added thereto, and stirred at 125° C. for 3 hours. After cooled, methanol was added to it, and the deposited crystal was taken out through filtration. This was purified through column chromatography to obtain 0.2 g of D-141. The NMR spectrum of D-141 was as follows:

$^1$H-NMR (solvent: CDCl$_3$, standard: tetramethylsilane) δ (ppm):
0.95 (9H, t)
1.30-1.40 (12H, m)
1.50-1.60 (6H, m)
1.80-1.90 (6H, m)
4.12 (6H, t)
7.15 (3H, d)
7.48 (3H, dd)
7.80 (3H, s)
7.87 (3H, d)
9.15 (3H, s)

The phase transition temperature of the thus-obtained D-141 was determined through texture observation with a polarizing microscope. The compound was heated, and at about 143° C., its columnar phase changed to an isotropic liquid phase. When gradually cooled from 145° C., then its phase changed to a discotic nematic phase at about 128° C. Accordingly, it was found that D-141 shows a discotic nematic phase while it is cooled.

Example 21

Production of D-325

D-325 was produced according to the following scheme:

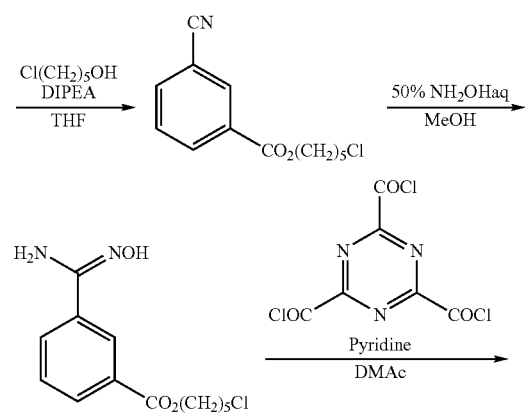

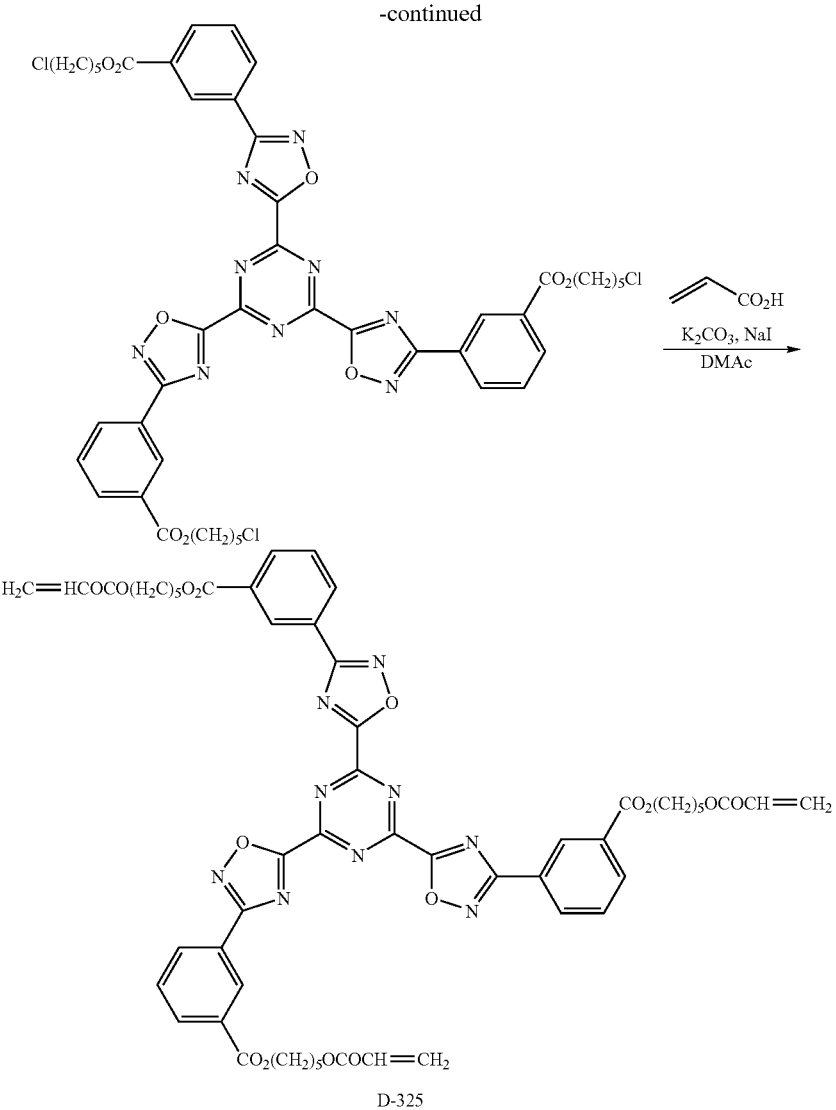

D-325

In the same manner as in Example 11 but using s-triazine-2,4,6-tricarboxylic acid chloride produced according to the method described in *J. Org. Chem.*, 1956, Vol. 21, p. 1392, in place of trimesic acid chloride, 1.5 g of D-325 was obtained. The NMR spectrum of D-325 was as follows:

$^1$H-NMR (solvent: CDCl$_3$, standard: tetramethylsilane) δ (ppm):
1.60 (6H, m)
1.80-1.90 (12H, m)
4.25 (6H, t)
4.45 (6H, t)
5.80 (3H, dd)
6.15 (3H, dd)
6.40 (3H, dd)
7.70 (3H, t)
8.30 (3H, d)
8.50 (3H, d)
8.95 (3H, s)

The phase transition temperature of the thus-obtained D-325 was determined through texture observation with a polarizing microscope. The compound showed a discotic nematic liquid-crystal phase at room temperature. When heated, its phase changed to an isotropic liquid phase at over 116° C. Accordingly, it was found that D-325 shows a discotic nematic liquid-crystal phase within a range of from room temperature to 116° C.

Example 22

Formation of Thin Film of Uniformly Aligned D-227

An aqueous solution of PVA-203 (by Kuraray) was applied onto a glass substrate, and dried at 100° C. for 3 minutes. The thickness of PVA-203 was 0.5 μm. On the substrate on which the thin film of PVA-203 had been formed, a coating solution mentioned below was applied according to a spin-coating method. This was put into a thermostat at 110° C. and, after 1 minute, this was exposed to 600 mJ of UV rays whereby its alignment state was fixed. This was left cooled to room temperature, and then its alignment state was observed with a polarizing microscope. It was found that the discotic liquid-crystalline compound was in homeotropic alignment with no defect therein. The thickness of the liquid-crystalline compound layer was 3.7 μm.

Coating Solution:

| Liquid-crystalline compound D-227 | 100 mas. pts. |
| Air interface alignment-controlling agent V-(2) mentioned below | 0.2 mas. pts. |
| Irgacure 907 (by Nagase Sangyo) | 3.0 mas. pts. |
| Diethylthioxanthone | 1.0 mas. pt. |
| Methyl ethyl ketone | 250 mas. pts. |

Air Interface Alignment-Controlling Agent V-(2):

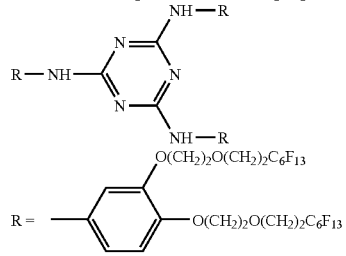

Comparative Example 1

Formation of Thin Film of Conventional Discotic Liquid-Crystalline Compound Uniformly Aligned Therein A coating solution mentioned below was applied onto the polyvinyl alcohol thin film-coated substrate described in Example 10, according to a spin-coating method. This was put into a thermostat at 190° C. and, after 5 minutes, this was exposed to 600 mJ of UV rays whereby its alignment state was fixed. This was left cooled to room temperature, and then its alignment state was observed with a polarizing microscope. It was found that the discotic liquid-crystalline compound was in homeotropic alignment with no defect therein. The thickness of the liquid-crystalline compound layer was 3.0 μm.

Coating Solution:

| Liquid-crystalline compound JD-1 mentioned below | 100 mas. pts. |
| Air interface alignment-controlling agent V-(1) mentioned above | 0.2 mas. pts. |
| Irgacure 907 (by Nagase Sangyo) | 3.0 mas. pts. |
| Diethylthioxanthone | 1.0 mas. pt. |
| Methyl ethyl ketone | 250 mas. pts. |

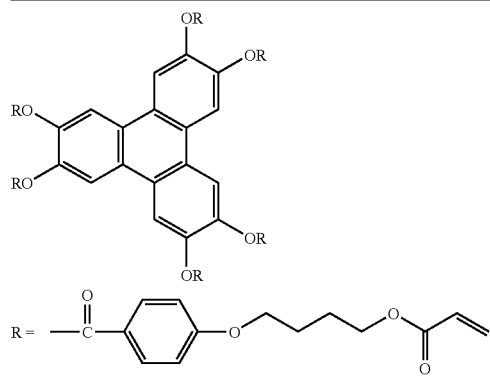

Comparison in Point of Δn and Wavelength Dispersion Value:

In this description, Re(λ) and Rth(λ) indicate the in-plane retardation and the thickness-direction retardation, respectively, at a wavelength λ of films. Using KOBRA (by Oji Keisoku Kiki), light having a wavelength of λ nm is given to a film sample in the normal line direction of the sample, and Re(λ) of the sample is thereby measured. Also using KOBRA, Rth(λ) is determined on the basis of the three retardation data, Re(λ) as above, the retardation value measured by applying light having a wavelength of λ nm to the sample in the direction tilted by +40° relative to the normal line direction of the film with the slow axis (judged by KOBRA) as the tilt axis (rotation axis) thereof, and the retardation value measured by applying light having a wavelength of λ nm to the sample in the direction tilted by −40° relative to the normal line direction of the film with the slow axis as the tilt axis (rotation axis) thereof. For the estimated value of the mean refractive index of the sample, for example, referred to are *Polymer Handbook* (by John Wiley & Sons, Inc.) and various catalogues of optical films. When the mean refractive index of the sample is unknown, it may be measured with an Abbe's refractometer. Data of the mean refractive index of some typical optical films are mentioned below: Cellulose acylate (1.48), cyclo-olefin polymer (1.52), polycarbonate (1.59), polymethyl methacrylate (1.49), polystyrene (1.59).

Using KOBRA, the wavelength dispersion value (Re(478)/Re(748)) of the thin films obtained in Example 10, Example 22 and Comparative Example 1 was determined by measuring their retardation at a tilt angle of 40° and at 478 nm and 748 nm.

Also using KOBRA, Δn of the samples was determined by measuring their Rth(589) according to the method mentioned above followed by diving the value by their thickness (d) separately determined. The results are given in Table 1.

TABLE 1

| | | Δn | Wavelength Dispersion Value |
|---|---|---|---|
| Example 10 | liquid-crystalline compound D-9 of the invention | 0.14 | 1.11 |
| Example 22 | liquid-crystalline compound D-227 of the invention | 0.13 | 1.10 |
| Comparative Example 1 | conventional liquid-crystalline compound JD-1 | 0.09 | 1.18 |

The data in Table 1 confirm that the liquid-crystalline compounds of the invention have a higher Δn (e.g., 0.10 or higher) and a lower wavelength dispersion value (e.g., 1.15 or lower) than those of the conventional liquid-crystalline compound.

Comparative Example 2

A compound JD-2 mentioned below was prepared according to a method described in a reference (Kim, Bong Gi et al's report, *Molecular Crystals and Liquid Crystals*, 2001, Vol. 370, p. 391), and this was injected into a horizontal alignment cell having a cell gap of 10 μm (KSRP-10/A107M1NSS(ZZ), by EHC) at 150° C., and fixed at 130° C. for homeotropic alignment. Next, its wavelength dispersion value was determined according to the above-mentioned method, and was 1.19.

JD-2

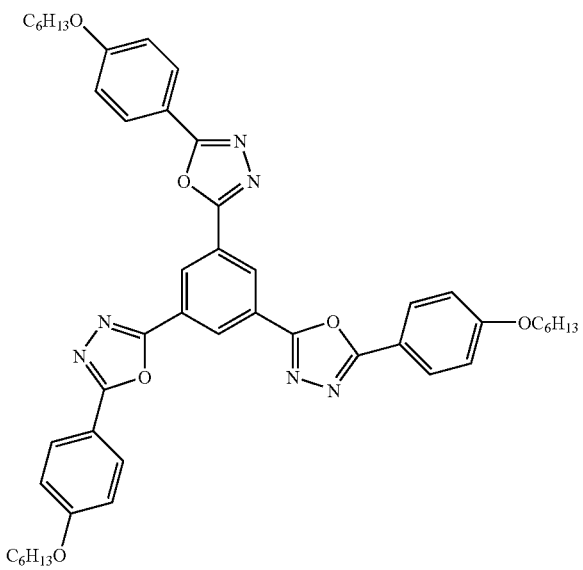

Comparative Example 3

A compound JD-3 mentioned below was injected into a horizontal alignment cell having a cell gap of 10 μm (KSRP-10/A107M1NSS(ZZ), by EHC) at 200° C., and fixed at 190° C. for homeotropic alignment. Next, its wavelength dispersion value was determined according to the above-mentioned method, and was 1.18.

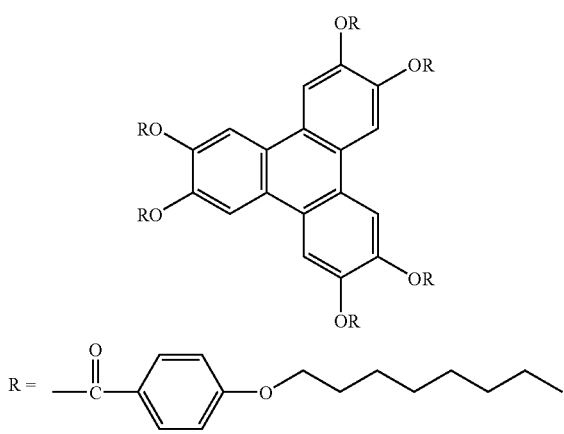

JD-3

Compared with Comparative Example 2 and Comparative Example 3, it has been found that the compounds of the invention have a smaller wavelength dispersion value than not only the conventional, non-polymerizable liquid-crystalline compound JD-3 but also the compound JD-2 having a skeleton similar to that of the compounds of the invention.

Example 23

Fabrication of Retardation Plate

Preparation of Support:

The following composition was put into a mixing tank and stirred with heating to dissolve the ingredients, thereby preparing a cellulose acetate solution. Composition of cellulose acetate solution:

| | |
|---|---|
| Cellulose acetate having a degree of acetylation of 60.9% | 100 parts by mass |
| Triphenyl phosphate (plasticizer) | 7.8 parts by mass |
| Biphenyldiphenyl phosphate (plasticizer) | 3.9 parts by mass |
| Methylene chloride (first solvent) | 300 parts by mass |
| Methanol (second solvent) | 45 parts by mass |
| Dye (Sumika Finechem's 360FP) | 0.0009 parts by mass |

16 parts by mass of a retardation-increasing agent mentioned below, 80 parts by mass of methylene chloride and 20 parts by mass of methanol were put into another mixing tank, and stirred with heating to prepare a retardation-increasing agent solution.

464 parts by mass of the cellulose acetate solution having the composition mentioned above was mixed with 36 parts by mass of the retardation-increasing agent solution and 1.1 parts by mass of silica particles (Aerosil's R972), and well stirred to prepare a dope. The amount of the retardation-increasing agent in the dope was 5.0 parts by mass relative to 100 parts by mass of cellulose acetate therein. The amount of the silica particles was 0.15 parts by mass relative to 100 parts by mass of cellulose acetate.

Retardation-Increasing Agent:

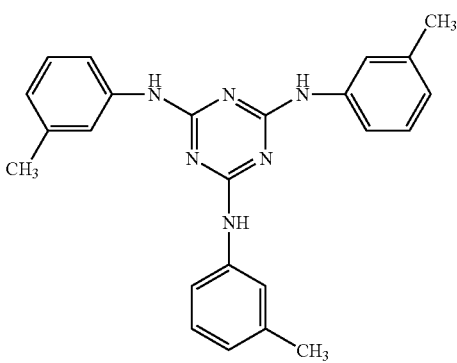

The resulting dope was cast, using a casting machine with a band having a width of 2 m and a length of 65 m. After the temperature of the film surface on the band became 40° C., this was dried for 1 minute and then peeled away. Then, this was 28% stretched in the cross direction, using a tenter with dry air at 140° C. applied thereto. Next, this was dried with dry air at 135° C. for 20 minutes, and a support having a residual solvent amount of 0.3% by weight (PK-1) was thus produced.

Thus obtained, the support (PK-1) had a width of 1340 mm and a thickness of 92 μm. Using an ellipsometer (M-150, by Nippon Bunko), its retardation (Re) at a wavelength of 590 nm was measured and was 38 nm. Its retardation (Rth) measured at a wavelength of 590 nm was 175 nm.

A 1.0 mol/L potassium hydroxide solution (solvent: water/isopropyl alcohol/propylene glycol=69.2 mas.pts./15 mas.pts./15.8 mas.pts.) was applied to the band-side face of the support (PK-1) in an amount of 10 ml/m², and kept at about 40° C. for 30 seconds, and then the alkali solution was scraped away. This was washed with pure water, and the water drops were removed with an air knife. Next, this was dried at 100° C. for 15 seconds. The contact angle of this PK-1 to pure water was measured, and was 42°.

Formation of Alignment Film:

Using a wire bar coater of #16, an alignment film-coating liquid having a composition mentioned below was applied to the PK-1 (on the alkali-processed face), in an amount of 28 ml/m². This was dried with hot air at 60° C. for 60 seconds and then with hot air at 90° C. for 150 seconds to produce an alignment film.

Composition of Alignment Film-Coating Liquid:

| | |
|---|---|
| Modified polyvinyl alcohol mentioned below | 10 parts by mass |
| Water | 371 parts by mass |
| Methanol | 119 parts by mass |
| Glutaraldehyde (crosslinking agent) | 0.5 parts by mass |
| Citrate (Sankyo Chemical's AS3) | 0.35 parts by mass |

$$-(CH_2-CH)_{86.3}-(CH_3-CH)_{12}-(CH_3-CH)_{1.7}-$$
$$\phantom{-(CH_2-}|\phantom{CH)_{86.3}-(CH_3-}|\phantom{CH)_{12}-(CH_3-}|$$
$$\phantom{-(CH_2-}OH\phantom{)_{86.3}-(}O-CO-CH_3\ O-CO-NH-CH_2CH_2O-CO-C(CH_3)=CH_2$$

Rubbing Treatment:

PK-1 was conveyed at a speed of 20 m/sec, and a rubbing roll (having a diameter of 300 mm) was so set relative it that the support could be rubbed at an angle of 45° relative to the machine direction thereof, and rotated under the condition, whereby the alignment film-coated surface of PK-1 was thus rubbed.

Formation of Optically-Anisotropic Layer:

An optically-anisotropic layer-coating liquid having a composition mentioned below was continuously applied onto the alignment film of PK-1 conveyed at 20 m/min, using a wire bar of #3.0 rotated at 470 rpm in the same direction as the film-conveying direction.

Optically-Anisotropic Layer-Coating Liquid:

| | |
|---|---|
| Discotic liquid-crystalline compound (D-227) | 10.00 parts by mass |
| Photopolymerization initiator (Irgacure 907, by Ciba-Geigy) | 3.00 parts by mass |
| Sensitizer (Kayacure DETX, by Nippon Kayaku) | 1.00 part by mass |
| Fluoroaliphatic group-containing copolymer (Megafac F780, by Dai-Nippon Ink) | 0.40 parts by mass |
| Methyl ethyl ketone | 500.00 parts by mass |

The solvent was evaporated away in a process of continuously heating it from room temperature up to 100° C., and then this was heated in a drying zone at 120° C. for about 90 seconds, whereby the discotic liquid-crystal compound was aligned. Next, this was introduced into a drying zone at 80° C., and while the film surface was kept at a temperature of 90° C., this was irradiated with UV rays having a luminance of 600 mW for 4 seconds, using a UV irradiation device (UV lamp: output 160 W/cm, light-emitting length 1.6 m), whereby the crosslinking reaction was promoted and the discotic liquid-crystal compound was fixed as the alignment thereof. Next, this was left cooled to room temperature, and wound up like a cylinder to be a roll film. The process gave an optically-compensatory roll film (KH-1).

Thus fabricated, the optically-compensatory roll film (KH-1) was partly cut to prepare its samples. The samples were analyzed for the optical properties thereof. The retardation Re of the optically-anisotropic layer, as measured at a wavelength of 546 nm, was 30 nm. The angle (tilt angle) of the disc face to the support face of the discotic liquid-crystal compound in the optically-anisotropic layer continuously varied in the direction of the layer thickness, and it was 33° on average. The optically-anisotropic layer alone was peeled off from the sample, and the mean direction of the molecular symmetric axis of the optically-anisotropic layer was measured, and it was 45° relative to the machine direction of the optically-compensatory film (KH-1).

A polarizer was disposed in a cross-Nicol mode, and the resulting optically-compensatory film was checked for the film unevenness. No unevenness was detected both in the front direction and in the direction inclined by 60° from the normal line.

Comparative Example 4

PK-1 was conveyed at a speed of 20 m/min, and a rubbing roll (having a diameter of 300 mm) was set for it so that the rubbing direction could be 45° relative to the machine direction, and rotated at 650 rpm, and the alignment film-coated surface of PK-1 was thus rubbed under the condition.

In the same manner as in Example 23 but using an optically-anisotropic layer-coating liquid mentioned below, an optically-compensatory film (KH-H1) was fabricated. Optically-anisotropic layer-coating liquid:

| | |
|---|---|
| Above-mentioned discotic liquid-crystal compound (JD-1) | 91.00 parts by mass |
| Ethyleneoxide-modified trimethylolpropane triacrylate (V#360, by Osaka Yuki Kagaku) | 9.00 parts by mass |
| Cellulose acetate butyrate (CAB531-1, by Eastman Chemical) | 1.00 part by mass |
| Photopolymerization initiator (Irgacure 907, by Ciba-Geigy) | 3.00 parts by mass |
| Sensitizer (Kayacure DETX, by Nippon Kayaku) | 1.00 part by mass |
| Fluoroaliphatic group-containing copolymer (Megafac F780, by Dai-Nippon Ink) | 0.22 parts by mass |
| Methyl ethyl ketone | 226.34 parts by mass |

Thus fabricated, the optically-compensatory roll film was partly cut to prepare its samples. The samples were analyzed for the optical properties thereof. The retardation Re of the optically-anisotropic layer, as measured at a wavelength of 546 nm, was 31 nm. The angle (tilt angle) of the disc face to the transparent support face of the discotic liquid-crystal compound in the optically-anisotropic layer continuously was 29° on average.

The optically-anisotropic layer was peeled off from PK-1, and the mean direction of the molecular symmetric axis of the optically-anisotropic layer was measured, and it was 45.2° relative to the machine direction of the optically-compensatory film (KH-H1).

Example 24

Fabrication of Polarizer

A PVA film (thickness 80 μm, width 2500 mm) having a mean degree of polymerization of 1700 and a degree of saponification of 99.5 mol % was monoaxially stretched 8-fold in warm water at 40° C., then directly dipped in an aqueous solution of 0.2 g/liter iodine and 60 g/liter potassium iodide at 30° C. for 5 minutes, and then in an aqueous solution of 100 g/liter boric acid and 30 g/liter potassium iodide. In this stage, the film width was 1300 mm and the thickness was 17 μm.

The film was further dipped in a water-washing tank at 20° C. for 10 seconds and then in an aqueous solution of 0.1 g/liter iodine and 20 g/liter potassium iodide at 30° C. for 15 seconds, and thereafter this was dried at room temperature for 24 hours to obtain an iodine-based polarizing film (HF-1).

Using a polyvinyl alcohol-based adhesive, the optically-compensatory film (KH-1) fabricated in Example 23 was stuck to one side of the polarizing film (HF-1) with the support (PK-1) face of the former being inside. On the other hand, a triacetyl cellulose film (TD-80U, by Fuji Photo Film) having a thickness of 80 μm was saponified, and using a polyvinyl alcohol-based adhesive, this was stuck to the other side of the polarizing film.

These were so disposed that the machine direction of the polarizing film and the machine direction of the support (PK-1) and also the machine direction of the commercial triacetyl cellulose film were all in parallel to each other. In that manner, a polarizer (HB-1BR) was fabricated.

On the other hand, using a polyvinyl alcohol-based adhesive, the optically-compensatory film (KH-1) fabricated in Example 23 was stuck to one side of the polarizing film (HF-1) with the support (PK-1) face of the former being inside. On the other hand, an antireflection film (Fuji Film CV-UA, by Fuji Photo Film) was saponified, and using a polyvinyl alcohol-based adhesive, this was stuck to the other side of the polarizing film.

These were so disposed that the machine direction of the polarizing film and the machine direction of the support (PK-1) and also the machine direction of the commercial antireflection film were all in parallel to each other. In that manner, a polarizer (HB-1BF) was fabricated.

Comparative Example 5

Fabrication of Polarizer

Polarizers (HB-H1R, HB-H1F) were fabricated in the same manner as in Example 24 but using KH-H1 (optically-compensatory film) fabricated in Comparative Example 4.

Example 25

Fabrication of Bent Alignment Liquid-Crystal Cell

A polyimide film was stuck to an ITO electrode-fitted glass substrate as an alignment, which was then rubbed. Thus prepared, two glass substrates were placed one upon another in such a manner that the rubbing directions of the two are in parallel to each other, and the cell gap between the two was kept 4.5 μm therebetween. A liquid-crystal compound (SLI1132, by Merck) having Δn of 0.1396 was injected into the cell gap to construct a bent alignment liquid-crystal cell. The size of the liquid-crystal cell was 5 inches.

The polarizers (HB-1BF) and (HB-1BR) fabricated in Example 24 were stuck to the bent alignment cell fabricated herein so that the cell could be sandwiched between the two, in such a manner that the former was on the viewing side and the latter was on the backlight side. The constitutive elements were so disposed that the optically-anisotropic layer of the elliptically-polarizing plate could face the cell substrate and the rubbing direction of the liquid-crystal cell could be antiparallel to the rubbing direction of the optically-anisotropic layer that faces the cell.

A rectangular wave voltage of 55 Hz was applied to the liquid-crystal cell. The mode was a normally white mode of white display 2V and black display 5 V. The transmittance ratio (white display/black display) was referred to as a contrast ratio. Using a contrast meter (EZ-Contrast 160D, by ELDIM), the viewing angle was measured for 8 ranks from black display (L1) to white display (L8), and the angle dependency of color expression was visually checked. In addition, the front contrast (CR: white display brightness/black display brightness) was obtained. The results are given in Table 2.

Comparative Example 6

A panel was fabricated and evaluated in the same manner as in Example 25 but using HB-H1F for the polarizer on the viewing side and using HB-H1R fro the polarizer on the backlight side. The results are given in Table 2.

TABLE 2

| Polarizer Used in Bent Alignment Liquid-Crystal Cell | Viewing Angle* | | | Front CR | Front Color Appearance in black display |
|---|---|---|---|---|---|
| | upper side | lower side | right and left | | |
| Example 25 | 80 | 80 | 80 | 500 | coloration unobserved |
| Comparative Example 6 | 80 | 79 | 80 | 490 | coloration clearly observed |

*Range for contrast ratio of at least 10 and for absence of black-side gradation reversal (reversal between L1 and L2).

The invention claimed is:

1. A compound represented by the following formula (DI):

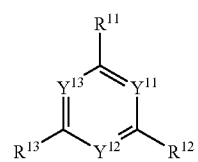

wherein, in formula (DI), $Y^{11}$, $Y^{12}$ and $Y^{13}$ each independently represent a methine group or a nitrogen atom; $R^{11}$, $R^{12}$ and $R^{13}$ each independently represent a group of the following formula (DI-A), (DI-B) or (DI-C):

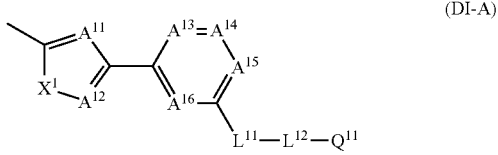

(DI-A)

wherein, in formula (DI-A), $A^{11}$, $A^{12}$, $A^{13}$, $A^{14}$, $A^{15}$ and $A^{16}$ each independently represent a methine group or a nitrogen atom; $X^1$ represents an oxygen atom, a sulfur atom, a methylene group or art imino group; $L^{11}$ represents —O—, —C(=O)—, —O—CO—, —CO—O—, —O—CO—O—, —S—, —NH—, —SO$_2$—, —CH$_2$—, —CH=CH—, or —C≡C—; $L^{12}$ represents a divalent linking group selected from the group consisting of —O—, —S—, —C(=O)—, —SO$_2$—, —NH—, —CH$_2$—, —CH=CH— and —C≡C—, and their combinations; when the above-mentioned groups contain a hydrogen atom, then the hydrogen atom may be substituted with a substituent selected from the group consisting of a halogen atom, a hydroxyl group, and an alkyl group having from 1 to 6 carbon atoms; $Q^{11}$ each independently represents a polymerizable group or a hydrogen atom,

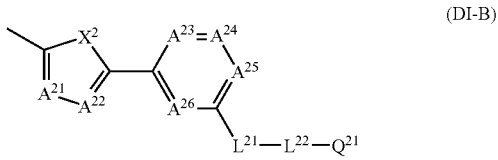

(DI-B)

wherein, in formula (DI-B), $A^{21}$, $A^{22}$, $A^{23}$, $A^{24}$, $A^{25}$ and $A^{26}$ each independently represent a methine group or a nitrogen atom; $X^2$ represents an oxygen atom, a sulfur atom, a methylene group or an imino group; $L^{21}$ represents —O—, —C(=O)—, —O—CO—, —CO—O—, —O—CO—O—, —S—, —NH—, —SO$_2$—, —CH$_2$—, —CH=CH—, or —C≡C—; $L^{22}$ represents a divalent linking group selected from the group consisting of —O—, —S—, —C(=O)—, —SO$_2$—, —NH—, —CH$_2$—, —CH=CH— and —C≡C—, and their combinations; when the above-mentioned groups contain a hydrogen atom, then the hydrogen atom may be substituted with a substituent selected from the group consisting of a halogen atom, a hydroxyl group, and an alkyl group having from 1 to 6 carbon atoms; $Q^{21}$ each independently represents a polymerizable group or a hydrogen atom,

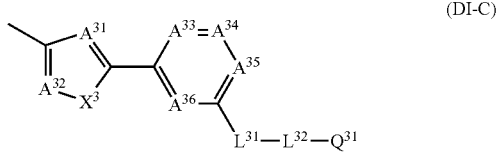

(DI-C)

wherein, in formula (DI-C), $A^{31}$, $A^{32}$, $A^{33}$, $A^{34}$, $A^{35}$ and $A^{36}$ each independently represent a methine group or a nitrogen atom; $X^3$ represents an oxygen atom, a sulfur atom, a methylene group or an imino group; $L^{31}$ represents —O—, —C(=O)—, —O—CO—, —CO—O—, —O—CO—O—, —S—, —NH—, —SO$_2$—, —CH$_2$—, —CH=CH—, or —C≡C—; $L^{32}$ represents a divalent linking group selected from the group consisting of —O—, —S—, —C(=O)—, —SO$_2$—, —NH—, —CH$_2$—, —CH=CH— and —C≡C—, and their combinations; when the above-mentioned groups contain a hydrogen atom, then the hydrogen atom may be substituted with a substituent selected from the group consisting of a halogen atom, a hydroxyl group, and an alkyl group having from 1 to 6 carbon atoms; $Q^{31}$ each independently represents a polymerizable group or a hydrogen atom.

2. The compound of claim 1 wherein $A^{11}$, $A^{12}$, $A^{21}$, $A^{22}$, $A^{31}$ and $A^{32}$ represent a nitrogen atom.

3. The compound of claim 1 wherein $X^1$, $X^2$ and $X^3$ represent an oxygen atom.

4. The compound of claim 1 wherein $A^{13}$, $A^{14}$, $A^{15}$, $A^{16}$, $A^{23}$, $A^{24}$, $A^{25}$, $A^{26}$, $A^{33}$, $A^{34}$, $A^{35}$ and $A^{36}$ represent a methine group.

5. The compound of claim 1 wherein $R^{11}$, $R^{12}$ and $R^{13}$ represents a group of formula (DI-A).

6. The compound of claim 5 wherein $L^{11}$ represents —O—, —CO—O— or —C≡C—.

7. A composition comprising the compound of claim 1.

8. A retardation plate comprising at least one optically-anisotropic layer on a transparent support, wherein the optically-anisotropic layer is formed of a composition comprising a compound represented by the following formula (DII):

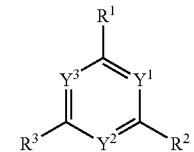

(DII)

wherein, in formula (DII), $Y^1$, $Y^2$ and $Y^3$ each independently represent a methine group or a nitrogen atom; $R^1$, $R^2$ and $R^3$ each independently represent a group of the following formula (DII-H):

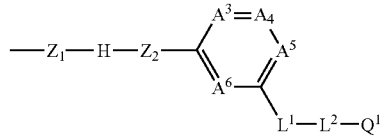

(DII-H)

wherein, in formula (DII-H), H represents a divalent 5-membered cyclic group; $Z^1$ and $Z^2$ each independently represent a single bond or a divalent linking group; $A^3$, $A^4$, $A^5$ and $A^6$ each independently represent a methine group or a nitrogen atom; $L^1$ represents —O—, —C(=O)—, —O—CO—, —CO—O—, —O—CO—O—, —S—, —NH—, —SO$_2$—, —CH$_2$—, —CH=CH—, or —C≡C—; $L^2$ represents a divalent linking group selected from the group consisting of —O—, —S—, —C(=O)—, —SO$_2$—, —NH—, —CH$_2$—, —CH=CH— and —C≡C—, and their combinations; when the above-mentioned groups contain a hydrogen atom, then the hydrogen atom may be substituted with a substituent selected from the group consisting of a halogen atom, a hydroxyl group, and an alkyl group having from 1 to 6 carbon atoms; $Q^1$ each independently represents a polymerizable group or a hydrogen atom.

9. An elliptically-polarizing plate comprising the retardation plate of claim 8 and a polarizing film.

10. A liquid-crystal display device comprising the retardation plate of claim 8 or an elliptically-polarizing plate comprising the retardation plate of claim 8.

11. The compound of claim 1, wherein each of $Q^{11}$, $Q^{21}$ and $Q^{31}$ is a polymerizable group.

* * * * *